(12) United States Patent
Carlson

(10) Patent No.: US 7,884,052 B2
(45) Date of Patent: *Feb. 8, 2011

(54) COMBINATORIAL ARTIFICIAL RECEPTORS INCLUDING TETHER BUILDING BLOCKS ON SCAFFOLDS

(75) Inventor: Robert E. Carlson, Minnetonka, MN (US)

(73) Assignee: Receptors LLC, Chaska, MN (US)

(*) Notice: Subject to any disclaimer, the term of this patent is extended or adjusted under 35 U.S.C. 154(b) by 905 days.

This patent is subject to a terminal disclaimer.

(21) Appl. No.: 11/219,338

(22) Filed: Sep. 1, 2005

(65) Prior Publication Data

US 2006/0205011 A1    Sep. 14, 2006

Related U.S. Application Data

(60) Provisional application No. 60/609,160, filed on Sep. 11, 2004, provisional application No. 60/612,666, filed on Sep. 23, 2004, provisional application No. 60/626,770, filed on Nov. 10, 2004, provisional application No. 60/645,582, filed on Jan. 19, 2005, provisional application No. 60/649,729, filed on Feb. 3, 2005, provisional application No. 60/607,438, filed on Sep. 3, 2004, provisional application No. 60/607,458, filed on Sep. 3, 2004, provisional application No. 60/608,557, filed on Sep. 10, 2004, provisional application No. 60/607,457, filed on Sep. 3, 2004, provisional application No. 60/608,654, filed on Sep. 10, 2004.

(51) Int. Cl.
    C40B 40/00    (2006.01)
(52) U.S. Cl. .................. 506/13; 506/7; 506/23
(58) Field of Classification Search .................. None
    See application file for complete search history.

(56) References Cited

U.S. PATENT DOCUMENTS

| | | | |
|---|---|---|---|
| 4,344,438 A | 8/1982 | Schultz | |
| 5,159,656 A | 10/1992 | Goldstein | |
| 5,178,673 A | 1/1993 | Caster et al. | |
| 5,225,374 A | 7/1993 | Fare et al. | |
| 5,281,539 A | 1/1994 | Schramm | |
| 5,324,633 A | 6/1994 | Fodor et al. | |
| 5,340,474 A | 8/1994 | Kauvar | |
| 5,453,533 A | 9/1995 | Luo et al. | |
| 5,475,100 A | 12/1995 | Hashino et al. | |
| 5,508,164 A | 4/1996 | Kausch et al. | |
| 5,512,435 A * | 4/1996 | Renschler et al. | ............. 506/10 |
| 5,632,957 A | 5/1997 | Heller et al. | |
| 5,677,196 A | 10/1997 | Herron et al. | |
| 5,677,441 A | 10/1997 | Waldman et al. | |
| 5,690,894 A | 11/1997 | Pinkel et al. | |
| 5,770,380 A | 6/1998 | Hamilton et al. | |
| 5,804,563 A | 9/1998 | Still et al. | |
| 5,925,529 A | 7/1999 | Coughlin et al. | |
| 5,942,393 A | 8/1999 | Nobori et al. | |
| 5,990,163 A | 11/1999 | Evans et al. | |
| 5,993,653 A | 11/1999 | Ahmed et al. | |
| 5,998,594 A | 12/1999 | Goodman et al. | |
| 6,030,782 A | 2/2000 | Anderson et al. | |
| 6,030,917 A * | 2/2000 | Weinberg et al. | ............. 506/21 |
| 6,061,636 A | 5/2000 | Horlbeck | |
| 6,066,448 A | 5/2000 | Wohlstadter et al. | |
| 6,083,758 A | 7/2000 | Imperiali et al. | |
| 6,083,763 A | 7/2000 | Balch | |
| 6,096,551 A | 8/2000 | Barbas et al. | |
| 6,111,123 A | 8/2000 | Coucouvanis et al. | |
| 6,153,743 A | 11/2000 | Hubbell et al. | |
| 6,168,912 B1 | 1/2001 | Chen | |
| 6,207,369 B1 | 3/2001 | Wohlstadter et al. | |
| 6,225,047 B1 | 5/2001 | Hutchens et al. | |
| 6,251,864 B1 | 6/2001 | Dower et al. | |
| 6,261,776 B1 | 7/2001 | Pirrung et al. | |
| 6,287,765 B1 | 9/2001 | Cubicciotti | |
| 6,297,059 B1 | 10/2001 | Song et al. | |
| 6,310,191 B1 | 10/2001 | Collins et al. | |
| 6,312,664 B1 | 11/2001 | Brasch et al. | |
| 6,316,268 B1 | 11/2001 | Yang et al. | |
| 6,316,616 B1 | 11/2001 | Jacobsen et al. | |
| 6,331,441 B1 | 12/2001 | Balch et al. | |

(Continued)

FOREIGN PATENT DOCUMENTS

DE    197 40 263    5/1998

(Continued)

OTHER PUBLICATIONS

Sila et al., Journal of Molecular Recognition, 8:29-34 (1995).*

(Continued)

*Primary Examiner*—Jeffrey S. Lundgren
(74) *Attorney, Agent, or Firm*—Merchant & Gould P.C.

(57) ABSTRACT

The present invention relates to artificial receptors on scaffolds, methods of and compositions for making them, and methods of using them. Each artificial receptor includes a plurality of building block compounds coupled to a scaffold. In an embodiment, at least one of the building blocks includes a tether moiety. The tether can provide spacing or distance between the recognition element and the scaffold to which the building block is immobilized. A tether moiety can have any of a variety of characteristics or properties including flexibility, rigidity or stiffness, ability to bond to another tether moiety, and the like.

11 Claims, 50 Drawing Sheets

U.S. PATENT DOCUMENTS

| | | | |
|---|---|---|---|
| 6,344,272 B1 | 2/2002 | Oldenburg et al. |
| 6,346,413 B1 | 2/2002 | Fodor et al. |
| 6,346,423 B1 | 2/2002 | Schembri |
| 6,361,944 B1 | 3/2002 | Mirkin et al. |
| 6,372,907 B1 | 4/2002 | Lee et al. |
| 6,410,585 B1 | 6/2002 | Larsen et al. |
| 6,419,881 B1 | 7/2002 | Weinberg et al. |
| 6,428,811 B1 | 8/2002 | West et al. |
| 6,489,093 B1 | 12/2002 | Jacobsen et al. |
| 6,528,020 B1 | 3/2003 | Dai et al. |
| 6,543,936 B2 | 4/2003 | Feldman |
| 6,562,566 B1 | 5/2003 | Hoheisel |
| 6,627,396 B1 | 9/2003 | Swanson et al. |
| 6,645,517 B2 | 11/2003 | West et al. |
| 6,649,356 B2 | 11/2003 | Bryan et al. |
| 6,652,835 B1 | 11/2003 | Lauffer et al. |
| 6,667,159 B1 | 12/2003 | Walt et al. |
| 6,673,533 B1 | 1/2004 | Wohlstadter et al. |
| 6,698,201 B1 | 3/2004 | Sarkar et al. |
| 6,699,501 B1 | 3/2004 | Neu et al. |
| 6,699,719 B2 | 3/2004 | Yamazaki et al. |
| 6,767,194 B2 | 7/2004 | Jeon et al. |
| 6,767,706 B2 | 7/2004 | Quake et al. |
| 6,844,165 B2 | 1/2005 | Hutchens et al. |
| 6,872,574 B2 | 3/2005 | Cravatt et al. |
| 6,875,620 B1 | 4/2005 | Schembri |
| 7,018,792 B2 | 3/2006 | Swanson et al. |
| 7,160,734 B2 | 1/2007 | Hutchens et al. |
| 2002/0019015 A1 | 2/2002 | Lahiri et al. |
| 2002/0090728 A1 | 7/2002 | Shair et al. |
| 2002/0187197 A1 | 12/2002 | Caruso et al. |
| 2002/0187347 A1 | 12/2002 | Halas et al. |
| 2002/0187509 A1 | 12/2002 | Shao et al. |
| 2003/0083235 A1 | 5/2003 | Danishefsky et al. |
| 2003/0104360 A1 | 6/2003 | Still et al. |
| 2003/0138853 A1 | 7/2003 | Lahiri et al. |
| 2003/0143756 A1 | 7/2003 | Fisher et al. |
| 2003/0156991 A1 | 8/2003 | Halas et al. |
| 2003/0175517 A1 | 9/2003 | Voigt et al. |
| 2003/0219384 A1 | 11/2003 | Donath et al. |
| 2003/0228605 A1* | 12/2003 | Slootstra et al. ............... 435/6 |
| 2004/0010126 A1 | 1/2004 | Lubman et al. |
| 2004/0013721 A1 | 1/2004 | Antipov et al. |
| 2004/0076681 A1 | 4/2004 | Dennis et al. |
| 2004/0077102 A1 | 4/2004 | Coute et al. |
| 2004/0102607 A1 | 5/2004 | Danishefsky et al. |
| 2004/0137526 A1 | 7/2004 | Hanash et al. |
| 2004/0151733 A1 | 8/2004 | Livingston et al. |
| 2004/0185473 A1 | 9/2004 | Cuppoletti et al. |
| 2004/0203049 A1 | 10/2004 | Schembri |
| 2004/0208884 A1 | 10/2004 | Danishefsky et al. |
| 2006/0051802 A1 | 3/2006 | Carlson |

FOREIGN PATENT DOCUMENTS

| | | |
|---|---|---|
| EP | 0482727 A2 | 4/1992 |
| EP | 1143252 A1 | 10/2001 |
| EP | 1310794 A2 | 5/2003 |
| GB | 2 319 838 A | 6/1998 |
| JP | 7-188278 | 7/1995 |
| JP | 11-509736 | 8/1999 |
| WO | WO 93/25910 | 12/1993 |
| WO | WO 95/02566 | 1/1995 |
| WO | WO 98/12156 | 3/1998 |
| WO | WO 99/25384 | 5/1999 |
| WO | WO 00/13016 | 3/2000 |
| WO | WO 00/13017 | 3/2000 |
| WO | WO 00/16733 | 3/2000 |
| WO | WO 00/66790 | 11/2000 |
| WO | WO 00/79008 A2 | 12/2000 |
| WO | WO 01/01140 A1 | 1/2001 |
| WO | WO 01/02839 A1 | 1/2001 |
| WO | WO 01/18545 A2 | 3/2001 |
| WO | WO 01/46698 A2 | 6/2001 |
| WO | WO 02/08154 | 1/2002 |
| WO | WO 02/42775 A2 | 5/2002 |
| WO | WO 03/012390 A2 | 2/2003 |
| WO | WO 03/031975 A1 | 4/2003 |
| WO | WO 03/033674 A2 | 4/2003 |
| WO | WO 03/043684 A1 | 5/2003 |
| WO | WO 03/074990 A2 | 9/2003 |
| WO | WO 2004/011476 | 2/2004 |
| WO | WO 2006/017180 | 2/2006 |
| WO | WO 2006/061207 A1 | 6/2006 |

OTHER PUBLICATIONS

"Introducing Human Cancer OligoArray™", Sigma Genosys, 1 page (2002).

Buchanan, J. et al., "Practical synthesis of fully-substituted peptide thiazoles," Tetrahedron Letters, vol. 40, pp. 3985-3988 (1999).

International Search Report dated Feb. 9, 2006.

International Search Report mailed Mar. 14, 2006.

Grabar, K. et al., "Two-Dimensional Arrays of Colloidal Gold Particles: A Flexible Approach to Macroscopic Metal Surfaces", Langmuir, 12:2353-2361 (1996).

Morgenthaler, S. et al., "Surfaces with a Hydrophobicity Gradient: Possible Applications in Biological Testing", European Cells and Materials, 6(1):69 (2001).

Naffin, J. et al., "Immobilized Peptides as High-Affinity Capture Agents for Self-Associating Proteins", Chemistry & Biology, 10:251-259 (2003).

Reid et al., "Conformationally Constrained Macrocycles that Mimic Tripeptide b-Strands in Water and Aprotic Solvents," J. Am. Chem. Soc., vol. 124, pp. 5673-5683 (May 22, 2002).

Ruardy, T. et al., "Preparation and charatterization of chemical gradient surfaces and their application for the study of cellular interaction phenomena", Surface Science Reports, 29:1-30 (1997).

Sasaki, D. et al., "Crown Ether Functionalized Lipid Membranes: Lead Ion Recognition and Molecular Reorganization", Langmuir, vol. 18, pp. 3714-3721 (2002).

Tsuda, M. et al., "Suberedamines A and B, New Bromotyrosine Alkaloids from a Sponge Suberea Species," J. Nat. Prod., vol. 64, pp. 980-982 (2001).

Various Search Reports, 109 pages (2001-2002).

U.S. Appl. No. 10/703,876 Office Action Nov. 15, 2007.

U.S. Appl. No. 10/706,573 Office Action Oct. 18, 2007.

U.S. Appl. No. 10/727,059 Office Action Nov. 15, 2007.

Non-proprietary Summary dated Nov. 29, 2001 that may have been sent to the Department of Defense and the National Institutes of Health.

U.S. Appl. No. 10/934,193 Office Action May 16, 2008.

U.S. Appl. No. 10/934,977 Office Action Apr. 8, 2008.

U.S. Appl. No. 11/004,593 Office Action Apr. 14, 2008.

U.S. Appl. No. 11/217,384 Office Action Apr. 29, 2008.

U.S. Appl. No. 11/219,515 Office Action Apr. 30, 2008.

U.S. Appl. No. 10/244,727 Office Action Jul. 2, 2008.

Adams et al., "Oligosaccharide and Glycoprotein Micorarrays as Tools in HIV Glycobiology: Glycan-Dependent gp120/Protein Interactions," Chemistry & Biology, vol. 11, 875-881, Jun. 2004.

Bryan et al., "Saccharide Display on Microtiter Plates," Chemistry & Biology, vol. 9, 713-720, Jun. 2002.

Bryan et al., "Covalent Display of Oligosaccharide Arrays in Microtiter Plates," J. Am Chem. Soc. 2004, 126, 8640-8641.

Cho et al., "Pin-Printed Chemical Sensor Arrays for Simultaneous Multianalyte Quantification," Anal. Chem. 2002, 74, 1462-1466.

Collins et al., "Cell Surface Biology Mediated by Low Affinity Multivalent Protein-Glycan Interactions," Current Opinion in Chemical Biology, 2004,8:617-625.

Disney et al., "Aminoglycoside Microarrays to Study Antibiotic Resistance," Angew. Chem. Int. Ed. 2004, 43, 1591-1594.

Disney et al., "Aminoglycisde Microarrays to Explore Interactions of Antibiotics with RNAs and Proteins," Chem. Eur. J., 2004, 10, 3308-3314.

Disney et al., "The Use of Carbohydrate Microarrays to Study Carbohydrate-Cell Interactions and to Detect Pathogens," *Chemistry & Biology*, vol. 11, 1701-1707, Dec. 2004.

Fukui et al., "Oligosaccharrdie Microarrays for High-Throughput Detection and Specificity Assignmetns of Carbohydrate-Protein Interactions," *Nature Biotechnology*, Oct. 2002, vol. 20, 1011-1017.

Houseman et al., "Carbohydrate Arrays for the Evaluation of Protein Binding and Enzymatic Modification," *Chemistry & Biology*, vol. 9, 443-454, Apr. 2002.

Kuruvilla et al., "Dissecting Glucose Signalling with Diversity-Oriented Synthesis and Small-Molecule Microarrays," *Nature*, vol. 416, Apr. 2002, 653-657.

Mahal, "Catching Bacteria with Sugar," *Chemistry & Biology*, vol. 11, Dec. 2004.

Mellet et al., "Carbohydrate Microarrays," *ChemBioChem*, 2002, 3, 819-822.

Michael et al., "Randomly Ordered Addressable High-Density Optical Sensor Arrays," *Anal. Chem.*, 1998, 70, 1242-1248.

Ni et al., "Synthesis of Maleimide-Activated Carbohydrates as Chemoselective Tags for Site-Specific Glycosylation of Peptides and Proteins," *Bioconjugate Chem.*, 2003, 14, 232-238.

Nimrichter et al., "Intact Cell Adhesion to Glycan Microarrays," *Glycobiology*, vol. 14, No. 2, pp. 197-203, 2004.

Ratner et al., "Probing Protein-Carbohydrate Interactions with Microarrays of Synthetic Oligosaccharides," *ChemBioChem*, 2004, 5, 379-383.

International Search Report mailed Mar. 8, 2006.

CARA presented Sep. 10, 2003.

International Search Report dated May 27, 2004.

International Search Report dated Mar. 7, 2005.

International Search Report dated Mar. 10, 2005.

International Search Report dated Apr. 28, 2005.

International Search Report dated May 3, 2005.

International Search Report dated Sep. 8, 2005.

Developing Nano, http://www.nanosysinc.com/technology.html, pp. 1-12 (May 3, 2004).

Various Search Reports, 73 pages (2004).

Aguilar, Z. et al., "Self-Contained Microelectrochemical Immunoassay for Small Volumes Using Mouse IgG as a Model System," *Anal. Chem.*, vol. 74, No. 14, pp. 3321-3329 (Jul. 15, 2002).

Ainsworth, S., "Nanotech IP: As nanometer-scale materials start making money, intellectual property issues are heating up," *Chemical & Engineering News*, vol. 82, No. 15, pp. 17-22 (Apr. 12, 2004).

Albert, K. et al., "Cross-Reactive Chemical Sensor Arrays," *Chemical Reviews*, vol. 100, No. 7, pp. 2595-2626 (2000).

Alberti, P. et al., "DNA duplex-quadruplex exchange as the basis for a nanomolecular machine," *PNAS*, vol. 100, No. 4, pp. 1569-1573 (Feb. 18, 2003).

Alluri, P. et al., "Isolation of Protein Ligands from Large Peptoid Libraries," Center for Biomedical Inventions, Department of Internal Medicine and Molecular Biology, University of Texas Southwestern Medical Center, pp. 1-44 (2003).

Aziz, H., "Route to Carbon Nanotube Solubilization and Applications," *Dept. of Chem., Duke University, for Chem 110*, pp. 1-15, Submitted Nov. 25, 2003.

Bachhawat-Sikder, K. et al., "Mixed-Element Capture Agents: A Simple Strategy for the Construction of Synthetic, High-Affinity Protein Capture Ligands," *J. Am. Chem. Soc.*, vol. 125, No. 32, pp. 9550-9551 (2003).

Bakker, E., "Electrochemical Sensors," *Anal. Chem.*, vol. 76, No. 12, pp. 3285-3298 (Jun. 15, 2004).

Ball, P., "Yarn spun from nanotubes," *Nature*, http://www.nature.com/nsu/040308/040308-10.html, (Mar. 12, 2004).

Barbaro, A. et al., "CHEMFET Devices for Biomedical and Environmental Applications," *Advanced Materials*, vol. 4, No. 6, pp. 402-408 (1992).

Basabe-Desmonts, L. et al., "A Simple Approach to Sensor Discovery and Fabrication on Self-Assembled Monolayers on Glass," *J. Am. Chem. Soc.*, vol. 126, No. 23, pp. 7293-7299 (2004).

Blackwell, H. et al., "Exploiting Site-Site Interactions on Solid Support to Generate Dimeric Molecules," *Organic Letters*, vol. 3, No. 8, pp. 1185-1188 (2001).

Bluhm, L. et al., "An Alternative Procedure to Screen Mixture Combinatorial Libraries for Selectors for Chiral Chromatography," *Analytical Chemistry*, vol. 72, No. 21, pp. 5201-5205 (Nov. 1, 2000).

Borchardt, A. et al., "Synthetic Receptor Binding Elucidated with an Encoded Combinatorial Library," *J. Am. Chem. Soc.*, vol. 116, No. 1, pp. 373-374 (1994).

Boyce, R. et al., "Peptidosteroidal Receptors for Opioid Peptides, Sequence-Selective Binding Using a Synthetic Receptor Library," *J. Am. Chem. Soc.*, vol. 116, No. 17, pp. 7955-7956 (1994).

Brennan, M., "Protein Interactions: Putting on the Brakes. Antibody Mimics that Bind to Protein Surface Block Protein-Protein Interactions," *C & EN*, pp. 65-66, 69 (Jan. 22, 2001).

Breslow, R. et al., "Sequence Selective Binding of Peptides by Artificial Receptors in Aqueous Solution," *J. Am. Chem. Soc.*, vol. 120, No. 14, pp. 3536-3537 (1998).

Bunin, B. et al., "A General and Expedient Method for the Solid-Phase Synthesis of 1,4-Benzodiazepine Derivatives," *J. Am. Chem. Soc.*, vol. 114, pp. 10997-10998 (1992).

Burns, C. et al., "Components for Tethered Bilayer Membranes: Synthesis of Hydrophilically Substituted Phytanol Derivatives," *Aust. J. Chem.*, vol. 54, pp. 431-438 (2001).

Caswell, K. et al., "Preferential End-to-End Assembly of Gold Nanorods by Biotin-Streptavidin Connectors," *J. Am. Chem. Soc.*, vol. 125, No. 46, pp. 13914-13915 (2003).

Cha, X. et al., "Molecular Recognition of Aqueous Dipeptides by Noncovalently Aligned Oligoglycine Units at the Air/Water Interface," *J. Am. Chem. Soc.*, vol. 117, No. 48, pp. 11833-11838 (1995).

Chambers, R. et al., "High-level generation of polyclonal antibodies by genetic immunization," *Nature Biotechnology*, vol. 21, No. 9, pp. 1088-1092 (Sep. 2003).

Chen, J. et al., "Biased Combinatorial Libraries: Novel Ligands for the SH3 Domain of Phosphatidylinositol 3-Kinase," *J. Am. Chem. Soc.*, vol. 115, No. 26, pp. 12591-12592 (1993).

Cheng, Y. et al., "Sequence-Selective Peptide Binding with a Peptido-A,B-*trans*-steroidal Receptor Selected from an Encoded Combinatorial Receptor Library," *J. Am. Chem. Soc.*, vol. 118, No. 7, pp. 1813-1814 (1996).

Cousins, G. et al., "Molecular Evolution: Dynamic Combinatorial Libraries, Autocatalytic Networks and the Quest for Molecular Function," *Current Opinion in Chemical Biology*, vol. 4, pp. 270-279 (2000).

Dai, Z. et al., "Reagentless Amperometric Immunosensors Based on Direct Electrochemistry of Horseradish Peroxidase for Determination of Carcinoma Antigen-125," *Anal. Chem.*, vol. 75, No. 20, pp. 5429-5434 (Oct. 15, 2003).

DeLong, S. et al., "Covalently immobilized gradients of bFGF on hydrogel scaffolds for directed cell migration," *Biomaterials*, vol. 26, pp. 3227-3234 (2005).

Deng, Q. et al., "Retention and Separation of Adenosine and Analogues by Affinity Chromatography with an Aptamer Stationary Phaase," *Anal. Chem.*, vol. 73, No. 22, pp. 5415-5421 (Nov. 15, 2001).

Dertinger, S. et al., "Gradients of substrate-bound laminin orient axonal specification of neurons," *PNAS*, vol. 99, No. 20, pp. 12542-12547 (Oct. 1, 2002).

Diamond, D., "Internet-Scale Sensing," *Analytical Chemistry*, vol. 76, No. 15, pp. 279A-286A (Aug. 1, 2004).

Ellman, J. et al., "Combinatorial thinking in chemistry and biology," *Proc. Natl. Acad. Sci. USA*, vol. 94, pp. 2779-2782 (Apr. 1997).

Feder, B., "Bashful vs. Brash in the New Field of Nanotech," *The New York Times*, 5 pages, http://www.nytimes.com/2004/03/15/technology/15nano.html?ei=1&en=873c8a6f53eb2287&ex=1080357865&adxnnl..., (Mar. 15, 2004).

Fiammengo, R. et al., "Synthetic Self-Assembled Models with Biomimetic Functions," *Current Opinion in Chemical Biology*, vol. 5, pp. 660-673 (2001).

Francis, M. et al., "Combinatorial Approach to the Discovery of Novel Coordination Complexes," *J. Am. Chem. Soc.*, vol. 118, No. 37, pp. 8983-8984 (1996).

Freemantle, M., "Amplification of the Fittest. Dynamic Combinatorial Library Strategy Leads to Discovery and Synthesis of New Compounds," *Chemical & Engineering News*, vol. 80, No. 35, pp. 31-33 (Sep. 2, 2002).

Furlan, R. et al., "A New Cyclic Pseudopeptide Receptor for Li+ from a Dynamic Combinatorial Library," *J. Am. Chem. Soc.*, vol. 123, No. 36, pp. 8876-8877 (2001).

Goodman, M. et al., "A Combinatorial Library Approach to Artificial Receptor Design," *J. Am. Chem. Soc.*, vol. 117, No. 46, pp. 11610-11611 (1995).

Grant, S. et al., "Labeless and reversible immunosensor assay based upon an electrochemical current-transient protocol," *Analytica Chimica Acta*, vol. 495, pp. 21-32 (2003).

Grennan, K. et al., "Atrazine analysis using an amperometric immunosensor based on single-chain antibody fragments and regeneration-free multi-calibrant measurement," *Analytica Chimica Acta*, vol. 500, pp. 287-298 (2003).

Gwynne, P. et al., "Proteomics 3: Probing Proteins' Structures," *Drug Discovery and Biotechnology Trends*, pp. 689-699 (Jul. 30, 2004).

Halter, M. et al., "Engineered Lipids That Cross-Link the Inner and Outer Leaflets of Lipid Bilayers," *Langmuir*, vol. 20, No. 6, pp. 2416-2423 (2004).

Hamilton, A. et al., "Model Systems Artificial Models of Protein Function," *Current Opinion in Chemical Biology*, vol. 5, pp. 623-625 (2001).

Hamuro, Y. et al., "A Calixarene with Four Peptide Loops: An Antibody Mimic for Recognition of Protein Surfaces," *Angew. Chem. Int. Ed. Engl.*, vol. 36, No. 23, pp. 2680-2683 (1997).

Hamuro, Y. et al., "Functionalized Oligoanthranilamides: Modular and Conformationally Controlled Scaffolds," *Bioorganic & Medicinal Chemistry*, vol. 9, pp. 2355-2363 (2001).

Haupt, K. et al., "Molecularly Imprinted Polymers and Their Use in Biomimetic Sensors," *Chem. Rev.*, vol. 100, No. 7, pp. 2495-2504 (2000).

Hergenrother, P. et al., "Small-Molecule Microarrays: Covalent Attachment and Screening of Alcohol-Containing Small Molecules on Glass Slides," *J. Am. Chem. Soc.*, vol. 122, No. 32, pp. 7849-7850 (2000).

Hubbard, R. et al., "Highly Substituted *ter*-Cyclopentanes as Receptors for Lipid A," *J. Am. Chem. Soc.*, vol. 123, No. 24, pp. 5810-5811 (2001).

Huc, I. et al., "Virtual Combinatorial Libraries: Dynamic Generation of Molecular and Supramolecular Diversity by Self-Assembly," *Proc. Natl. Acad. Sci. USA*, vol. 94, pp. 2106-2110 (Mar. 1997).

Hypolite, C. et al., "Formation of Microscale Gradients of Protein Using Heterobifunctional Photolinkers," *Bioconjugate Chem.*, vol. 8, No. 5, pp. 658-663 (1997).

Jacoby, M., "Chiral Catalysis at Surfaces," *C & EN*, pp. 37-41 (Mar. 15, 2004).

Jain, R. et al., "Protein Surface Recognition by Synthetic Receptors Based on a Tetraphenylporphyrin Scaffold," *Organic Letters*, vol. 2, No. 12, pp. 1721-1723 (2000).

Kasher, R. et al., "Design and Synthesis of Peptides that Bind α-Bungarotoxin with High Affinity," *Chemistry & Biology*, vol. 8, pp. 147-155 (2001).

Kick, E. et al., "Structure-Based Design and Combinatorial Chemistry Yield Low Nanomolar Inhibitors of Cathepsin D," *Chemistry & Biology*, vol. 4, No. 4, pp. 297-307 (Apr. 1997).

Kimura, M. et al., "Construction of Regulated Nanospace around a Porphyrin Core," *J. Am. Chem. Soc.*, vol. 123, No. 24, pp. 5636-5642 (2001).

Kodadek, T., "Protein microarrays: prospects and problems," *Chemistry & Biology*, vol. 8, pp. 105-115 (2001).

Kodadek, T., "Development of Protein-Detecting Microarrays and Related Devices," *TRENDS in Biochemical Sciences*, vol. 27, No. 6, pp. 295-300 (Jun. 2002).

Kojima, K. et al., "Electrochemical Protein Chip with Arrayed Immunosensors with Antibodies Immobilized in a Plasma-Polymerized Film," *Anal. Chem.*, vol. 75, No. 5, pp. 1116-1122 (Mar. 1, 2003).

Korbel, G. et al., "Reaction Microarrays: A Method for Rapidly Determining the Enantiomeric Excess of Thousands of Samples," *J. Am. Chem. Soc.*, vol. 123, No. 2, pp. 361-362 (2001).

Kramer, S. et al., "Preparation of Protein Gradients through the Controlled Deposition of Protein-Nanoparticle Conjugates onto Functionalized Surfaces," *J. Am. Chem. Soc.*, vol. 126, No. 17, pp. 5388-5395 (2004).

Lam, K. et al., "The 'One-Bead-One Compound' Combinatorial Library Method," *Chemical Reviews*, vol. 97, No. 2, pp. 411-448 (1997).

Lavigne, J. et al., "Sensing a Paradigm Shift in the Field of Molecular Recognition: From Selective to Differential Receptors," *Angew. Chem. Int. Ed.*, vol. 40, pp. 3118-3130 (2001).

Lee, D. et al., "Pairwise Use of Complexity-Generating Reactions in Diversity-Oriented Organic Synthesis," *Organic Letters*, vol. 2, No. 5, pp. 709-712 (2000).

Lehn, J et al., "Dynamic Combinatorial Chemistry," *Science*, vol. 291, pp. 2331-2332 (Mar. 23, 2001).

Leigh, D., "Summing Up Ligand Binding Interactions," *Chemistry & Biology*, vol. 10, pp. 1143-1144 (Dec. 2003).

Li, S. et al., "Artificial Receptor-Facilitated Solid-Phase Microextraction of Barbiturates," *Anal. Chem.*, vol. 71, No. 11, pp. 2146-2151 (Jun. 1, 1999).

Lindsley, C. et al., "Solid-Phase Biomimetic Synthesis of Carpanone-like Molecules," *J. Am. Chem. Soc.*, vol. 122, No. 2, pp. 422-423 (2000).

Linton, B. et al., "Host-guest chemistry: combinatorial receptors," *Current Opinion in Chemical Biology*, vol. 3, pp. 307-312 (1999).

MacBeath, G. et al., "Printing Small Molecules as Microarrays and Detecting Protein-Ligand Interactions en Masse," *J. Am. Chem. Soc.*, vol. 121, No. 34, pp. 7967-7968 (1999).

MacBeath, G. et al., "Printing Proteins as Microarrays for High-Throughput Function Determination," *Science*, vol. 289, pp. 1760-1763 (Sep. 8, 2000).

Malin, R. et al., "Identification of Technetium-99m Binding Peptides Using Combinatorial Cellulose-Bound Peptide Libraries," *J. Am. Chem. Soc.*, vol. 117, No. 47, pp. 11821-11822 (1995).

Maly, D. et al., "Combinatorial Target-Guided Ligand Assembly: Identification of Potent Subtype-Selective c-Src Inhibitors," *PNAS*, vol. 97, No. 6, pp. 2419-2424 (Mar. 14, 2000).

McDonald, D. et al., "Application of Free Energy Perturbation Calculations to the Enantioselective Binding of Peptides to $C_3$-Symmetric Synthetic Receptors," *J. Am. Chem. Soc.*, vol. 118, No. 8, pp. 2073-2077 (1996).

Moore, J. et al., "'Masterpiece' Copolymer Sequences by Targeted Equilibruim-Shifting," *Organic Letters*, vol. 2, No. 7, pp. 915-918 (2000).

Mosbach, K. et al., "Generation of New Enzyme Inhibitors Using Imprinted Binding Sites: The Anti-Idiotypic Approach, a Step Toward the Next Generation of Molecular Imprinting," *J. Am. Chem. Soc.*, vol. 123, No. 49, pp. 12420-12421 (2001).

Noji, H. et al. "Direct observation of the rotation of $F_1$-ATPase," *Nature*, vol. 386, pp. 299-302 (Mar. 20, 1997).

Ogoshi, H. et al., "Novel Approaches to Molecular Recognition Using Porphyrins," *Current Opinion in Chemical Biology*, vol. 3, pp. 736-739 (1999).

Olivos, H. et al., "Microwave-Assisted Solid-Phase Synthesis of Peptoids," *Organic Letters*, vol. 4, No. 23, pp. 4057-4059 (2002).

Olivos, H. et al., "Quantum Dots as a Visual Aid for Screening Bead-Bound Combinatorial Libraries," Center for Biomedical inventions and the Departments of Internal Medicine and Molecular Biology, University of Texas Southwestern Medical Center, Dallas, Texas, pp. 1-21 (2003).

Opatz, T. et al., "A Selectively Deprotectable Triazacyclophane Scaffold for the Construction of Artificial Receptors," *Organic Letters*, vol. 3, No. 22, pp. 3499-3502 (2001).

Oprea, T. et al., "Chemography: The Art of Navigating in Chemical Space," *J. Comb. Chem.*, vol. 3, No. 2, pp. 157-166 (2001).

Park, H. et al., "Protein Surface Recognition by Synthetic Receptors: A Route to Novel Submicromolar Inhibitors for α-Chymotrypsin," *J. Am. Chem. Soc.*, vol. 121, No. 1, pp. 8-13 (1999).

Park, H. et al., "Modulation of protein-protein interactions by synthetic receptors: Design of molecules that disrupt serine protease-proteinaceous inhibitor interaction," *PNAS*, vol. 99, No. 8, pp. 5105-5109 (Apr. 16, 2002).

Pattarawarapan, M. et al., "A Linker Scaffold to Present Dimers of Pharmacophores Prepared by Solid-Phase Syntheses," *Angew. Chem. Int. Ed.*, vol. 39, No. 23, pp. 4299-4301 (2000).

Peczuh, M. et al., "Peptide and Protein Recognition by Designed Molecules," *Chem. Rev.*, vol. 100, No. 7, pp. 2479-2493 (2000).

Pickens, J. et al., "Anchor-Based Design of Improved Cholera Toxin and *E. coli* Heat-Labile Enterotoxin Receptor Binding Antagonists that Display Multiple Binding Modes," *Chemistry & Biology*, vol. 9, pp. 215-224 (Feb. 2002).
Pirrung, M., "Spatially Addressable Combinatorial Libraries," *Chemical Reviews*, vol. 97, No. 2, pp. 473-488 (1997).
Quaglia, M. et al., "Target Analogue Imprinted Polymers with Affinity for Folic Acid and Related Compounds," *J. Am. Chem. Soc.*, vol. 123, No. 10, pp. 2146-2154 (2001).
Ramström, O. et al., "Synthesis and Catalysis by Molecularly Imprinted Materials," *Current Opinion in Chemical Biology*, vol. 3, pp. 759-764 (1999).
Rodriguez, M. et al., "An Oriented Peptide Array Library (OPAL) Strategy to Study Protein-Protein Interactions," *The Journal of Biological Chemistry*, vol. 279, No. 10, pp. 8802-8807 (Mar. 5, 2004).
Sadik, O. et al., "Differential Impedance Spectroscopy for Monitoring Protein Immobilization and Antibody-Antigen Reactions," *Anal. Chem.*, vol. 74, No. 13, pp. 3142-3150 (Jul. 1, 2002).
Sasaki, D., "Control of Membrane Structure and Organization Through Chemical Recognition," *Cell Biochemistry and Biophysics*, vol. 39, pp. 145-161 (2003).
Sasmal, S. et al., "Facile Purification of Rare Cucurbiturils by Affinity Chromatography," *Organic Letters*, vol. 6, No. 8, pp. 1225-1228 (2004).
Shao, Y. et al., "Sequence-Selective Receptors of Peptides, A Simple Molecular Design for Construction of Large Combinatorial Libraries of Receptors," *J. Org. Chem.* vol. 61, No. 18, pp. 6086-6087 (1996).
Shellenberger, K. et al., "Effect of Molecular Scale Roughness of Glass Beads on Colloidal and Bacterial Deposition," *Environ. Sci. Technol.*, vol. 36, No. 2, pp. 184-189 (2002).
Shinoda, S. et al., "Ester-Armed Cyclens Having Quadruplicated Helical Geometry: Remarkably Stable and Selective Encapsulation of $Na^+$ Ion," *J. Org. Chem.*, vol. 66, No. 18, pp. 6104-6108 (2001).
Song, X. et al., "Direct, Ultrasensitive, and Selective Optical Detection of Protein Toxins Using Multivalent Interactions," *Anal. Chem.*, vol. 71, No. 11, pp. 2097-2107 (Jun. 1, 1999).
Srinivasan, N. et al., "Combinatorial approaches to synthetic receptors," *Current Opinion in Chemical Biology*, vol. 8, pp. 305-310 (2004).
Sternson, S. et al., "Split-Pool Synthesis of 1,3-Dioxanes Leading to Arrayed Stock Solutions of Single Compounds Sufficient for Multiple Phenotypic and Protein-Binding Assays," *J. Am. Chem. Soc.*, vol. 123, No. 8, pp. 1740-1747 (2001).
Tomalia, D., "Birth of a New Macromolecular Architecture: Dendrimers as Quantized Building Blocks for Nanoscale Synthetic Organic Chemistry," *Aldrichimica ACTA*, vol. 37, No. 2, pp. 39-57 (2004).
Wang, Y. et al., "Identification of Chiral Selectors from a 200-Member Parallel Combinatorial Library," *Anal. Chem.*, vol. 72, No. 21, pp. 5459-5465 (Nov. 1, 2000).
Way, J., "Covalent Modification as a Strategy to Block Protein-Protein Interactions with Small-Molecule Drugs," *Current Opinion in Chemical Biology*, vol. 4, pp. 40-46 (2000).
Winssinger, N. et al., "From Split-Pool Libraries to Spatially Addressable Microarrays and its Application to Functional Proteomic Profiling," *Angew. Chem. Int. Ed.*, vol. 40, No. 17, pp. 3152-3155 (2001).
Wolfbeis, O., "Fiber-Optic Chemical Sensors and Biosensors," *Anal. Chem.*, vol. 76, No. 12, pp. 3269-3283 (Jun. 15, 2004).
Worsley, K. et al., "Long-Range Periodicity in Carbon Nanotube Sidewall Functionalization," *Nano Letters*, vol. 4, No. 8, pp. 1541-1546 (2004).
Wu, Z. et at., "Transparent, Conductive Carbon Nanotube Films," *Science*, vol. 305, pp. 1273-1276 (Aug. 27, 2004).
Xu, R. et al., "Combinatorial Library Approach for the Identification of Synthetic Receptors Targeting Vancomycin-Resistant Bacteria," *J. Am. Chem. Soc.*, vol. 121, No. 20, pp. 4898-4899 (1999).
Yan, B. et al., "Crucial Factors Regulating Site Interactions in Resin Supports Determined by Single Bead IR," *J. Org. Chem.*, vol. 63, No. 1, pp. 55-58 (1998).
Yurke, B. et al., "A DNA-fuelled molecular machine made of DNA," *Nature*, vol. 406, pp. 605-608 (Aug. 10, 2000).
Zhang, Z. et al., "Self-Assembly of Patchy Particles," *Nano Letters*, vol. 4, No. 8, pp. 1407-1413 (2004).
Zhu, H. et al., "Protein Arrays and Microarrays," *Current Opinion in Chemical Biology*, vol. 5, pp. 40-45 (2001).
Zhuravlev, N. et al., "Surface Coverages of Bonded-Phase Ligands on Silica: A Computational Study," *Anal. Chem.*, vol. 73, No. 16, pp. 4006-4011 (Aug. 15, 2001).
Zimmerman, S. et al., "Model Systems," *Current Opinion in Chemical Biology*, vol. 3, pp. 711-713 (1999).
International Search Report mailed May 4, 2006.
Angers et al., Proc. Natl. Acad. Sci. USA (Mar. 28, 2000), vol. 97(7), pp. 3684-3689.
European Search Report, Application No. 03709250.9 dated May 7, 2007.
Iorio et al., "Highly Sequence Selective Nonmacrocyclic Two-armed Receptors for Peptides," Bioorganic & Medicinal Chemistry Letters, Oxford, GB, vol. 9, No. 15, Aug. 2, 1999, pp. 2145-2150.
Iorio et al., "Sequence-Selective Peptide Detection by Small Synthetic Chemosensors Selected from an Encoded Combinatorial Chemosensor Library," Bioorganic & Medicinal Chemistry Letters, Oxford, GB, vol. 11, No. 13, Jul. 9, 2001, pp. 1635-1638.
Nestler et al., "Combinatorial Libraries: Studies in Molecular Recognition," Combinatorial Chemistry and High Throughput Screening, Hilversum, NL, vol. 1, No. 3, Oct. 1998, pp. 113-126.
Still, "Discovery of Sequence-selective Peptide Binding by Synthetic Receptors Using Encoded Combinatorial Libraries," Accounts of Chemical Research, ACS, Washington, DC, US, vol. 29, 1996, pp. 155-163.
U.S. Appl. No. 10/244,727 Office Action Jan. 25, 2006.
U.S. Appl. No. 10/244,727 Office Action Feb. 8, 2006.
U.S. Appl. No. 10/244,727 Office Action Feb. 12, 2007.
U.S. Appl. No. 10/244,727 Office Action May 17, 2005.
U.S. Appl. No. 10/244,727 Office Action May 17, 2007.
U.S. Appl. No. 10/244,727 Office Action Aug. 10, 2005.
U.S. Appl. No. 10/244,727 Office Action Aug. 11, 2006.
U.S. Appl. No. 10/244,727 Office Action Dec. 29, 2006.
U.S. Appl. No. 10/703,660 Office Action Mar. 8, 2007.
U.S. Appl. No. 10/703,660 Office Action Jun. 22, 2006.
U.S. Appl. No. 10/703,779 Office Action Mar. 12, 2007.
U.S. Appl. No. 10/703,779 Office Action Jun. 29, 2006.
U.S. Appl. No. 10/703,876 Office Action Mar. 2, 2007.
U.S. Appl. No. 10/703,876 Office Action Jun. 29, 2006.
U.S. Appl. No. 10/706,505 Office Action Feb. 15, 2007.
U.S. Appl. No. 10/706,505 Office Action Jun. 29, 2006.
U.S. Appl. No. 10/706,573 Office Action Jan. 31, 2007.
U.S. Appl. No. 10/706,573 Office Action Jun. 30, 2006.
U.S. Appl. No. 10/727,059 Office Action Oct. 5, 2006.
U.S. Appl. No. 10/813,568 Office Action Feb. 15, 2007.
U.S. Appl. No. 10/813,568 Office Action Oct. 5, 2006.
U.S. Appl. No. 10/813,568 Office Action Jul. 27, 2007.
U.S. Appl. No. 10/813,612 Office Action Feb. 15, 2007.
U.S. Appl. No. 10/813,612 Office Action Oct. 6, 2006.
U.S. Appl. No. 10/813,612 Office Action Aug. 7, 2007.
U.S. Appl. No. 10/934,193 Office Action Jul. 27, 2007.
U.S. Appl. No. 10/934,865 Office Action Aug. 2, 2007.
U.S. Appl. No. 10/706,573 Office Action Jul. 28, 2008.
International Search Report and Written Opinion mailed May 15, 2009.
Sila et al., "Topological Templates as Tool in Molecular Recognition and Peptide Mimicry: Synthesis of a TASK Library," Journal of Molecular Recognition, vol. 8, 2-34 (1995).
U.S. Appl. No. 10/244,727 Notice of Allowance Jan. 9, 2009.
U.S. Appl. No. 10/703,779 Office Action dated Aug. 5, 2009.
U.S. Appl. No. 10/703,779 Office Action dated Feb. 19, 2010.
U.S. Appl. No. 10/703,876 Office Action Oct. 20, 2008.
U.S. Appl. No. 10/703,876 Office Action dated Jul. 23, 2009.
U.S. Appl. No. 10/703,876 Office Action dated Apr. 1, 2010.
U.S. Appl. No. 10/706,573 Office Action dated Sep. 2, 2009.
U.S. Appl. No. 10/813,568 Office Action dated Jul. 22, 2009.
U.S. Appl. No. 10/813,612 Office Action dated Jul. 8, 2009.
U.S. Appl. No. 10/813,612 Office Action dated Mar. 22, 2010.
U.S. Appl. No. 10/934,193 Notice of Allowance Oct. 6, 2008.
U.S. Appl. No. 10/934,865 Office Action Apr. 8, 2009.
U.S. Appl. No. 10/934,865 Office Action dated Jan. 22, 2010.
U.S. Appl. No. 10/934,879 Office Action Oct. 16, 2008.

U.S. Appl. No. 10/934,879 Office Action dated Apr. 5, 2010.
U.S. Appl. No. 10/934,977 Office Action dated Aug. 21, 2009.
U.S. Appl. No. 10/934,977 Office Action dated May 26, 2010.
U.S. Appl. No. 11/004,593 Office Action dated Sep. 15, 2009.
U.S. Appl. No. 11/217,384 Office Action dated Aug. 17, 2009.
U.S. Appl. No. 11/219,515 Notice of Allowance Jan. 9, 2009.
U.S. Appl. No. 11/223,463 Office Action Mar. 11, 2009.
U.S. Appl. No. 11/223,463 Office Action dated May 11, 2010.
U.S. Appl. No. 11/709,696 Office Action Oct. 16, 2008.
U.S. Appl. No. 11/709,696 Office Action dated Apr. 6, 2010.

* cited by examiner

FIG. 1
2D TOP VIEW
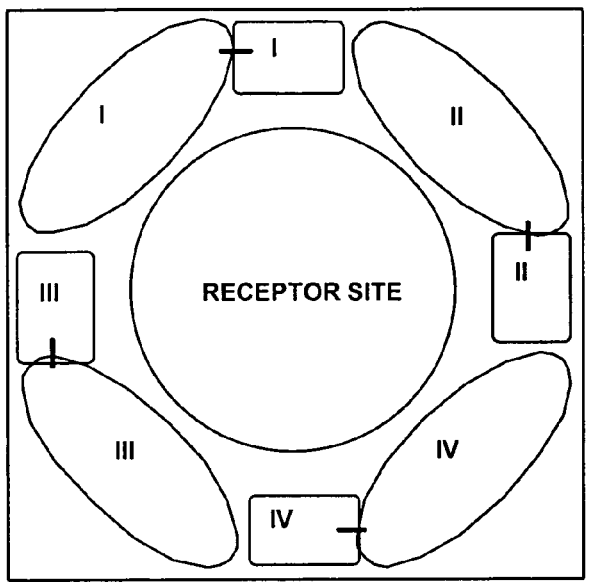
2D SIDE VIEW
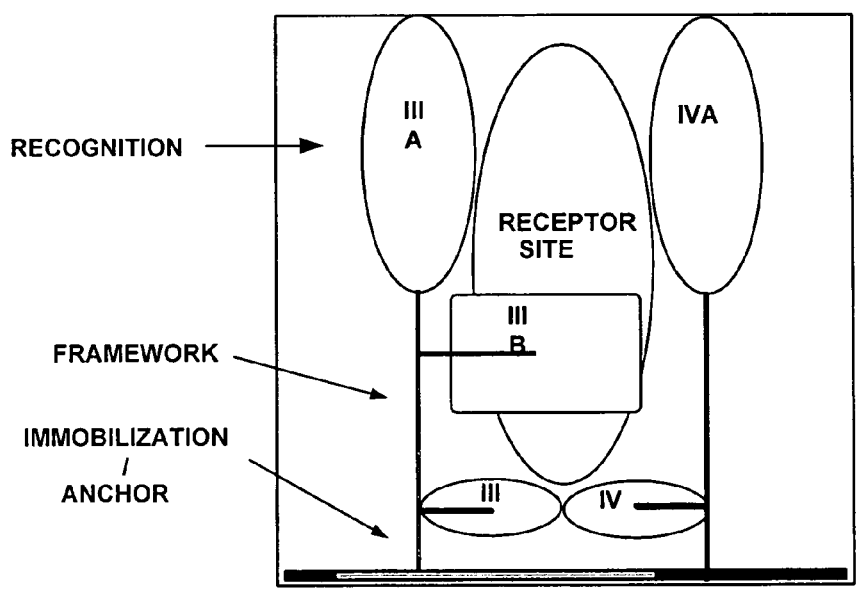
3D FRONT VIEW
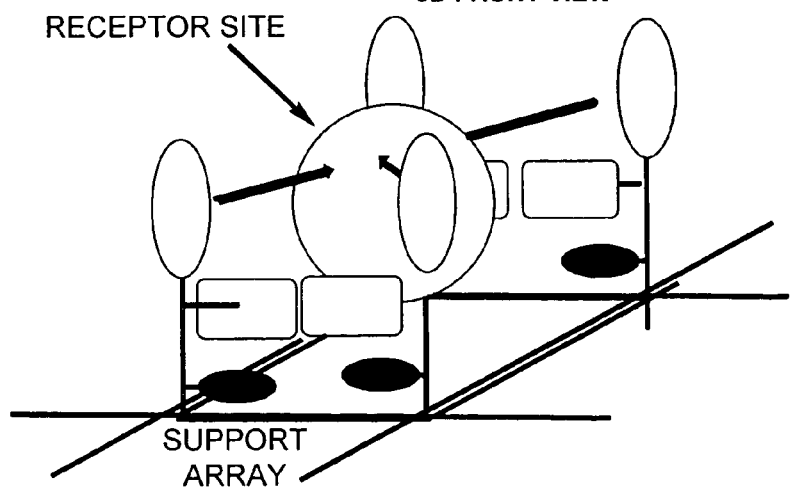

Origin  = 28, 140 pixels
          (0.28, 1.4 mm)
Size    = 2032 x 1888 pixels
          (20.32 x 18.88 mm)
Scaling = 10 μm/pixel
Scanner = GenePix 4100A 01 [92896]
No averaging.
PMT Gain = 940
Laser Power = 100%
Normalization Factor = 1
Focus Position = 0

Origin = 4, 0 pixels
(0.04, 0 mm)
Size = 2180 x 1368 pixels
(21.8 x 13.68 mm)
Scaling = 10µm/pixel
Scanner = GenePix 4100A 01 [92896]
No averaging.
PMT Gain = 600
Laser Power = 100%
Normalization Factor = 1
Filter = 670DF40
Focus Position = 0

Origin   = 4, 0 pixels
         (0.04, 0 mm)
Size    = 2180 x 1068 pixels
         (21.8 x 10.68 mm)
Scaling = 10µm/pixel
Scanner = GenePix 4100A 01 [92896]
No averaging.
PMT Gain = 600
Laser Power = 100%
Normalization Factor = 1
Filter = 670DF40
Focus Position = 0

Origin = 4, 0 pixels
(0.04, 0 mm)
Size = 2180 x 1368 pixels
(21.8 x 13.68 mm)
Scaling = 10μm/pixel
Scanner = GenePix 4100A 01 [92896]
No averaging.
PMT Gain = 600
Laser Power = 100%
Normalization Factor = 1
Filter = 670DF40
Focus Position = 0

Origin   = 4, 0 pixels
         (0.04, 0 mm)
Size     = 2180 x 1368 pixels
         (21.8 x 13.68 mm)
Scaling  = 10μm/pixel
Scanner = GenePix 4100A 01 [92896]
No averaging.
PMT Gain = 560
Laser Power = 100%
Normalization Factor = 1
Filter = 670DF40
Focus Position = 0

FIG. 36

CARA DIRECT vs. DYNAMIC - Incubation Temperature
(CHOL/(AA/SA), N9n2, PMT 510)

Incubation Temperature / Fluorescence Units

COMBINATORIAL ARTIFICIAL RECEPTORS INCLUDING TETHER BUILDING BLOCKS ON SCAFFOLDS

CROSS REFERENCE TO RELATED APPLICATIONS

This application claims priority to U.S. Provisional Patent Application Nos. 60/609,160, filed Sep. 11, 2004, entitled "ARTIFICIAL RECEPTORS, BUILDING BLOCKS, AND METHODS", 60/612,666, filed Sep. 23, 2004, entitled "ARTIFICIAL RECEPTORS, BUILDING BLOCKS, AND METHODS", 60/626,770, filed Nov. 10, 2004, entitled "ARTIFICIAL RECEPTORS, BUILDING BLOCKS, AND METHODS", 60/645,582, filed Jan. 19, 2005, entitled "ARTIFICIAL RECEPTORS, BUILDING BLOCKS, AND METHODS", 60/649,729, filed Feb. 3, 2005, entitled "ARTIFICIAL RECEPTORS, BUILDING BLOCKS, AND METHODS", 60/607,438, filed Sep. 3, 2004, entitled "COMBINATORIAL ARTIFICIAL RECEPTORS INCLUDING TETHER BUILDING BLOCKS ON SCAFFOLDS", 60/607,458, filed Sep. 3, 2004, entitled "COMBINATORIAL ARTIFICIAL RECEPTORS INCLUDING TETHER BUILDING BLOCKS ON SCAFFOLDS", 60/608,557, filed Sep. 10, 2004, entitled "COMBINATORIAL ARTIFICIAL RECEPTORS INCLUDING TETHER BUILDING BLOCKS ON SCAFFOLDS", 60/607,457, filed Sep. 3, 2004, entitled "SCAFFOLD-BASED ARTIFICIAL RECEPTORS AND METHODS", and 60/608,654, filed Sep. 10, 2004, entitled "SCAFFOLD-BASED ARTIFICIAL RECEPTORS AND METHODS".

Each of the listed applications is incorporated herein by reference.

FIELD OF THE INVENTION

The present invention relates to artificial receptors, arrays or microarrays of artificial receptors or candidate artificial receptors, methods of and compositions for making them, and methods of using them. Each artificial receptor includes a plurality of building block compounds. In an embodiment, at least one of the building blocks includes a tether moiety. The tether can provide spacing or distance between the recognition element and the scaffold to which the building block is immobilized. A tether moiety can have any of a variety of characteristics or properties including flexibility, rigidity or stiffness, ability to bond to another tether moiety, and the like. In certain embodiments, combinations of 2, 3, 4, or 5 distinct building block molecules immobilized near one another on a scaffold provide molecular structures that can be employed in the present methods.

BACKGROUND

The preparation of artificial receptors that bind ligands like proteins, peptides, carbohydrates, microbes, pollutants, pharmaceuticals, and the like with high sensitivity and specificity is an active area of research. None of the conventional approaches has been particularly successful; achieving only modest sensitivity and specificity mainly due to low binding affinity.

Antibodies, enzymes, and natural receptors generally have binding constants in the $10^8$-$10^{12}$ range, which results in both nanomolar sensitivity and targeted specificity. By contrast, conventional artificial receptors typically have binding constants of about $10^3$ to $10^5$, with the predictable result of millimolar sensitivity and limited specificity.

Several conventional approaches are being pursued in attempts to achieve highly sensitive and specific artificial receptors. These approaches include, for example, affinity isolation, molecular imprinting, and rational and/or combinatorial design and synthesis of synthetic or semi-synthetic receptors.

Such rational or combinatorial approaches have been limited by the relatively small number of receptors which are evaluated and/or by their reliance on a design strategy which focuses on only one building block, the homogeneous design strategy. Common combinatorial approaches form microarrays that include 10,000 or 100,000 distinct spots on a standard microscope slide. However, such conventional methods for combinatorial synthesis provide a single molecule per spot. Employing a single building block in each spot provides only a single possible receptor per spot. Synthesis of thousands of building blocks would be required to make thousands of possible receptors.

Further, these conventional approaches are hampered by the currently limited understanding of the principles which lead to efficient binding and the large number of possible structures for receptors, which makes such an approach problematic.

There remains a need for methods for detecting test ligands in unknown samples and for detecting compounds that disrupt one or more binding interactions.

SUMMARY

The present invention relates to artificial receptors, or candidate artificial receptors, methods of and compositions for making them, and methods of using them. Each artificial receptor includes a plurality of building block compounds. The plurality of the building blocks are coupled to a scaffold. In an embodiment, the scaffold is not coupled to a solid support.

In an embodiment, at least one of the building blocks includes a tether moiety. The tether can provide spacing or distance between the recognition element and the to which the building block is immobilized. A tether moiety can have any of a variety of characteristics or properties including flexibility, rigidity or stiffness, ability to bond to another tether moiety, and the like.

The present invention includes a method of making a scaffold artificial receptor including building blocks coupled to scaffolds. This method includes forming a plurality of reaction sites on a scaffold and coupling a building block to each reaction site. The invention includes artificial receptors and compositions. The compositions include a scaffold and a plurality of building blocks including a tether and immobilized on a surface.

The present invention includes a method of making an artificial receptor. This method includes coupling a plurality of building blocks on a scaffold. The region includes a plurality of building blocks, at least one of the building blocks including a tether moiety. The method includes immobilizing building blocks on the scaffold.

BRIEF DESCRIPTION OF THE FIGURES

FIG. 1 schematically illustrates two and three dimensional representations of an embodiment of a molecular configuration of 4 building blocks, each building block including a recognition element, a framework, and a linker coupled to a support (immobilization/anchor).

FIG. 36 schematically illustrates the data presented in FIG. 34 (lines marked A) and the data presented in FIG. 35 (lines marked B).

DETAILED DESCRIPTION

Definitions

Figure 2:
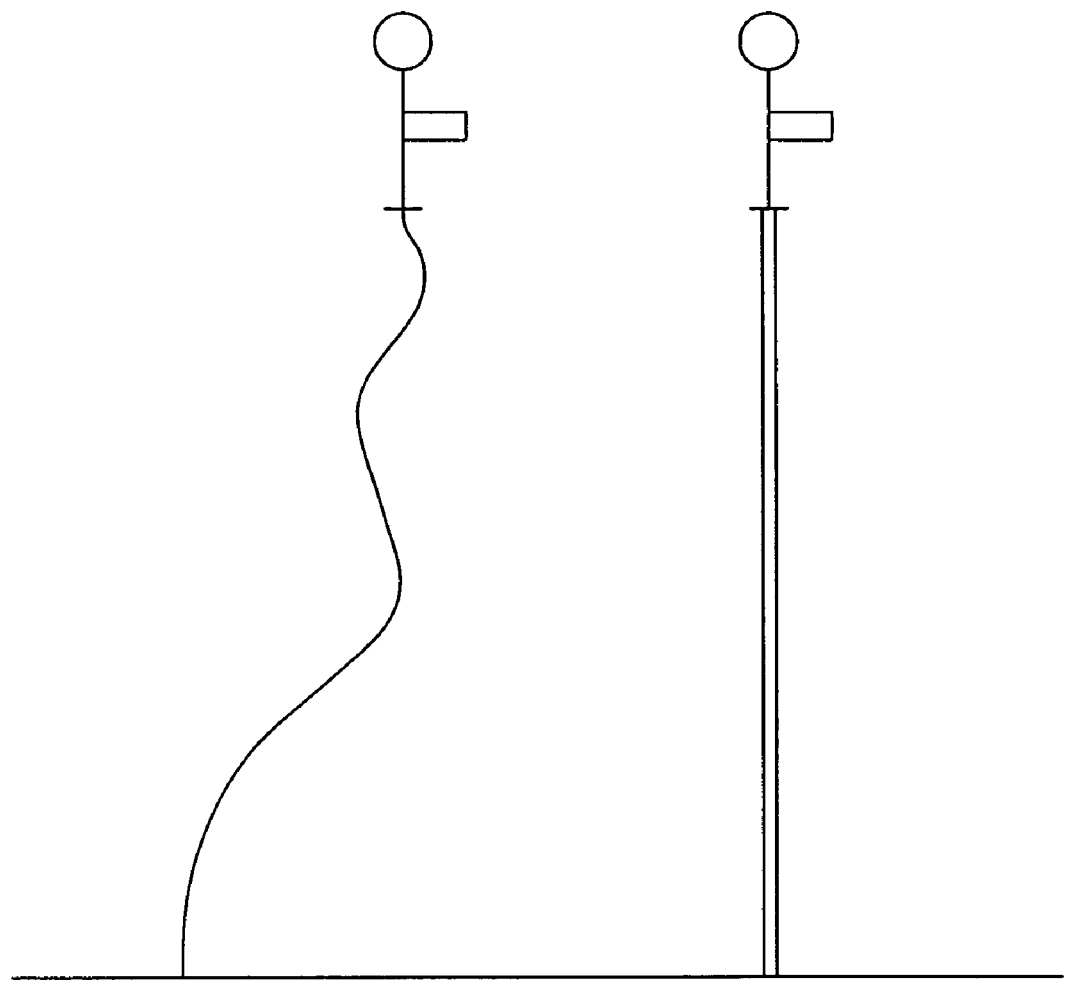
FIG. 2 schematically illustrates an embodiment of a building block including a flexible tether (left) and a building block including a rigid tether (right).

As used herein, the term "peptide" refers to a compound including two or more amino acid residues joined by amide bond(s).

As used herein, the terms "polypeptide" and "protein" refer to a peptide including more than about 20 amino acid residues connected by peptide linkages.

As used herein, the term "proteome" refers to the expression profile of the proteins of an organism, tissue, organ, or cell. The proteome can be specific to a particular status (e.g., development, health, etc.) of the organism, tissue, organ, or cell.

As used herein, the term "support" refers to a solid support that is, typically, macroscopic.

As used herein, the term "scaffold" refers to a microscale, or nanoscale, or molecular scale structure, having a plurality of reactive sites for coupling a plurality of building blocks.

As used herein, the term "soluble" refers to the ability to dissolve in solution. A soluble scaffold or soluble scaffold artificial receptor blends uniformly in liquid. The soluble scaffold or soluble scaffold artificial receptor may be either liquid or solid.

Reversibly immobilizing building blocks on a scaffold couples the building blocks to the scaffold through a mechanism that allows the building blocks to be uncoupled from the scaffold without destroying or unacceptably degrading the building block or the scaffold. That is, immobilization can be reversed without destroying or unacceptably degrading the building block or the scaffold. In an embodiment, immobilization can be reversed with only negligible or ineffective levels of degradation of the building block or the scaffold. Reversible immobilization can employ readily reversible covalent bonding or noncovalent interactions. Suitable noncovalent interactions include interactions between ions, hydrogen bonding, van der Waals interactions, and the like. Readily reversible covalent bonding refers to covalent bonds that can be formed and broken under conditions that do not destroy or unacceptably degrade the building block or the scaffold.

A combination of building blocks immobilized on, for example, a scaffold can be a candidate artificial receptor, a lead artificial receptor, or a working artificial receptor. A candidate artificial receptor can become a lead artificial receptor, which can become a working artificial receptor.

As used herein the phrase "candidate artificial receptor" refers to an immobilized combination of building blocks that can be tested to determine whether or not a particular test ligand binds to that combination. In an embodiment, the combination includes one or more reversibly immobilized building blocks. In an embodiment, the candidate artificial receptor can be a heterogeneous building block spot on a slide or a plurality of building blocks coated on a tube or well.

As used herein the phrase "lead artificial receptor" refers to an immobilized combination of building blocks that binds a test ligand at a predetermined concentration of test ligand, for example at 10, 1, 0.1, or 0.01 µg/ml, or at 1, 0.1, or 0.01 ng/ml. In an embodiment, the combination includes one or more reversibly immobilized building blocks. In an embodiment, the lead artificial receptor can be a heterogeneous building block spot on a slide or a plurality of building blocks coated on a tube or well.

As used herein the phrase "working artificial receptor" refers to a combination of building blocks that binds a test ligand with a selectivity and/or sensitivity effective for categorizing or identifying the test ligand. That is, binding to that combination of building blocks describes the test ligand as belonging to a category of test ligands or as being a particular test ligand. A working artificial receptor can, for example, bind the ligand at a concentration of, for example, 100, 10, 1, 0.1, 0.01, or 0.001 ng/ml. In an embodiment, the combination includes one or more reversibly immobilized building blocks. In an embodiment, the working artificial receptor can be a heterogeneous building block spot on a slide or a plurality of building blocks coated on a tube, well, slide, or other support or on a scaffold.

As used herein the phrase "working artificial receptor complex" refers to a plurality of artificial receptors, each a combination of building blocks, that binds a test ligand with a pattern of selectivity and/or sensitivity effective for categorizing or identifying the test ligand. That is, binding to the several receptors of the complex describes the test ligand as belonging to a category of test ligands or as being a particular test ligand. The individual receptors in the complex can each bind the ligand at different concentrations or with different affinities. For example, the individual receptors in the complex each bind the ligand at concentrations of 100, 10, 1, 0.1, 0.01 or 0.001 ng/ml. In an embodiment, the combination includes one or more reversibly immobilized building blocks. In an embodiment, the working artificial receptor complex can be a plurality of heterogeneous building block spots or regions on a slide; a plurality of wells, each coated with a different combination of building blocks; or a plurality of tubes, each coated with a different combination of building blocks.

As used herein, the phrase "significant number of candidate artificial receptors" refers to sufficient candidate artificial receptors to provide an opportunity to find a working artificial receptor, working artificial receptor complex, or lead artificial receptor. As few as about 100 to about 200 candidate artificial receptors can be a significant number for finding working artificial receptor complexes suitable for distinguishing two proteins (e.g., cholera toxin and phycoerythrin). In other embodiments, a significant number of candidate artificial receptors can include about 1,000 candidate artificial receptors, about 10,000 candidate artificial receptors, about 100,000 candidate artificial receptors, or more.

Although not limiting to the present invention, it is believed that the significant number of candidate artificial receptors required to provide an opportunity to find a working artificial receptor may be larger than the significant number required to find a working artificial receptor complex. Although not limiting to the present invention, it is believed that the significant number of candidate artificial receptors required to provide an opportunity to find a lead artificial receptor may be larger than the significant number required to find a working artificial receptor. Although not limiting to the present invention, it is believed that the significant number of candidate artificial receptors required to provide an opportunity to find a working artificial receptor for a test ligand with few features may be more than for a test ligand with many features.

As used herein, the term "building block" refers to a molecular component of an artificial receptor including portions that can be envisioned as or that include: one or more tethers, one or more linkers, one or more frameworks, and one or more recognition elements. In an embodiment, the building block includes: a tether, a linker, a framework, and one or more recognition elements. In an embodiment, the linker includes a moiety suitable for reversibly immobilizing the building block on a support. The building block interacts with the ligand.

As used herein, the term "linker" refers to a portion of or functional group on a building block that can be employed to or that does (e.g., reversibly) couple the building block to a scaffold, for example, through covalent link, ionic interaction, electrostatic interaction, or hydrophobic interaction.

As used herein, the term "framework" refers to a portion of a building block including the linker or to which the linker is coupled and to which one or more recognition elements are coupled.

As used herein, the term "recognition element" refers to a portion of a building block coupled to the framework but not covalently coupled to the scaffold. Although not limiting to the present invention, the recognition element can provide or form one or more groups, surfaces, or spaces for interacting with the ligand.

As used herein, the phrase "plurality of building blocks" refers to two or more building blocks of different structure in a mixture, in a kit, or on scaffold. Each building block has a particular structure, and use of building blocks in the plural, or of a plurality of building blocks, refers to more than one of these particular structures. Building blocks or plurality of building blocks does not refer to a plurality of molecules each having the same structure.

As used herein, the phrase "combination of building blocks" refers to a plurality of building blocks that together are in a spot, region, or a candidate, lead, or working artificial receptor. A combination of building blocks can be a subset of a set of building blocks. For example, a combination of building blocks can be one of the possible combinations of 2, 3, 4, 5, or 6 building blocks from a set of N (e.g., N=10–200) building blocks.

As used herein, the phrases "homogenous immobilized building block" and "homogenous immobilized building blocks" refer to a scaffold having immobilized on or within it a single building block.

As used herein, the phrase "activated building block" refers to a building block activated to make it ready to form a covalent bond to a functional group, for example, on a scaffold. A building block including a carboxyl group can be converted to a building block including an activated ester group, which is an activated building block. An activated building block including an activated ester group can react, for example, with an amine to form a covalent bond.

As used herein, the term "naïve" used with respect to one or more building blocks refers to a building block that has not previously been determined or known to bind to a test ligand of interest. For example, the recognition element(s) on a naïve building block has not previously been determined or known to bind to a test ligand of interest. A building block that is or includes a known ligand (e.g., GM1) for a particular protein (test ligand) of interest (e.g., cholera toxin) is not naïve with respect to that protein (test ligand).

As used herein, the term "immobilized" used with respect to building blocks coupled to a scaffold refers to building blocks being stably oriented on the scaffold so that they do not migrate on the scaffold or release from the scaffold. Building blocks can be immobilized by covalent coupling, by ionic interactions, by electrostatic interactions, such as ion pairing, or by hydrophobic interactions, such as van der Waals interactions.

As used herein a "region" of a scaffold, tube, well, or surface refers to a contiguous portion of the scaffold, tube, well, or surface. Building blocks coupled to a region can refer to building blocks in proximity to one another in that region.

As used herein, a "bulky" group on a molecule is larger than a moiety including 7 or 8 carbon atoms.

As used herein, a "small" group on a molecule is hydrogen, methyl, or another group smaller than a moiety including 4 carbon atoms.

As used herein, the term "lawn" refers to a layer, spot, or region of functional groups on a scaffold, for example, at a density sufficient to place coupled building blocks in proximity to one another. The functional groups can include groups capable of forming covalent, ionic, electrostatic, or hydrophobic interactions with building blocks.

As used herein, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{12}$ for straight chain, $C_1$-$C_6$ for branched chain). Likewise, cycloalkyls can have from 3-10 carbon atoms in their ring structure, for example, 5, 6 or 7 carbons in the ring structure.

The term "alkyl" as used herein refers to both "unsubstituted alkyls" and "substituted alkyls", the latter of which refers to alkyl moieties having substituents replacing a hydrogen on one or more carbons of the hydrocarbon backbone, Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aryl alkyl, or an aromatic or heteroaromatic moiety. The moieties substituted on the hydrocarbon chain can themselves be substituted, if appropriate. For example, the substituents of a substituted alkyl can include substituted and unsubstituted forms of the groups listed above.

The phrase "aryl alkyl", as used herein, refers to an alkyl group substituted with an aryl group (e.g., an aromatic or heteroaromatic group).

As used herein, the terms "alkenyl" and "alkynyl" refer to unsaturated aliphatic groups analogous in length and optional substitution to the alkyls groups described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents such as those described above for alkyl groups. The term "aryl" also includes polycyclic ring systems having two or more cyclic rings in which two or more carbons are common to two adjoining rings (the rings are "fused rings") wherein at least one of the rings is aromatic, e.g., the other cyclic ring(s) can be cycloalkyls, cycloalkenyls, cycloalkynyls, aryls and/or heterocyclyls.

As used herein, the terms "heterocycle" or "heterocyclic group" refer to 3- to 12-membered ring structures, e.g., 3- to 7-membered rings, whose ring structures include one to four heteroatoms. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents such as those described for alkyl groups.

As used herein, the term "heteroatom" as used herein means an atom of any element other than carbon or hydrogen, such as nitrogen, oxygen, sulfur and phosphorous.

Overview of the Adaptive Artificial Receptor

The present invention relates to artificial receptors including building blocks, at least one building block comprising a tether, coupled to a scaffold, such as a soluble organic molecule. The present receptors include heterogenous combinations of building block molecules, at least one building block molecule comprising a tether. In certain embodiments, the present artificial receptors include combinations of 2, 3, 4, or 5 distinct building block molecules immobilized in proximity to one another on a scaffold. The present artificial receptors can be employed to detect the receptor's ligand.

An artificial receptor can include a combination of building blocks, at least one building block comprising a tether, immobilized (e.g., reversibly) on a scaffold. An individual artificial receptor can be a heterogeneous plurality of building blocks on a scaffold, at least one building block comprising a tether. The building blocks can be immobilized through any of a variety of interactions, such as covalent, electrostatic, or hydrophobic interactions. For example, the building block and scaffold can each include one or more functional groups or moieties that can form covalent, electrostatic, hydrogen bonding, van der Waals, or like interactions. Artificial receptors, particularly candidate or lead artificial receptors, can be in the form of an array of artificial receptors. An array of artificial receptors can utilize scaffold artificial receptors in solution.

In an embodiment, the artificial receptor of the invention includes a plurality of building blocks coupled to a scaffold, at least one building block comprising a tether. Each immobilized building block molecule can provide one or more "arms" extending from a "framework" and each can include groups that interact with a ligand or with portions of another immobilized building block. FIG. 1 illustrates that combinations of four building blocks, each including a framework with two arms (called "recognition elements"), provides a molecular configuration of building blocks that form a site for binding a ligand. Such a site formed by building blocks such as those exemplified below can bind a small molecule, such as a drug, metabolite, pollutant, or the like, and/or can bind a larger ligand such as a macromolecule or microbe.

In an embodiment, the plurality of building blocks can include or be building blocks of Formula 2 (shown below). An abbreviation for the building block including a linker, a tyrosine framework, and recognition elements AxBy is TyrAxBy. In an embodiment, a candidate artificial receptor can include combinations of building blocks of formula TyrA1B1, TyrA2B2, TyrA2B4, TyrA2B6, TyrA2B8, TyrA3B3, TyrA4B2, TyrA4B4, TyrA4B6, TyrA4B8, TyrA5B5, TyrA6B2, TyrA6B4, TyrA6B6, TyrA6B8, TyrA7B7, TyrA8B2, TyrA8B4, TyrA8B6, or TyrA8B8.

The present artificial receptors utilize scaffolds as support for building blocks, at least one building block comprising a tether. In an embodiment, the artificial receptors are free molecules not coupled with a macroscopic solid support, referred to as scaffold artificial receptors. In an embodiment, the present artificial receptors can include building blocks reversibly immobilized on a scaffold. Reversing immobilization of the building blocks can allow movement of building blocks to a different location on the scaffold, or exchange of building blocks onto and off of the scaffold. For example, the combinations of building blocks can bind a ligand when reversibly coupled to or immobilized on the scaffold. Reversing the coupling or immobilization of the building blocks provides opportunity for rearranging the building blocks, which can improve binding of the ligand. Further, the present invention can allow for adding additional or different building blocks, which can further improve binding of a ligand. In an embodiment, one or more building blocks can include a tether. A tether can provide mobility of the building block without reversible binding.

The combinations of building blocks with a scaffold is represented by the formula: $S-BB_n$, wherein S is a scaffold and $BB_n$ is a number of building blocks. In an embodiment, the value of n can be selected from the group consisting of: 2, 3, 4, 5, 6, or 7.

In an embodiment, the scaffold can be an organic molecule, organometallic molecule, or inorganic molecule. In an embodiment, the scaffold is an organic molecule, organometallic molecule, or inorganic molecule further described by an embodiment below.

In an embodiment, the scaffold is an organic molecule less than or equal to approximately 1 nanometer in diameter, and the building block includes one or more frameworks, one or more linkers, and/or one or more tethers, and one or more recognition elements. In an embodiment, the scaffold is an organic molecule less than or equal to approximately 1 nanometer in diameter, and the building block includes a framework, a tether, a linker, and a recognition element. In an embodiment, the scaffold is an organic molecule less than or equal to approximately 1 nanometer in diameter, and the building block includes a framework, a tether, a linker, and two recognition elements.

In an embodiment, the scaffold is an organic molecule less than or equal to approximately 1 nanometer in diameter, and includes one or more: alkyl, substituted alkyl, cycloalkyl, heterocyclic, substituted heterocyclic, aryl alkyl, aryl, heteroaryl, heteroaryl alkyl, and like moieties; and the building block includes one or more frameworks, one or more linkers, and/or one or more tethers, and one or more recognition elements. In an embodiment, the scaffold is an organic molecule less than or equal to approximately 1 nanometer in diameter, and includes one or more: alkyl, substituted alkyl, cycloalkyl, heterocyclic, substituted heterocyclic, aryl alkyl, aryl, heteroaryl, heteroaryl alkyl, and like moieties; and the building block includes a framework, a tether, a linker, and a recognition element. In an embodiment, the scaffold is an organic molecule less than or equal to approximately 1 nanometer in diameter, and includes one or more: alkyl, substituted alkyl, cycloalkyl, heterocyclic, substituted heterocyclic, aryl alkyl, aryl, heteroaryl, heteroaryl alkyl, and like moieties; and the building block includes a framework, a tether, a linker, and two recognition elements.

In an embodiment, the scaffold is an organic molecule between approximately 1 nanometer and 100 nanometers in diameter, and the building block includes one or more frameworks, one or more linkers, and/or one or more tethers, and one or more recognition elements. In an embodiment, the scaffold is an organic molecule between approximately 1 nanometer and 100 nanometers in diameter, and the building block includes a framework, a tether, a linker, and a recognition element. In an embodiment, the scaffold is an organic molecule is between approximately 1 nanometer and 100 nanometers in diameter, and the building block includes a framework, a tether, a linker, and two recognition elements.

In an embodiment, the scaffold is an organic molecule between approximately 1 nanometer and 100 nanometers in diameter, and includes one or more: alkyl, substituted alkyl, cycloalkyl, heterocyclic, substituted heterocyclic, aryl alkyl, aryl, heteroaryl, heteroaryl alkyl, and like moieties; and the building block includes one or more frameworks, one or more linkers, and/or one or more tethers, and one or more recognition elements. In an embodiment, the scaffold is an organic molecule between approximately 1 nanometer and 100 nanometers in diameter, and includes one or more: alkyl, substituted alkyl, cycloalkyl, heterocyclic, substituted heterocyclic, aryl alkyl, aryl, heteroaryl, heteroaryl alkyl, and like moieties; and the building block includes a framework, a tether, a linker, and a recognition element. In an embodiment, the scaffold is an organic molecule between approximately 1 nanometer and 100 nanometers in diameter, and includes one or more: alkyl, substituted alkyl, cycloalkyl, heterocyclic, substituted heterocyclic, aryl alkyl, aryl, heteroaryl, heteroaryl alkyl, and like moieties; and the building block includes a framework, a tether, a linker, and two recognition elements.

The present invention also relates to a method of making an artificial receptor or a candidate artificial receptor. In an embodiment, this method includes preparing reactive sites on a scaffold, coupling a plurality of building blocks to the reactive sites, thereby immobilizing the building blocks on the scaffold.

The method can include mixing a plurality of building blocks and employing the mixture in coupling at the reactive sites. Coupling building blocks to the scaffolds can employ covalent bonding or noncovalent interactions as described above. In an embodiment, the scaffold can be functionalized with moieties that can engage in covalent bonding or noncovalent interactions. Coupling building blocks to the scaffold results in heterogeneous combinations of building blocks on each scaffold, each of which can be a candidate artificial receptor. The method can apply to immobilizing building blocks onto a scaffold in combinations of 2, 3, 4, 5, 6, 7, or more building blocks.

In an embodiment, the present invention relates to an artificial receptor including a tethered building block. A tethered building block can include one or more recognition elements at an end of the building block. Such a building block can be envisioned as including a framework moiety located at or forming that end of the building block. The recognition elements can be coupled to the framework moiety. Such a building block can also include a tether moiety.

The tether moiety can provide spacing or distance between the recognition element and the scaffold to which the building block is immobilized. A tether moiety can have any of a variety of characteristics or properties including flexibility, rigidity or stiffness, ability to bond to another tether moiety, and the like. The tether moiety can include the linker. The framework moiety be envisioned as forming all or part of the tether moiety. FIG. 2 schematically illustrates an embodiment of a building block including a flexible tether (left) and a building block including a rigid tether (right).

Figure 3:
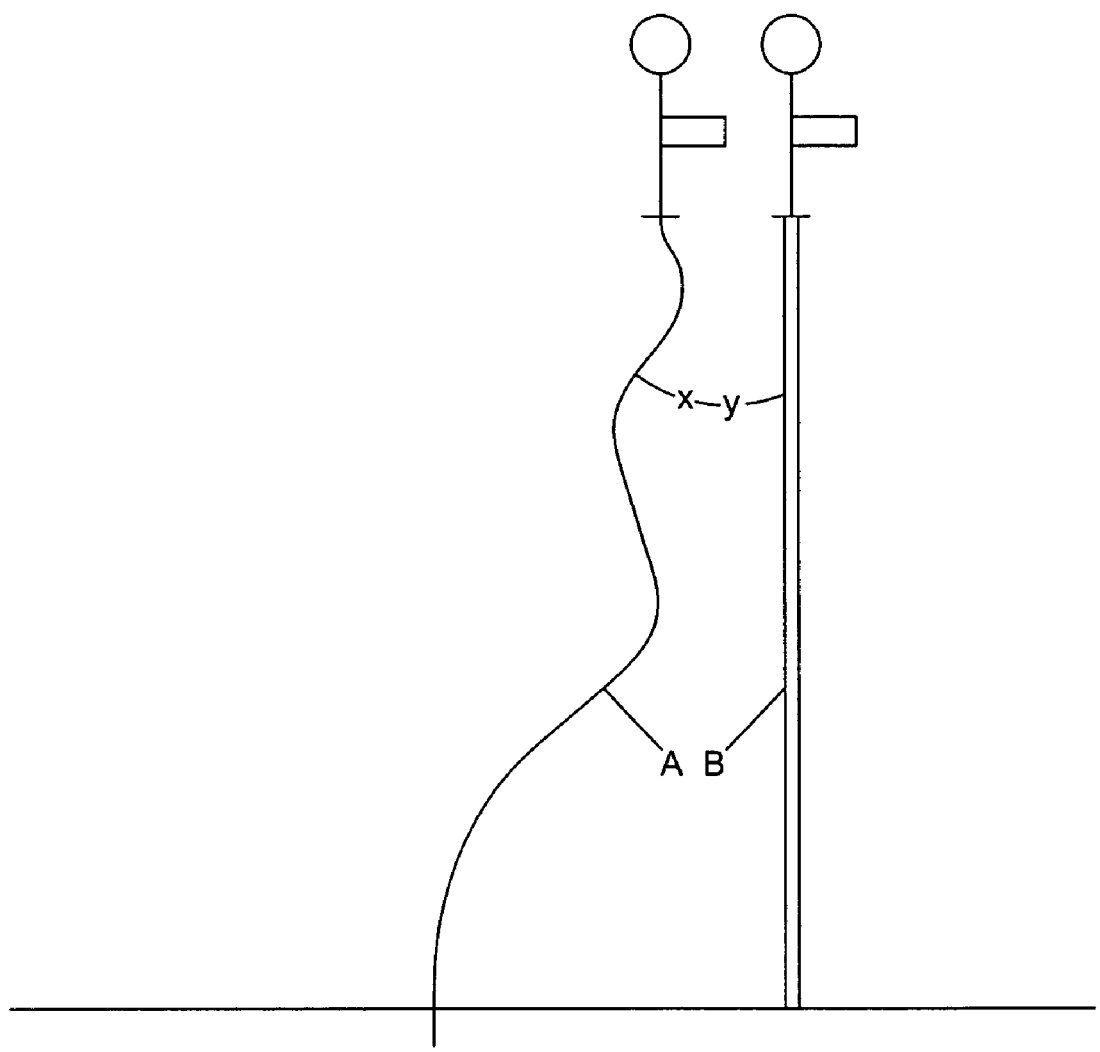
FIG. 3 schematically illustrates an embodiment with two tether building blocks coupled, for example, by a reversible covalent bond between moieties X and Y and by noncovalent interaction between moieties A and B.

The tether can include groups suitable for coupling one tether building block to another or one tether to another. Such coupling can provide, for example, rigidity or positioning to a building block with a flexible tether. Such coupling can maintain, for example, two building blocks in proximity to one another. The coupling can be reversible, which can allow the coupled building blocks to "change partners" and couple to no or a different building block. FIG. 3 schematically illustrates an embodiment with two tether building blocks coupled, for example, by a reversible covalent bond between moieties X and Y and by noncovalent interaction between moieties A and B. The specification below describes suitable groups for forming reversible covalent bonds and noncovalent interactions.

An artificial receptor on a scaffold can include a plurality of building blocks with one or more of the building blocks having a tether moiety. For example, an artificial receptor can include at least one building block without a tether moiety, at least one building block with a linker suitable for reversible immobilization on a scaffold, or at least one tether building block. For example, an artificial receptor can include a plurality of tether building blocks, which can include at least one building block including a rigid tether or at least one building block including a flexible tether. In an embodiment, the artificial receptor can include at least one building block including a rigid tether and at least one building block including a flexible tether. In an embodiment, the artificial receptor can include a plurality of building blocks including a rigid tether and a plurality of building blocks including a flexible tether.

Figure 4:
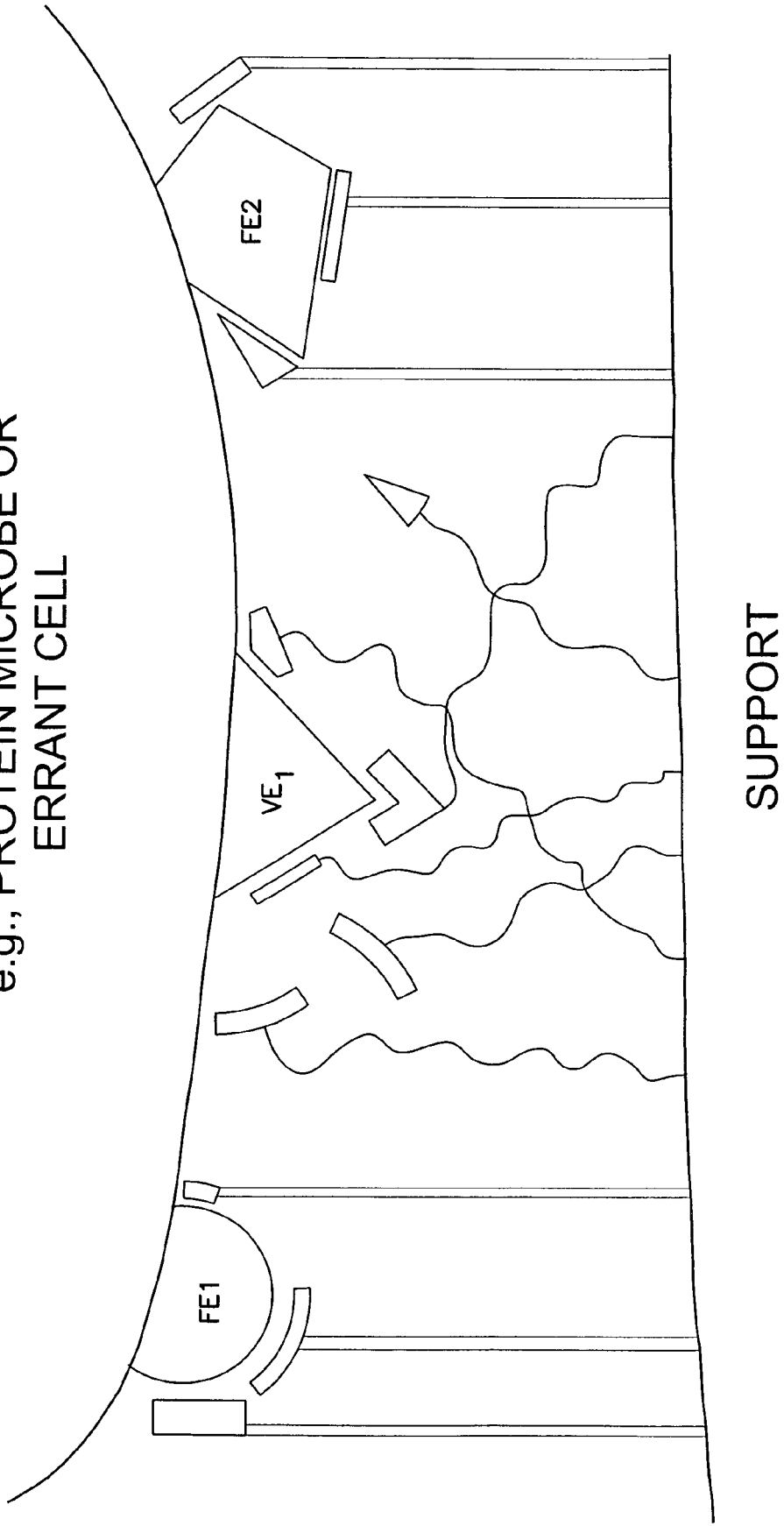
FIG. 4 schematically illustrates an embodiment of a test ligand bound to an embodiment of an artificial receptor including a plurality of building blocks including a rigid tether and a plurality of building blocks including a flexible tether.

FIG. 4 schematically illustrates an embodiment of a test ligand bound to an embodiment of an artificial receptor including a plurality of building blocks including a rigid tether and a plurality of building blocks including a flexible tether. The illustrated test ligand includes three features of interest, FE1, FE2, and VE1. These features can be thought of as epitopes that can be recognized by the artificial receptor, which can be considered analogous to an antibody. Two of the features can be considered to have fixed structures. One of the features can be considered to have a structure that can change or be altered. For example, features FE1 and FE2 can be visualized as fixed epitopes on the surface of a microbe. For example, feature VE1 can be visualized as a variable epitope on the surface of a microbe.

The artificial receptor schematically illustrated in FIG. 4 includes 12 different building blocks, 6 with rigid tethers and 6 with flexible tethers, each coupled to a scaffold. In this illustration, the 6 building blocks with rigid tethers bind to features FE1 and FE2, which can be considered fixed epitopes. Heterogeneous building block combinations that bind to each of features FE1 and FE2 can be selected by methods described herein and in greater detail in Applicant's co-pending applications. In this illustration, 3 of the building blocks with flexible tethers bind to feature $VE_1$, which can be considered form 1 of a variable epitope. Combinations of building blocks including flexible tethers and that bind to feature $VE_1$ can be selected by methods including those described herein and those employed for selecting combinations of other building blocks.

As schematically illustrated in FIG. 4, the artificial receptor includes 3 building blocks with flexible tethers not bound to any feature of the test ligand. In practice, an artificial receptor could include any number of different unbound building blocks with flexible tethers. The unbound flexible tether building blocks can be selected for their ability to bind to different forms of the variable feature, to other features of the test ligand, to another test ligand, or the like. The unbound flexible tether building blocks can be selected to be naïve to the variable feature or the test ligand. That is, the unbound flexible tether building blocks can be selected so that one or more of them has the possibility of binding to, for example, a different form of the variable feature.

Figure 5:
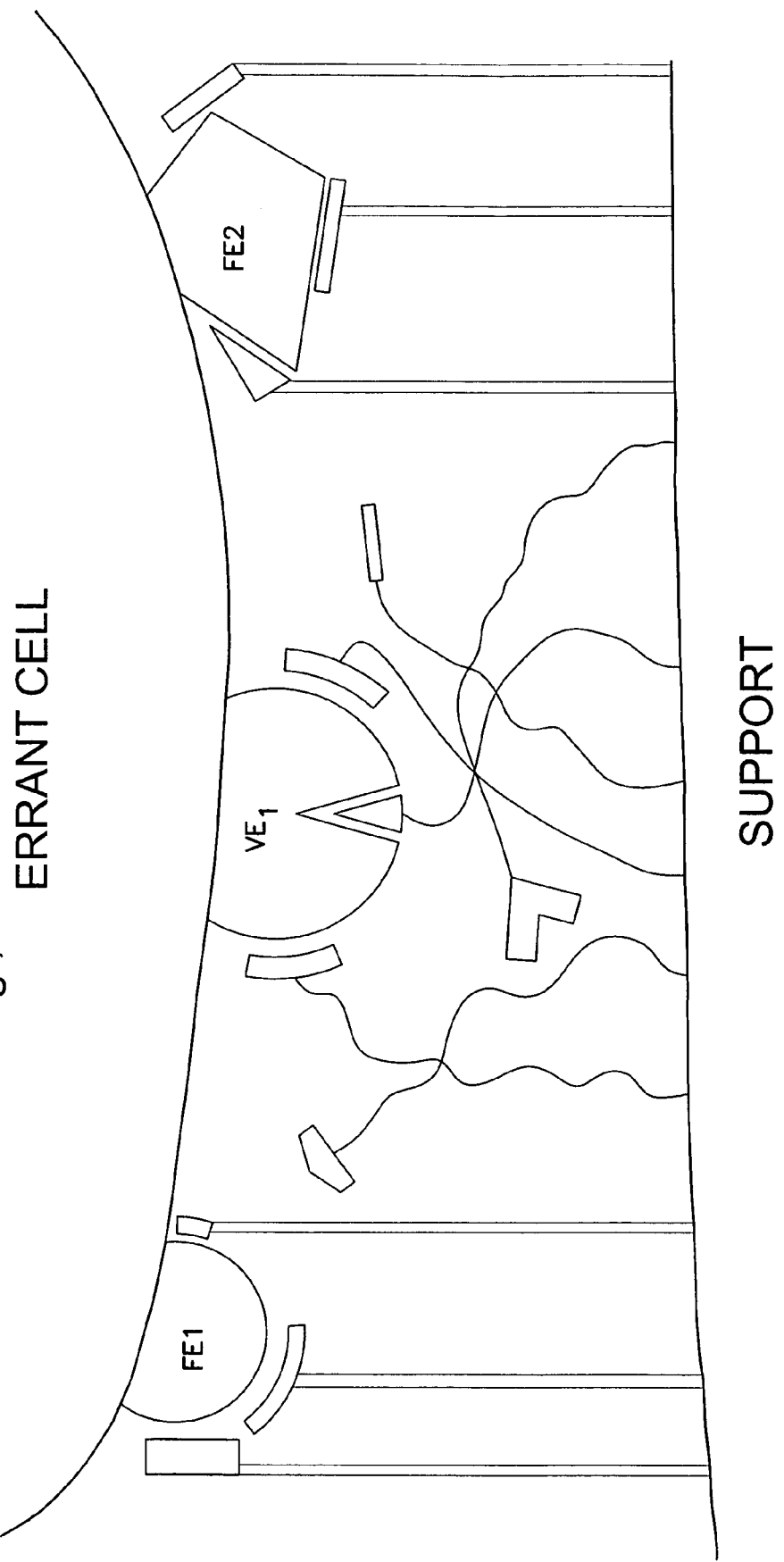
FIG. 5 schematically illustrates the receptor and test ligand of FIG. 15, the test ligand displaying an altered form of feature VE, $VE_2$.

FIG. 5 schematically illustrates the receptor and test ligand of FIG. 4, the test ligand displaying an altered form of feature VE, $VE_2$. The alternate forms of feature VE can be considered, for example, as different forms of a variable protein expressed on the surface of a microbe. The alternate forms of feature VE can be considered, for example, as different structural features on isoforms or variants of a protein. The alternate forms of feature VE can be considered, for example, as different structural features on isomeric or homomorphic compounds.

In an embodiment, one or more flexible tethers can be switched rigid tethers. Each flexible tether can be selectively switched to a rigid tether or remain as a flexible tether. In an embodiment, all flexible tethers can be switched to rigid tethers.

As schematically illustrated in FIG. 5, the rigid tether building blocks each still bind features FE1 and FE2. Binding of the flexible tether building blocks to form $VE_2$ of feature VE has changed. The flexible tether building blocks that had bound to VE1 are now unbound. The flexible tether building blocks that had been unbound are now bound to $VE_2$. The artificial receptor including flexible tether building blocks can bind a plurality of forms of the test ligand. As illustrated, the artificial receptor binds to different forms of the test ligand including versions VE1 and $VE_2$ of feature VE. An artificial receptor including one or more flexible tether building blocks can be referred to as an adaptive receptor.

Building Blocks for Adaptive Artificial Receptors

The present invention relates to building blocks for making or forming candidate artificial receptors. Building blocks can be designed, made, and selected to provide a variety of structural characteristics among a small number of compounds. A building block can provide one or more structural characteristics such as positive charge, negative charge, acid, base, electron acceptor, electron donor, hydrogen bond donor, hydrogen bond acceptor, free electron pair, π electrons, charge polarization, hydrophilicity, hydrophobicity, and the like. A building block can be bulky or it can be small.

A building block can be visualized as including several components, such as one or more frameworks, one or more linkers, one or more recognition elements, and/or one or more tethers. The framework can be covalently coupled to each of the other building block components. The linker can be covalently coupled to the framework. The linker can be coupled to a support through one or more of covalent, electrostatic, hydrogen bonding, van der Waals, or like interactions. The recognition element can be covalently coupled to the framework. The tether can be covalently coupled to the linker and to the framework. In an embodiment, a building block includes a framework, a linker, a recognition element, and a tether. In an embodiment, a building block includes a framework, a linker, a tether, and two recognition elements.

A description of general and specific features and functions of a variety of building blocks and their synthesis can be found in copending U.S. patent application Ser. No. 10/244,727, filed Sep. 16, 2002, Ser. No. 10/813,568, filed Mar. 29, 2004, and Application No. PCT/US03/05328, filed Feb. 19, 2003, each entitled "ARTIFICIAL RECEPTORS, BUILDING BLOCKS, AND METHODS"; U.S. patent application Ser. Nos. 10/812,850 and 10/813,612, and application No. PCT/US2004/009649, each filed Mar. 29, 2004 and each entitled "ARTIFICIAL RECEPTORS INCLUDING REVERSIBLY IMMOBILIZED BUILDING BLOCKS, THE BUILDING BLOCKS, AND METHODS"; and U.S. Provisional Patent Application Nos. 60/499,965, filed Sep. 3, 2003, and 60/526,699, filed Dec. 2, 2003, each entitled BUILDING BLOCKS FOR ARTIFICIAL RECEPTORS; the disclosures of which are incorporated herein by reference. These patent documents include, in particular, a detailed written description of: function, structure, and configuration of building blocks, framework moieties, recognition elements, synthesis of building blocks, specific embodiments of building blocks, specific embodiments of recognition elements, and sets of building blocks.

Framework

The framework can be selected for functional groups that provide for coupling to the recognition moiety and for coupling to or being the tether and/or linking moieties. The framework can interact with the ligand as part of the artificial receptor. In an embodiment, the framework includes multiple reaction sites with orthogonal and reliable functional groups. In an embodiment, the framework includes one or more reaction sites with controlled stereochemistry. Suitable functional groups with orthogonal and reliable chemistries include, for example, carboxyl, amine, hydroxyl, phenol, carbonyl, and thiol groups, which can be individually protected, deprotected, and derivatized. In an embodiment, the framework has two, three, or four functional groups with orthogonal and reliable chemistries. In an embodiment, the framework has three functional groups. In such an embodiment, the three functional groups can be independently selected, for example, from carboxyl, amine, hydroxyl, phenol, carbonyl, or thiol group. The framework can include alkyl, substituted alkyl, cycloalkyl, heterocyclic, substituted heterocyclic, aryl alkyl, aryl, heteroaryl, heteroaryl alkyl, and like moieties.

A general structure for a framework with three functional groups can be represented by Formula 1a:

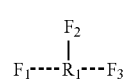

A general structure for a framework with four functional groups can be represented by Formula 1b:

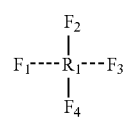

In these general structures: $R_1$ can be a 1-12, a 1-6, or a 1-4 carbon alkyl, substituted alkyl, cycloalkyl, heterocyclic, substituted heterocyclic, aryl alkyl, aryl, heteroaryl, heteroaryl alkyl, or like group; and $F_1$, $F_2$, $F_3$, or $F_4$ can independently be a carboxyl, amine, hydroxyl, phenol, carbonyl, or thiol group. $F_1$, $F_2$, $F_3$, or $F_4$ can independently be a 1-12, a 1-6, a 1-4 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group. $F_3$ and/or $F_4$ can be absent.

A variety of compounds fit the formulas and text describing the framework including amino acids, and naturally occurring or synthetic compounds including, for example, oxygen and sulfur functional groups. The compounds can be racemic, optically active, or achiral. For example, the compounds can be natural or synthetic amino acids, α-hydroxy acids, thioic acids, and the like.

Suitable molecules for use as a framework include a natural or synthetic amino acid, particularly an amino acid with a functional group (e.g., third functional group) on its side chain. Amino acids include carboxyl and amine functional groups. The side chain functional group can include, for natural amino acids, an amine (e.g., alkyl amine, heteroaryl amine), hydroxyl, phenol, carboxyl, thiol, thioether, or amidino group. Natural amino acids suitable for use as frameworks include, for example, serine, threonine, tyrosine, aspartic acid, glutamic acid, asparagine, glutamine, cysteine, lysine, arginine, histidine. Synthetic amino acids can include the naturally occurring side chain functional groups or synthetic side chain functional groups which modify or extend the natural amino acids with alkyl, substituted alkyl, cycloalkyl, heterocyclic, substituted heterocyclic, aryl alkyl, aryl, heteroaryl, heteroaryl alkyl, and like moieties as framework and with carboxyl, amine, hydroxyl, phenol, carbonyl, or thiol functional groups. Suitable synthetic amino acids include β-amino acids and homo or β analogs of natural amino acids. In an embodiment, the framework amino acid can be serine, threonine, or tyrosine, e.g., serine or tyrosine, e.g., tyrosine.

Although not limiting to the present invention, a framework amino acid, such as serine, threonine, or tyrosine, with a linker and two recognition elements can be visualized with one of the recognition elements in a pendant orientation and the other in an equatorial orientation, relative to the extended carbon chain of the framework.

All of the naturally occurring and many synthetic amino acids are commercially available. Further, forms of these amino acids derivatized or protected to be suitable for reactions for coupling to recognition element(s) and/or linkers can be purchased or made by known methods (see, e.g., Green, T W; Wuts, PGM (1999), *Protective Groups in Organic Synthesis Third Edition*, Wiley-Interscience, New York, 779 pp.; Bodanszky, M.; Bodanszky, A. (1994), The Practice of Peptide Synthesis Second Edition, Springer-Verlag, New York, 217 pp.).

Tether

In an embodiment, the present invention relates to a building block including a tether moiety. The tether can include the framework. The tether moiety can provide spacing or distance between the recognition element and the support or scaffold to which the building block is immobilized. A tether moiety can have any of a variety of characteristics or properties including flexibility, rigidity or stiffness, ability to bond to another tether moiety, and the like. The tether moiety can include the linker. The framework moiety can be envisioned as forming all or part of the tether moiety.

Suitable tether moieties can include a polyethylene glycol, a polyamide, a linear polymer, a peptide, a polypeptide, an oligosaccharide, a polysaccharide, a semifunctionalized oligo- or polyglycine. In an embodiment, the tether is or includes a polymer of up to 2000 carbon atoms (e.g., up to 48 carbon atoms). Such a polymer can be naturally occurring or synthetic. Suitable polymers include a polyether or like polymer, such as a PEG, a polyethyleneimine, polyacrylate (e.g., substituted polyacrylates), salt thereof, a mixture or combination thereof, or the like. Suitable PEGs include PEG 1500 up to PEG 20,000, for example, PEG 1450, PEG 3350, PEG 4500, PEG 8000, PEG 20,000, and the like.

Suitable tether moieties can include one or more branched or straight chain C6-36 alkyl, C8-24 alkyl, C12-24 alkyl, C12-18 alkyl, or the like; C6-36 alkenyl, C8-24 alkenyl, C12-24 alkenyl, C12-18 alkenyl, or the like, with, for example, 1 to 4 double bonds; C6-36 alkynyl, C8-24 alkynyl, C12-24 alkynyl, C12-18 alkynyl, or the like, with, for example, 1 to 4 triple bonds; chains with 1-4 double or triple bonds; chains including aryl or substituted aryl moieties (e.g., phenyl or naphthyl moieties at the end or middle of a chain); polyaromatic hydrocarbon moieties; cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. In an embodiment, the lipophilic moiety includes or is a 12-carbon aliphatic moiety.

Rigid tether moieties can include conformationally restricted groups such as imines, aromatics, and polyaromatics. Rigid tether moieties can include one or more branched or straight chain C6-36 alkenyl, C8-24 alkenyl, C12-24 alkenyl, C12-18 alkenyl, or the like, with, for example, 2 to 8 double bonds; C6-36 alkynyl, C8-24 alkynyl, C12-24 alkynyl, C12-18 alkynyl, or the like, with, for example, 1 to 8 triple bonds; chains with 3-8 double or triple bonds; chains including aryl or substituted aryl moieties (e.g., phenyl or naphthyl moieties at the end or middle of a chain); polyaromatic hydrocarbon moieties; and the like. The alkenyl or alkynyl group can include branching; within chain functionality like an ether group; terminal functionality like alcohol, amide, carboxylate or the like; or the like. Rigid tether moieties can include a steroid moiety, such as cholesterol, a corrin or another porphyrin, a polynuclear aromatic moiety, a polar polymer fixed with metal ions, or the like.

In an embodiment, a rigid tether moiety can include more than one tether moiety. For example, a rigid tether moiety can include a plurality of hydrophobic chains, such as those described in the paragraph above and in the paragraph below. The hydrophobic chains if held in sufficient proximity on the support or scaffold will, in a hydrophobic solvent, form a grouping sufficiently rigid to hold one or more sets of recognition elements in place. In another embodiment, a rigid tether moiety can include a plurality of otherwise flexible tether moieties crosslinked to one another. The crosslinking can include, for example, covalent bonding, electrostatic interactions, hydrogen bonding, or hydrophobic interactions. Groups for forming such interactions are disclosed herein.

Flexible tether moieties can include one or more branched or straight chain C6-36 alkyl, C8-24 alkyl, C12-24 alkyl, C12-18 alkyl, or the like; C6-36 alkenyl, C8-24 alkenyl, C12-24 alkenyl, C12-18 alkenyl, or the like, with, for example, 1 to 2 double bonds; C6-36 alkynyl, C8-24 alkynyl, C12-24 alkynyl, C12-18 alkynyl, or the like, with, for example, 1 to 2 triple bonds; chains with 1-2 double or triple bonds; chains including 1 to 2 aryl or substituted aryl moieties (e.g., phenyl or naphthyl moieties at the end or middle of a chain); cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. In an embodiment, the lipophilic moiety includes or is a 12-carbon aliphatic moiety.

In an embodiment, the tether forms or can be visualized as forming a covalent bond with an alcohol, phenol, thiol, amine, carbonyl, or like group on the framework. Between the bond to the framework and the group participating in or formed by the interaction with the support or lawn, the linker can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

Suitable tethers can include, for example: the functional group participating in or formed by the bond to the framework, the functional group or groups participating in or formed by the interaction with the support or lawn, and a tether backbone moiety. The tether backbone moiety can include about 8 to about 200 carbon or heteroatoms, about 12 to about 150 carbon or heteroatoms, about 16 to about 100 carbon or heteroatoms, about 16 to about 50 carbon or heteroatoms, or the like. The tether backbone can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, mixtures thereof, or like moiety. Suitable tethers have structures such as (CH2)nCOOH, with n=12-24, n=17-24, or n=16-18.

The tether can interact with the ligand as part of the artificial receptor. The tether can also provide bulk, distance from the support, hydrophobicity, hydrophilicity, and like structural characteristics to the building block. In an embodiment, the tether forms a covalent bond with a functional group on the framework. In an embodiment, the tether also includes a functional group that can couple to the tether or to the support or lawn, e.g., through covalent bonding or noncovalent interactions.

In an embodiment, the tether includes one or more moieties for forming a reversible covalent bond, a hydrogen bond, or an ionic interaction, e.g., with another tether moiety. For example, the linker can include about 1 to about 20 reversible bond/interaction moieties or about 2 to about 10 reversible bond/interaction moieties.

In an embodiment, the tether includes one or more moieties that can engage in reversible covalent bonding. Suitable groups for reversible covalent bonding include those described hereinabove. Such groups for reversible covalent bonds can be part of links between tether moieties. The tether-tether links can include, for example, imine, acetal, ketal, disulfide, ester, or like linkages. Such functional groups can engage in reversible covalent bonding. Such a functional group can be referred to as a covalent bonding moiety.

In an embodiment, the tether can be functionalized with moieties that can engage in noncovalent interactions. For example, the tether can include functional groups such as an ionic group, a group that can hydrogen bond, or a group that can engage in van der Waals or other hydrophobic interactions. Such functional groups can include cationic groups, anionic groups, lipophilic groups, amphiphilic groups, and the like.

In an embodiment, the present methods and compositions can employ a tether including a charged moiety. Suitable charged moieties include positively charged moieties and negatively charged moieties. Suitable positively charged moieties include protonated amines, quaternary ammonium moieties, sulfonium, sulfoxonium, phosphonium, ferrocene, and the like. Suitable negatively charged moieties (e.g., at neutral pH in aqueous compositions) include carboxylates, phenols substituted with strongly electron withdrawing groups (e.g., tetrachlorophenols), phosphates, phosphonates, phosphinates, sulphates, sulphonates, thiocarboxylates, and hydroxamic acids.

In an embodiment, the present methods and compositions can employ a tether including a group that can hydrogen bond, either as donor or acceptor (e.g., a second hydrogen bonding group). For example, the tether can include one or more carboxyl groups, amine groups, hydroxyl groups, carbonyl groups, or the like. Ionic groups can also participate in hydrogen bonding.

Recognition Element

The recognition element can be selected to provide one or more structural characteristics to the building block. The recognition element can interact with the ligand as part of the artificial receptor. For example, the recognition element can provide one or more structural characteristics such as positive charge, negative charge, acid, base, electron acceptor, electron donor, hydrogen bond donor, hydrogen bond acceptor, free electron pair, π electrons, charge polarization, hydrophilicity, hydrophobicity, and the like. A recognition element can be a small group or it can be bulky.

In an embodiment the recognition element can be a 1-12, a 1-6, or a 1-4 carbon alkyl, substituted alkyl, cycloalkyl, heterocyclic, substituted heterocyclic, aryl alkyl, aryl, heteroaryl, heteroaryl alkyl, or like group. The recognition element can be substituted with a group that includes or imparts positive charge, negative charge, acid, base, electron acceptor, electron donor, hydrogen bond donor, hydrogen bond acceptor, free electron pair, π electrons, charge polarization, hydrophilicity, hydrophobicity, and the like.

Recognition elements with a positive charge (e.g., at neutral pH in aqueous compositions) include protonated amines, quaternary ammonium moieties, sulfonium, sulfoxonium, phosphonium, ferrocene, and the like. Suitable amines include alkyl amines, alkyl diamines, heteroalkyl amines, aryl amines, heteroaryl amines, aryl alkyl amines, pyridines, heterocyclic amines (saturated or unsaturated, the nitrogen in the ring or not), amidines, hydrazines, and the like. Alkyl amines generally have 1 to 12 carbons, e.g., 1-8, and rings can have 3-12 carbons, e.g., 3-8. Suitable alkyl amines include that of formula B9. Suitable heterocyclic or alkyl heterocyclic amines include that of formula A9. Suitable pyridines include those of formulas A5 and B5. Any of the amines can be employed as a quaternary ammonium compound. Additional suitable quaternary ammonium moieties include trimethyl alkyl quaternary ammonium moieties, dimethyl ethyl alkyl quaternary ammonium moieties, dimethyl alkyl quaternary ammonium moieties, aryl alkyl quaternary ammonium moieties, pyridinium quaternary ammonium moieties, and the like.

Recognition elements with a negative charge (e.g., at neutral pH in aqueous compositions) include carboxylates, phenols substituted with strongly electron withdrawing groups (e.g., substituted tetrachlorophenols), phosphates, phosphonates, phosphinates, sulphates, sulphonates, thiocarboxylates, and hydroxamic acids. Suitable carboxylates include alkyl carboxylates, aryl carboxylates, and aryl alkyl carboxylates. Suitable phosphates include phosphate mono-, di-, and tri-esters, and phosphate mono-, di-, and tri-amides. Suitable phosphonates include phosphonate mono- and di-esters, and phosphonate mono- and di-amides (e.g., phosphonamides). Suitable phosphinates include phosphinate esters and amides.

Recognition elements with a negative charge and a positive charge (at neutral pH in aqueous compositions) include sulfoxides, betaines, and amine oxides.

Acidic recognition elements can include carboxylates, phosphates, sulphates, and phenols. Suitable acidic carboxylates include thiocarboxylates. Suitable acidic phosphates include the phosphates listed hereinabove.

Basic recognition elements include amines. Suitable basic amines include alkyl amines, aryl amines, aryl alkyl amines, pyridines, heterocyclic amines (saturated or unsaturated, the nitrogen in the ring or not), amidines, and any additional amines listed hereinabove. Suitable alkyl amines include that of formula B9. Suitable heterocyclic or alkyl heterocyclic amines include that of formula A9. Suitable pyridines include those of formulas A5 and B5.

Recognition elements including a hydrogen bond donor include amines, amides, carboxyls, protonated phosphates, protonated phosphonates, protonated phosphinates, protonated sulphates, protonated sulphinates, alcohols, and thiols. Suitable amines include alkyl amines, aryl amines, aryl alkyl amines, pyridines, heterocyclic amines (saturated or unsaturated, the nitrogen in the ring or not), amidines, ureas, and any other amines listed hereinabove. Suitable alkyl amines include that of formula B9. Suitable heterocyclic or alkyl heterocyclic amines include that of formula A9. Suitable pyridines include those of formulas A5 and B5. Suitable protonated carboxylates, protonated phosphates include those listed hereinabove. Suitable amides include those of formulas A8 and B8. Suitable alcohols include primary alcohols, secondary alcohols, tertiary alcohols, and aromatic alcohols (e.g., phenols). Suitable alcohols include those of formulas A7 (a primary alcohol) and B7 (a secondary alcohol).

Recognition elements including a hydrogen bond acceptor or one or more free electron pairs include amines, amides, carboxylates, carboxyl groups, phosphates, phosphonates, phosphinates, sulphates, sulphonates, alcohols, ethers, thiols, and thioethers. Suitable amines include alkyl amines, aryl amines, aryl alkyl amines, pyridines, heterocyclic amines (saturated or unsaturated, the nitrogen in the ring or not), amidines, ureas, and amines as listed hereinabove. Suitable alkyl amines include that of formula B9. Suitable heterocyclic or alkyl heterocyclic amines include that of formula A9. Suitable pyridines include those of formulas A5 and B5. Suitable carboxylates include those listed hereinabove. Suitable amides include those of formulas A8 and B8. Suitable phosphates, phosphonates and phosphinates include those listed hereinabove. Suitable alcohols include primary alcohols, secondary alcohols, tertiary alcohols, aromatic alcohols, and those listed hereinabove. Suitable alcohols include those of formulas A7 (a primary alcohol) and B7 (a secondary alcohol). Suitable ethers include alkyl ethers, aryl alkyl ethers. Suitable alkyl ethers include that of formula A6. Suitable aryl alkyl ethers include that of formula A4. Suitable thioethers include that of formula B6.

Recognition elements including uncharged polar or hydrophilic groups include amides, alcohols, ethers, thiols, thioethers, esters, thio esters, boranes, borates, and metal complexes. Suitable amides include those of formulas A8 and B8. Suitable alcohols include primary alcohols, secondary alcohols, tertiary alcohols, aromatic alcohols, and those listed hereinabove. Suitable alcohols include those of formulas A7 (a primary alcohol) and B7 (a secondary alcohol). Suitable ethers include those listed hereinabove. Suitable ethers include that of formula A6. Suitable aryl alkyl ethers include that of formula A4.

Recognition elements including uncharged hydrophobic groups include alkyl (substituted and unsubstituted), alkene (conjugated and unconjugated), alkyne (conjugated and unconjugated), aromatic. Suitable alkyl groups include lower alkyl, substituted alkyl, cycloalkyl, aryl alkyl, and heteroaryl alkyl. Suitable lower alkyl groups include those of formulas A1, A3, A3a, and B1. Suitable aryl alkyl groups include those of formulas A3, A3a, A4, B3, B3a, and B4. Suitable alkyl cycloalkyl groups include that of formula B2. Suitable alkene groups include lower alkene and aryl alkene. Suitable aryl alkene groups include that of formula B4. Suitable aromatic groups include unsubstituted aryl, heteroaryl, substituted aryl, aryl alkyl, heteroaryl alkyl, alkyl substituted aryl, and polyaromatic hydrocarbons. Suitable aryl alkyl groups include those of formulas A3, A3a and B4. Suitable alkyl heteroaryl groups include those of formulas A5 and B5.

Spacer (e.g., small) recognition elements include hydrogen, methyl, ethyl, and the like. Bulky recognition elements include 7 or more carbon or hetero atoms.

Formulas A1-A9 and B1-B9 are:

A1

A2

A3

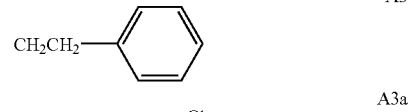

A3a

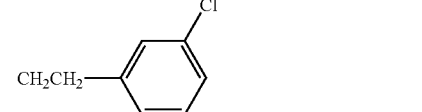

A4

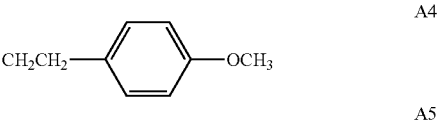

A5

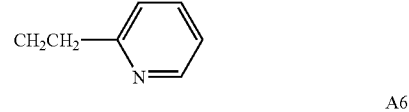

A6

A7

A8

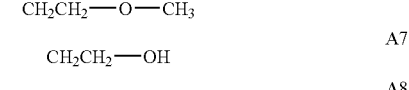

A9

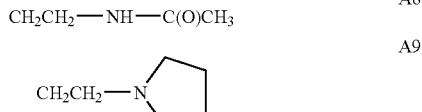

B1

B2

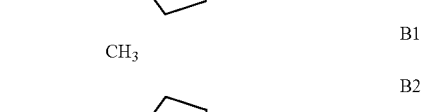

B3

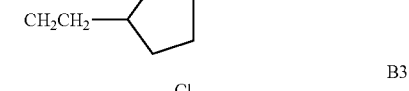

-continued

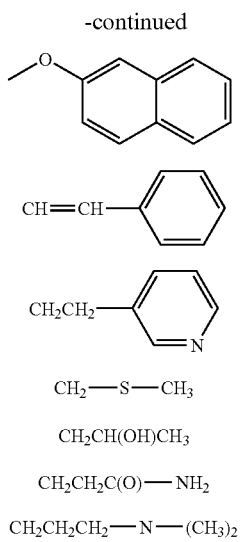

B3a

CH=CH—⌬   B4

CH₂CH₂—(pyridine)   B5

CH₂—S—CH₃   B6

CH₂CH(OH)CH₃   B7

CH₂CH₂C(O)—NH₂   B8

CH₂CH₂CH₂—N—(CH₃)₂   B9

These A and B recognition elements can be called derivatives of, according to a standard reference: A1, ethylamine; A2, isobutylamine; A3, phenethylamine; A4, 4-methoxyphenethylamine; A5, 2-(2-aminoethyl)pyridine; A6, 2-methoxyethylamine; A7, ethanolamine; A8, N-acetylethylenediamine; A9, 1-(2-aminoethyl)pyrrolidine; B1, acetic acid, B2, cyclopentylpropionic acid; B3, 3-chlorophenylacetic acid; B4, cinnamic acid; B5, 3-pyridinepropionic acid; B6, (methylthio)acetic acid; B7, 3-hydroxybutyric acid; B8, succinamic acid; and B9, 4-(dimethylamino)butyric acid.

In an embodiment, the recognition elements include one or more of the structures represented by formulas A1, A2, A3, A3a, A4, A5, A6, A7, A8, and/or A9 (the A recognition elements) and/or B1, B2, B3, B3a, B4, B5, B6, B7, B8, and/or B9 (the B recognition elements). In an embodiment, each building block includes an A recognition element and a B recognition element. In an embodiment, a group of 81 such building blocks includes each of the 81 unique combinations of an A recognition element and a B recognition element. In an embodiment, the A recognition elements are linked to a framework at a pendant position. In an embodiment, the B recognition elements are linked to a framework at an equatorial position. In an embodiment, the A recognition elements are linked to a framework at a pendant position and the B recognition elements are linked to the framework at an equatorial position.

Although not limiting to the present invention, it is believed that the A and B recognition elements represent the assortment of functional groups and geometric configurations employed by polypeptide receptors. Although not limiting to the present invention, it is believed that the A recognition elements represent six advantageous functional groups or configurations and that the addition of functional groups to several of the aryl groups increases the range of possible binding interactions. Although not limiting to the present invention, it is believed that the B recognition elements represent six advantageous functional groups, but in different configurations than employed for the A recognition elements. Although not limiting to the present invention, it is further believed that this increases the range of binding interactions and further extends the range of functional groups and configurations that is explored by molecular configurations of the building blocks.

In an embodiment, the building blocks including the A and B recognition elements can be visualized as occupying a binding space defined by lipophilicity/hydrophilicity and volume. A volume can be calculated (using known methods) for each building block including the various A and B recognition elements. A measure of lipophilicity/hydrophilicity (logP) can be calculated (using known methods) for each building block including the various A and B recognition elements. Negative values of logP show affinity for water over nonpolar organic solvent and indicate a hydrophilic nature. A plot of volume versus logP can then show the distribution of the building blocks through a binding space defined by size and lipophilicity/hydrophilicity.

Reagents that form many of the recognition elements are commercially available. For example, reagents for forming recognition elements A1, A2, A3, A3a, A4, A5, A6, A7, A8, A9 B1, B2, B3, B3a, B4, B5, B6, B7, B8, and B9 are commercially available.

Linkers

The linker is selected to provide a suitable coupling of the building block to a support. The framework can interact with the ligand as part of the artificial receptor. The linker can also provide bulk, distance from the support, hydrophobicity, hydrophilicity, and like structural characteristics to the building block. Coupling building blocks to the support can employ covalent bonding or noncovalent interactions. Suitable noncovalent interactions include interactions between ions, hydrogen bonding, van der Waals interactions, and the like. In an embodiment, the linker includes moieties that can engage in covalent bonding or noncovalent interactions. In an embodiment, the linker includes moieties that can engage in covalent bonding. Suitable groups for forming covalent and reversible covalent bonds are described hereinabove.

Linkers for Reversibly Immobilizable Building Blocks

The linker can be selected to provide suitable reversible immobilization of the building block on a support or lawn. In an embodiment, the linker forms a covalent bond with a functional group on the framework. In an embodiment, the linker also includes a functional group that can reversibly interact with the support or lawn, e.g., through reversible covalent bonding or noncovalent interactions.

In an embodiment, the linker includes one or more moieties that can engage in reversible covalent bonding. Suitable groups for reversible covalent bonding include those described hereinabove. An artificial receptor can include building blocks reversibly immobilized on the lawn or support through, for example, imine, acetal, ketal, disulfide, ester, or like linkages. Such functional groups can engage in reversible covalent bonding. Such a functional group can be referred to as a covalent bonding moiety, e.g., a second covalent bonding moiety.

In an embodiment, the linker can be functionalized with moieties that can engage in noncovalent interactions. For example, the linker can include functional groups such as an ionic group, a group that can hydrogen bond, or a group that can engage in van der Waals or other hydrophobic interactions. Such functional groups can include cationic groups, anionic groups, lipophilic groups, amphiphilic groups, and the like.

In an embodiment, the present methods and compositions can employ a linker including a charged moiety (e.g., a second charged moiety). Suitable charged moieties include positively charged moieties and negatively charged moieties. Suitable positively charged moieties include protonated amines, quaternary ammonium moieties, sulfonium, sulfoxonium, phosphonium, ferrocene, and the like. Suitable negatively charged moieties (e.g., at neutral pH in aqueous compositions) include carboxylates, phenols substituted with strongly electron withdrawing groups (e.g., tetrachlorophenols), phosphates, phosphonates, phosphinates, sulphates, sulphonates, thiocarboxylates, and hydroxamic acids.

In an embodiment, the present methods and compositions can employ a linker including a group that can hydrogen bond, either as donor or acceptor (e.g., a second hydrogen bonding group). For example, the linker can include one or more carboxyl groups, amine groups, hydroxyl groups, carbonyl groups, or the like. Ionic groups can also participate in hydrogen bonding.

In an embodiment, the present methods and compositions can employ a linker including a lipophilic moiety (e.g., a second lipophilic moiety). Suitable lipophilic moieties include one or more branched or straight chain C6-36 alkyl, C8-24 alkyl, C12-24 alkyl, C12-18 alkyl, or the like; C6-36 alkenyl, C8-24 alkenyl, C12-24 alkenyl, C12-18 alkenyl, or the like, with, for example, 1 to 4 double bonds; C6-36 alkynyl, C8-24 alkynyl, C12-24 alkynyl, C12-18 alkynyl, or the like, with, for example, 1 to 4 triple bonds; chains with 1-4 double or triple bonds; chains including aryl or substituted aryl moieties (e.g., phenyl or naphthyl moieties at the end or middle of a chain); polyaromatic hydrocarbon moieties; cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. In an embodiment the linker includes or is a lipid, such as a phospholipid. In an embodiment, the lipophilic moiety includes or is a 12-carbon aliphatic moiety.

In an embodiment, the linker includes a lipophilic moiety (e.g., a second lipophilic moiety) and a covalent bonding moiety (e.g., a second covalent bonding moiety). In an embodiment, the linker includes a lipophilic moiety (e.g., a second lipophilic moiety) and a charged moiety (e.g., a second charged moiety).

In an embodiment, the linker forms or can be visualized as forming a covalent bond with an alcohol, phenol, thiol, amine, carbonyl, or like group on the framework. Between the bond to the framework and the group participating in or formed by the reversible interaction with the support or lawn, the linker can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

For example, suitable linkers can include: the functional group participating in or formed by the bond to the framework, the functional group or groups participating in or formed by the reversible interaction with the support or lawn, and a linker backbone moiety. The linker backbone moiety can include about 4 to about 48 carbon or heteroatoms, about 8 to about 14 carbon or heteroatoms, about 12 to about 24 carbon or heteroatoms, about 16 to about 18 carbon or heteroatoms, about 4 to about 12 carbon or heteroatoms, about 4 to about 8 carbon or heteroatoms, or the like. The linker backbone can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, mixtures thereof, or like moiety.

In an embodiment, the linker includes a lipophilic moiety, the functional group participating in or formed by the bond to the framework, and, optionally, one or more moieties for forming a reversible covalent bond, a hydrogen bond, or an ionic interaction. In such an embodiment, the lipophilic moiety can have about 4 to about 48 carbons, about 8 to about 14 carbons, about 12 to about 24 carbons, about 16 to about 18 carbons, or the like. In such an embodiment, the linker can include about 1 to about 8 reversible bond/interaction moieties or about 2 to about 4 reversible bond/interaction moieties. Suitable linkers have structures such as $(CH_2)_nCOOH$, with $n=12-24$, $n=17-24$, or $n=16-18$.

Additional Embodiments of Linkers

The linker can be selected to provide a suitable covalent coupling of the building block to a support. The framework can interact with the ligand as part of the artificial receptor. The linker can also provide bulk, distance from the support, hydrophobicity, hydrophilicity, and like structural characteristics to the building block. In an embodiment, the linker forms a covalent bond with a functional group on the framework. In an embodiment, before attachment to the support the linker also includes a functional group that can be activated to react with or that will react with a functional group on the support. In an embodiment, once attached to the support, the linker forms a covalent bond with the support and with the framework.

In an embodiment, the linker forms or can be visualized as forming a covalent bond with an alcohol, phenol, thiol, amine, carbonyl, or like group on the framework. The linker can include a carboxyl, alcohol, phenol, thiol, amine, carbonyl, maleimide, or like group that can react with or be activated to react with the support. Between the bond to the framework and the group formed by the attachment to the support, the linker can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

The linker can include a good leaving group bonded to, for example, an alkyl or aryl group. The leaving group being "good" enough to be displaced by the alcohol, phenol, thiol, amine, carbonyl, or like group on the framework. Such a linker can include a moiety represented by the formula: R—X, in which X is a leaving group such as halogen (e.g., —Cl, —Br or —I), tosylate, mesylate, triflate, and R is alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

Suitable linker groups include those of formula: $(CH_2)_nCOOH$, with $n=1-16$, $n=2-8$, $n=2-6$, or $n=3$. Reagents that form suitable linkers are commercially available and include any of a variety of reagents with orthogonal functionality.

Embodiments of Building Blocks

In an embodiment, building blocks can be represented by Formula 2:

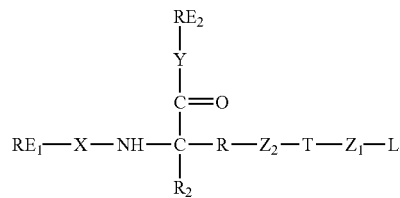

in which: RE1 is recognition element 1, RE2 is recognition element 2, T is an optional tether, and L is a linker. X is absent, C=O, CH2, NR, NR2, NH, NHCONH, SCONH, CH=N, or OCH2NH. In certain embodiments, X is absent or C=O. Y is absent, NH, O, CH2, or NRCO. In certain embodiments, Y is NH or O. In an embodiment, Y is NH. Z1 and Z2 can independently be CH2, O, NH, S, CO, NR, NR2, NHCONH, SCONH, CH=N, or OCH2NH. In an embodiment, Z1 and/or Z2 can independently be O. Z2 is optional. R2 is H, CH3, or another group that confers chirality on the building block and has size similar to or smaller than a methyl group. R3 is CH2; CH2-phenyl; CHCH3; (CH2)n with n=2-3; or cyclic alkyl with 3-8 carbons, e.g., 5-6 carbons, phenyl, naphthyl. In certain embodiments, R3 is CH2 or CH2-phenyl.

RE1 is B1, B2, B3, B3a, B4, B5, B6, B7, B8, B9, A1, A2, A3, A3a, A4, A5, A6, A7, A8, or A9. In certain embodiments, RE1 is B1, B2, B3, B3a, B4, B5, B6, B7, B8, or B9. RE2 is A1, A2, A3, A3a, A4, A5, A6, A7, A8, A9, B1, B2, B3, B3a, B4, B5, B6, B7, B8, or B9. In certain embodiments, RE2 is A1, A2, A3, A3a, A4, A5, A6, A7, A8, or A9. In an embodiment, RE1 can be B2, B3a, B4, B5, B6, B7, or B8. In an embodiment, RE2 can be A2, A3a, A4, A5, A6, A7, or A8.

In an embodiment, L is the functional group participating in or formed by the bond to the framework (such groups are described herein), the functional group or groups participating in or formed by the reversible interaction with the support or lawn (such groups are described herein), and a linker backbone moiety. In an embodiment, the linker backbone moiety is about 4 to about 48 carbon or heteroatom alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or mixtures thereof; or about 8 to about 14 carbon or heteroatoms, about 12 to about 24 carbon or heteroatoms, about 16 to about 18 carbon or heteroatoms, about 4 to about 12 carbon or heteroatoms, about 4 to about 8 carbon or heteroatoms.

In an embodiment, the L is the functional group participating in or formed by the bond to the framework (such groups are described herein) and a lipophilic moiety (such groups are described herein) of about 4 to about 48 carbons, about 8 to about 14 carbons, about 12 to about 24 carbons, about 16 to about 18 carbons. In an embodiment, this L also includes about 1 to about 8 reversible bond/interaction moieties (such groups are described herein) or about 2 to about 4 reversible bond/interaction moieties. In an embodiment, L is (CH2)nCOOH, with n=12-24, n=17-24, or n=16-18.

In an embodiment, L is (CH2)nCOOH, with n=1-16, n=2-8, n=4-6, or n=3.

Building blocks including an A and/or a B recognition element, a linker, and an amino acid framework can be made by methods illustrated in general Scheme 1.

Scaffolds

In an embodiment, an artificial receptor of the present invention includes a plurality of building blocks coupled to a scaffold. In an embodiment, a scaffold supports an artificial receptor including a combination of 2, 3, 4, or more building blocks occupying distinct positions relative to one another on the scaffold. Such an artificial receptor is referred to as a scaffold artificial receptor. A scaffold artificial receptor is not coupled to a support unless explicitly described as being so coupled. In an embodiment, a scaffold, having coupled to it a plurality of building blocks, can additionally be coupled to a support.

In an embodiment, the scaffold can be envisioned as forming one or more tether moieties. In an embodiment, the scaffold can be envisioned as forming one or more linker moieties. In an embodiment, the scaffold can be envisioned as forming one or more tether moieties, and one or more linker moieties. In an embodiment, the scaffold can be envisioned as forming one or more framework moieties. In an embodiment, the scaffold can be envisioned as forming a combination of: zero, one or more framework moieties; zero, one or more linker moieties; and/or zero, one or more tether moieties; at each distinct position on the scaffold. Each distinct position can also be called a reactive site.

The scaffold can be an organic molecule, inorganic molecule, organometallic molecule, or any combination or assembly thereof. The scaffold can be an organic molecule generally formed of carbon and heteroatoms (and may additionally include coordinated metals or organometallic functional groups) combined in combinations of units hydrocarbon and functional groups. In an embodiment, the scaffold is less than or equal to approximately 1 nanometer in size. Organic molecules less than or equal to 1 nanometer in size include small organic molecules, including buckminsterfullerene ($C_{60}$, approximately 1 nm in diameter). In an embodiment, the scaffold can include alkyl, substituted alkyl, cycloalkyl, heterocyclic, substituted heterocyclic, aryl alkyl, aryl, heteroaryl, heteroaryl alkyl, and like moieties. In an embodiment, the scaffold is greater than approximately 1 nanometer in size, up to approximately 10 nanometers, but may be as large as 100 nanometers. Organic molecules greater than 1 nanometer in size include, for example, macromolecules, such as dendrimers and those generated by traditional polymer chemistry, as well as biological macromolecules, including DNA, RNA, and proteins.

The scaffold can be selected for functional groups to provide a suitable coupling of the building blocks to the scaffold. In an embodiment, the functional groups of the scaffold are located at distinct positions, each position being a reaction site. Coupling building blocks to the scaffold can employ covalent bonding, weaker than covalent bonding and ionic bonding interactions. Suitable noncovalent interactions include interactions between ions, hydrogen bonding, van der Waals interactions, and the like. In an embodiment, the scaffold includes moieties that can engage in covalent bonding or noncovalent interactions. In an embodiment, the scaffold includes moieties that can engage in covalent bonding. Suitable groups for forming covalent and reversible covalent bonds are described herein.

In an embodiment, the scaffold includes one or more moieties that can engage in reversible covalent bonding. Suitable groups for reversible covalent bonding include those described hereinabove. An artificial receptor can include building blocks reversibly immobilized on a scaffold through, for example, imine, acetal, ketal, disulfide, ester, or like linkages. Such functional groups can engage in reversible covalent bonding. Such a functional group can be referred to as a covalent bonding moiety, e.g., a second covalent bonding moiety.

In an embodiment, the scaffold can be functionalized with moieties that can engage in covalent bonding, e.g., reversible covalent bonding. The present invention can employ any of a variety of the numerous known functional groups, reagents, and reactions for forming reversible covalent bonds. Suitable reagents for forming reversible covalent bonds include those described in Green, T W; Wuts, PGM (1999), *Protective Groups in Organic Synthesis Third Edition*, Wiley-Interscience, New York, 779 pp. For example, the scaffold can include functional groups such as a carbonyl group, a carboxyl group, a silane group, boric acid or ester, an amine group (e.g., a primary, secondary, or tertiary amine, a hydroxylamine, a hydrazine, or the like), a thiol group, an alcohol group (e.g., primary, secondary, or tertiary alcohol), a diol group (e.g., a 1,2 diol or a 1,3 diol), a phenol group, a catechol group, or the like. These functional groups can form groups with reversible covalent bonds, such as ether (e.g., alkyl ether, silyl ether, thioether, or the like), ester (e.g., alkyl ester, phenol ester, cyclic ester, thioester, or the like), acetal (e.g., cyclic acetal), ketal (e.g., cyclic ketal), silyl derivative (e.g., silyl ether), boronate (e.g., cyclic boronate), amide, hydrazide, imine, carbamate, or the like. Such a functional group can be referred to as a covalent bonding moiety, e.g., a first covalent bonding moiety.

A carbonyl group on the scaffold and an amine group on a building block can form an imine or Schiff's base. The same is true of an amine group on the scaffold and a carbonyl group on a building block. A carbonyl group on the scaffold and an alcohol group on a building block can form an acetal or ketal. The same is true of an alcohol group on the scaffold and a carbonyl group on a building block. A thiol (e.g., a first thiol) on the scaffold and a thiol (e.g., a second thiol) on the building block can form a disulfide.

A carboxyl group on the scaffold and an alcohol group on a building block can form an ester. The same is true of an alcohol group on the scaffold and a carboxyl group on a building block. Any of a variety of alcohols and carboxylic acids can form esters that provide covalent bonding that can be reversed in the context of the present invention. For example, reversible ester linkages can be formed from alcohols such as phenols with electron withdrawing groups on the aryl ring, other alcohols with electron withdrawing groups acting on the hydroxyl-bearing carbon, other alcohols, or the like; and/or carboxyl groups such as those with electron withdrawing groups acting on the acyl carbon (e.g., nitrobenzylic acid, R—$CF_2$—COOH, R—$CCl_2$—COOH, and the like), other carboxylic acids, or the like.

In an embodiment, the scaffold can be functionalized with moieties that can engage in noncovalent or weaker than covalent interactions. For example, the scaffold can include functional groups such as an ionic group, a group that can hydrogen bond, a group that can engage in host-guest interactions, or a group that can engage in van der Waals or other hydrophobic interactions. Such functional groups can include cationic groups, anionic groups, lipophilic groups, amphiphilic groups, and the like.

In an embodiment, the present methods and compositions can employ a scaffold including a charged moiety (e.g., a second charged moiety). Suitable charged moieties include positively charged moieties and negatively charged moieties. Suitable positively charged moieties include amines, quaternary ammonium moieties, sulfonium, phosphonium, ferrocene, and the like. Suitable negatively charged moieties (e.g., at neutral pH in aqueous compositions) include carboxylates, phenols substituted with strongly electron withdrawing groups (e.g., tetrachlorophenols), phosphates, phosphonates, phosphinates, sulphates, sulphonates, thiocarboxylates, and hydroxamic acids.

In an embodiment, the present methods and compositions can employ a scaffold including a group that can hydrogen bond, either as donor or acceptor (e.g., a second hydrogen bonding group). For example, the scaffold can include one or more carboxyl groups, amine groups, hydroxyl groups, carbonyl groups, or the like. Ionic groups can also participate in hydrogen bonding.

In an embodiment, the scaffold includes multiple reaction sites with orthogonal and reliable functional groups and with controlled stereochemistry. Suitable functional groups with orthogonal and reliable chemistries include, for example, carboxyl, amine, hydroxyl, phenol, carbonyl, and thiol groups, which can be individually protected, deprotected, and derivatized. In an embodiment, the scaffold has a number of functional groups with orthogonal and reliable chemistries, wherein the number of functional groups equals or exceeds the number of building blocks to be coupled to the scaffold. In an embodiment, the number of building blocks to be coupled exceeds the number of functional groups. In an embodiment, the scaffold has two, three, four, five, six, or more functional groups with orthogonal and reliable chemistries. In an embodiment, the scaffold has three functional groups. In such an embodiment, the three functional groups can be independently selected, for example, from carboxyl, amine, hydroxyl, phenol, carbonyl, or thiol group.

In an embodiment, a scaffold molecule forms or can be visualized as forming a covalent bond with an alcohol, phenol, thiol, amine, carbonyl, or like group on the linker or framework of each of a plurality of building blocks. The linker or framework can include a carboxyl, alcohol, phenol, thiol, amine, carbonyl, maleimide, or like group that can react with or be activated to react with the scaffold.

The scaffold can include a good leaving group bonded to, for example, an alkyl or aryl group. The leaving group being "good" enough to be displaced by the alcohol, phenol, thiol, amine, carbonyl, or like group on the framework or linker. Such a scaffold can include a moiety represented by the formula: R—X, in which X is a leaving group such as halogen (e.g., —Cl, —Br or —I), tosylate, mesylate, triflate, and R is alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

The scaffold can interact with the ligand as part of the artificial receptor. The scaffold can also provide bulk, hydrophobicity, hydrophilicity, flexibility, rigidity, and like structural characteristics to the artificial receptor. The scaffold can also control proximity, density, and orientation of the building blocks, as further described below.

A scaffold supports an artificial receptor including a combination of 2, 3, 4, 5, 6, 7, or more building blocks occupying distinct positions relative to one another on the scaffold. For example, building block 1 can be adjacent to any of building blocks 2, 3, or 4, etc. . . . This can be illustrated by considering the building blocks coupled to different functional groups on a scaffold. Scaffold positional isomer artificial receptors can be made, for example, on a scaffold with multiple functional groups that can be protected and deprotected by orthogonal chemistries. In an embodiment, the functional group at each reaction side is protected and deprotected by orthogonal chemistries. In an embodiment, a scaffold supports an artificial receptor including heterogeneous building blocks. In an embodiment, scaffolds can include functional groups for coupling to, for example, 2, 3, 4, 5, 6, or 7 building blocks.

In an embodiment, the region in which the building blocks are coupled to the scaffold comprises a reaction site (distinct position) for each building block. Each reaction site on the scaffold comprises a functional group suitable for coupling a building block. The number of distinct positions and relative spacing of the functional groups at the distinct positions can be used to select a scaffold based on desired characteristics of the artificial receptors. The scaffold can be selected to provide a density of building blocks sufficient to provide interactions of more than one building block with a ligand. In an embodiment, the scaffold can be selected to place the building blocks in proximity to one another on the scaffold. Evidence of proximity of different building blocks on a scaffold is provided by altered (e.g., tighter or looser) binding of a ligand to a scaffold with a plurality of building blocks compared to the scaffold with only one of the building blocks.

In an embodiment, the building blocks coupled to the scaffold are commonly oriented towards the potential ligand binding site. The orientation of the building blocks is partly controlled by the scaffold. For example, e.g., substituents on phenyl rings are equatorial, while substituents on cycloalkyls predictably transition between axial and equatorial positions.

Less constrained systems, such as linear alkyls provide additional degrees of freedom (e.g. bond rotation) allowing a larger number of conformers. The effect on relative proximity and orientation of the distinct positions for coupling by the scaffold on building blocks is greatest for building blocks directly coupled to the scaffold. In an embodiment, a scaffold providing distinct positions for coupling (reaction sites) on a common face of the scaffold can be selected to assist in commonly orienting the building blocks. In an embodiment, a scaffold can provide reaction sites on both faces of a planar scaffold. Where the building block and scaffold are coupled via linkers, or flexible framework, there is less control over orientation of the building block and proximity of the building blocks is additionally controlled by the length and flexibility of the linker, framework and scaffold flexibility.

In an embodiment, the scaffold is flexible. In an embodiment, the scaffold is a substituted alkane. In the absence of rings, double bonds, and bulky substituent groups, the bonds within an alkyl chain will generally rotate, allowing an abundance of scaffold conformers. Additional examples of flexible scaffolds include substituted cyclohexane and other cycloalkanes (greater than $C_5$) or polycycloalkanes. The conformational mobility in cyclohexane and derivatives thereof has been extensively studied. A cyclohexane ring, dependent on the bulk of the substituents, transitions from chair$_1$ to boat to chair$_2$, thereby inverting the axial and equatorial positions. The flexibility in the ring allows for various conformations, thereby changing the proximity and orientation of the building blocks. In an embodiment, building blocks are preferably positioned on alternate carbons in cycloalkanes to allow concerted axial orientation.

In an embodiment, the scaffold can be a polyamine, for example, a cyclic alkyl molecule with a plurality of primary amine groups around the ring. Such a scaffold can include a plurality of building blocks coupled to the amines.

Aromatic ring systems, for example, substituted phenyl rings, substituted napthyl rings, or porphyrins (tetrapyroles, e.g., protoporphyrin IX, or Fe(II)heme), provide more rigid, generally planar scaffolds. In these systems, because substituents are preferably equatorially positioned in the plane of the ring(s), in an embodiment each building block is coupled to the scaffold via a flexible linker or framework of sufficient length and flexibility to allow the building blocks to reach and potentially bind a ligand positioned above or below the plane of the conjugated ring system.

In an embodiment, building blocks can be noncovalently coupled to a scaffold using hydrophobic interactions. For example, a scaffold derivatized with a plurality of hydrophobic groups, such as saturated $C_{18}$ chains, will associate with similar hydrophobic groups on one or more building blocks, thereby coupling the building blocks to the scaffold. In an embodiment, building blocks with lipophilic groups can be non-covalently coupled to large scaffolds, such as liposomes, micelles, dendrimers, and membranes.

In an embodiment, the scaffold includes a lipophilic moiety (e.g., a first lipophilic moiety). Suitable lipophilic moieties include branched or straight chain $C_{6-36}$ alkyl, $C_{8-24}$ alkyl, $C_{12-24}$ alkyl, $C_{12-18}$ alkyl, or the like; $C_{6-36}$ alkenyl, $C_{8-24}$ alkenyl, $C_{12-24}$ alkenyl, $C_{12-18}$ alkenyl, or the like, with, for example, 1 to 4 double bonds; $C_{6-36}$ alkynyl, $C_{8-24}$ alkynyl, $C_{12-24}$ alkynyl, $C_{12-18}$ alkynyl, or the like, with, for example, 1 to 4 triple bonds; chains with 1-4 double or triple bonds; chains including aryl or substituted aryl moieties (e.g., phenyl or naphthyl moieties at the end or middle of a chain); polyaromatic hydrocarbon moieties; cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. A lipophilic moiety like a quaternary ammonium lipophilic moiety can also include a positive charge.

In an embodiment, one or more building blocks can be coupled to the scaffold utilizing host-guest interactions. In an embodiment, a scaffold comprises a host moiety and the building block comprises a corresponding guest moiety. In an embodiment, a building block comprises a host moiety and the scaffold comprises a corresponding guest moiety. Examples of host-guest pairs include: crown ethers which complex positive ions (metallic, ammonium or substituted ammonium); Other hosts with binding similar to crown ethers include: macrocyclic and bicyclic compounds containing nitrogen or sulfur or more than one kind of hetero atom (also called cryptands); pherands, calixarenes, cryptophanes, hemispherands, podands, lariat ethers and starands. (Smith, B. and March, J., (2001) "March's Advanced Organic Chemistry." 5th Ed., John Wiley & Sons, Inc.) The strongest host-guest interactions occur when combination of the guest with the host causes the least amount of distortion of the host. Cyclodextrins are also host molecules that form channel or cage complexes with an internalized guest by Van der Waals forces. Suitable guests are for example nonpolar organic molecules matched in size to the internal space in the cyclodextrin.

In an embodiment, the scaffold can be selected for properties affecting solubility, such as hydrophobicity or hydrophilicity. In an embodiment, a scaffold artificial receptor is soluble in solution, for example aqueous solution. In an embodiment, the solubility of the scaffold is selected for the solution conditions where ligand binding to the artificial receptor is desired. In an embodiment utilizing aqueous solutions, selection of a scaffold with hydrophilic properties is preferred for a soluble scaffold artificial receptor. In an embodiment, a scaffold with hydrophobic properties can be selected if association of the scaffold with a hydrophobic environment is desired. For example a hydrophobic scaffold may encourage aggregation in aqueous solution, association with a lipid bilayer or micelle, or solubility in a non-polar solvent.

In an embodiment, a scaffold can include a portion having a plurality of building blocks that is independent and distinct from other portions, also including a plurality of building blocks. In an embodiment, one or more regions including a plurality of building blocks can overlap to produce a region including the combined pluralities of building blocks. In an embodiment, two or more portions including a single building block can overlap to form one or more portions each including a plurality of building blocks. In an embodiment, at least one of the building blocks includes a tether moiety. The overlapping regions can be envisioned, for example, as portions of overlap in a Venn diagram, or as portions of overlap in a pattern like a plaid or tweed. In an embodiment, scaffolds having one or more portions, each portion having a plurality of building blocks, are large molecules in excess of approximately 1 nanometer in diameter.

In an embodiment, the scaffold molecule can be any of the variety of known molecular scaffolds employed in combinatorial research. Suitable scaffold molecules include those illustrated in Scheme 6. The compounds illustrated in Scheme 6 are either commercially available or can be made by known methods. For example, compounds 1, 2, 4, 5, and 12 are commercially available from Aldrich. Compound 3 can be prepared by the method of Pattarawarapan (2000)(Pattarawarapan, M and Burgess, K, "A Linker Scaffold to Present Dimers of Pharmacophores Prepared by Solid-Phase Synthesis", Angew. Chem. Int. Ed., 39, 4299-4301 (2000)). Compound 6 can be made in the o-NH$_2$ form (shown) by the method of Kimura (2001)(Kimura, M; Shiba, T; Yamazaki, M; Hanabusa, K; Shirai, H and Kobayashi, N, "Construction of Regulated Nanospace around a Porphyrin Core", J. Am. Chem. Soc., 123, 5636-5642 (2001)) and in the p-COOH (not shown) by the method of Jain (2000)(Jain, R K; Hamilton, A D (2000), "Protein Surface Recognition by Synthetic Receptors Based on a Tetraphenylporphyrin Scaffold", Org. Lett. 2, pp. 1721-1723). Compound 7 can be made in the —COOH form (shown) or in the —OH form (not shown) by the method of Hamuro (1997)(Hamuro, Y. et al., (Andrew Hamilton), "A Calixarene with four Peptide Loops: An Antibody Mimic for Recognition of Protein Surfaces", Angew. Chem. Int. Ed. Engl., 36, pp. 2680-2683). Compound 8 can be used with three functional groups in the —NH$_2$ form (shown), with four functional groups including both the —COOH and —NH$_2$ groups (as shown), or as a dimer product with 6-NH$_2$ functional groups (not shown). Each of these forms of compound 8 can be made by the method of Opatz (2001) (Opatz, T; Liskamp, R M (2001), "A Selectively Deprotectable Triazacyclophane Scaffold for the Construction of Artificial Receptors", Org. Lett., 3, pp. 3499-3502). Compound 9 can be made by the method of Wong (1988) (Wong, C-H, Hendrix, M, Manning, D D, Rosenbohm, C, Greenberg, W A, (1988), "A Library approach to the discovery of small molecules that recognize RNA: use of a 1,3-hydroxyamine motif as core.", J. Am. Chem. Soc., 120:8319-8327. Compound 10 is a xanthene tetraisocyanate scaffold, which can be made by the method of Shipps (1997)(Shipps, G W, Pryor K E, Xian J, Skyler D A, Davidson E H, Rebek J, "Synthesis and screening of small molecule libraries active in binding to DNA." Proc. Natl. Acad. Sci. USA, (1997), 94:11833-11838). A derivatized calixarene scaffold, such as compound 11, is readily synthesized from commercially available calixarene. (Park H S, Lin Q, Hamilton A D, "Protein surface recognition by synthetic receptors: a route to novel submicromolar inhibitors for chymotrypsin." (1999) J. Am. Chem. Soc., 121:8-13).

For general discussion of scaffolds and further examples, see Srinivasan, N and Kilburn, J D, (2004) "Combinatorial Approaches to Synthetic Receptors", Cur. Op. Chem. Bio., 8:305-310; and Linton, B and Hamilton, D, (1999) "Host-guest Chemistry: Combinatorial Receptors," Curr. Op. Str. Biol., 3:307-312.

Scheme 6

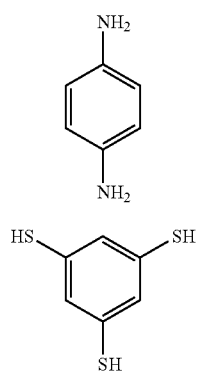

-continued

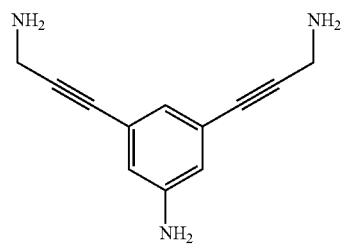
3

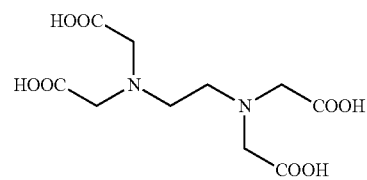
4

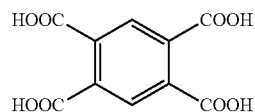
5

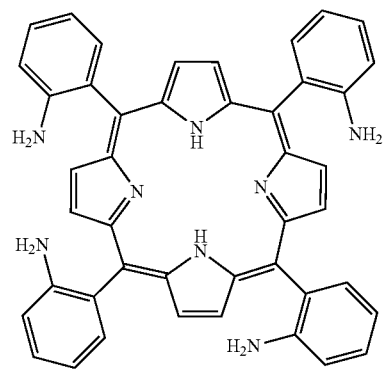
6

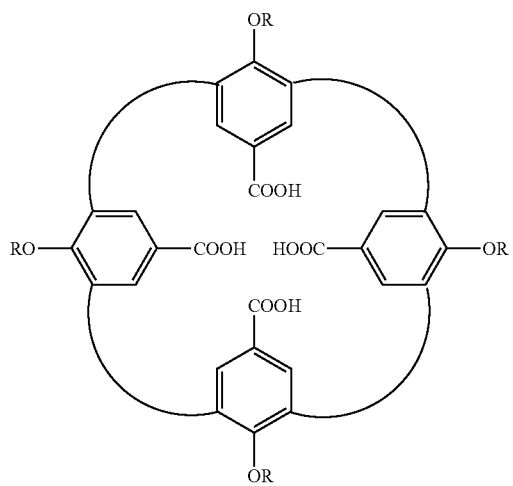
7

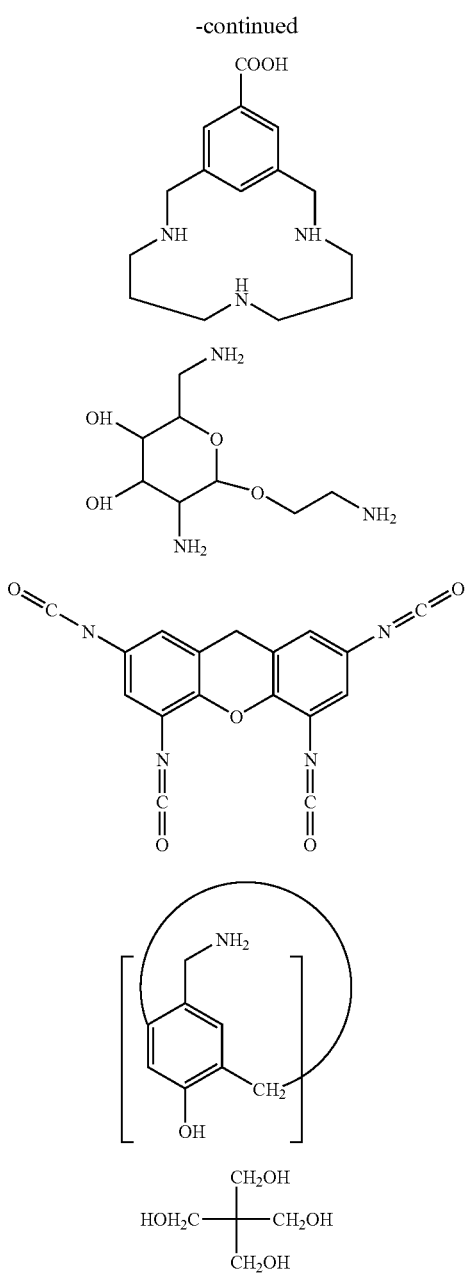

Techniques for Using Artificial Receptors

In an embodiment, the scaffold artificial receptors are in solution. The solution is a homogeneous mixture at the molecular or ionic level, of one or more substances, including scaffold artificial receptors (solute(s)), in one or more other substances (solvent). Solvents can be a substance or mixture that is able to dissolve the solute. Solvents are typically liquid and possess polarity characteristics from polar (e.g., water) to non-polar (e.g., hydrocarbon solvents). Various general examples include: aqueous, alcohols, esters, ethers, ketones, amines, aromatic hydrocarbons, aliphatic hydrocarbons, and nitrated and chlorinated hydrocarbons. Mixtures of miscible solvents may also be used as solvent for solutions including scaffold artificial receptors.

In an embodiment, the solution can include additional solvents and/or solutes to improve solubility of the scaffold artificial receptors. Example additives can include: surfactants, hydrotropes, salts, acids/bases and co-solvents. Interaction of the scaffold artificial receptors in solution may also be altered by additional solvents and/or solutes. For example, to adjust pH, adjust ionic strength, discourage aggregation, prevent precipitation, or discourage/encourage colloid formation.

In an embodiment, the solution is similar in nature to the desired binding environment of ligand to scaffold artifical receptor. The solution can include additional components, including for example: proteins, cells, ions, sugars, etc. . . . For example, for a scaffold articial receptor that binds glucose in blood, either blood or a solution emulating blood can be used. In an embodiment, the scaffold artifical receptors are in an aqueous solution and can include additional solvent or solute components.

In an embodiment, the solution is isolated in a location. A location holds a quantity of solution, where the quantity of solution can comprise one or more scaffold artificial receptors. A location can include: one of a plurality of drops spaced on a support, such as a plate or slide; one of a plurality of pits on a compact disc (CD); or one of a plurality of compartments, on a multi-compartment support, such as a multi-well plate. In an embodiment, a quantity of solution at each location can be about 1 nanoliter (nL) to about 1 microliter (µL).

In an embodiment, the solution at each location comprises a pluralty of homogeneous scaffold artificial receptors. In an embodiment, the solution at each location comprises a pluralty of heterogeneous scaffold artificial receptors. In an embodiment, the solution at each location comprises a single homogeneous scaffold artificial receptor. In an embodiment, the solution at each location comprises a single of heterogeneous scaffold artificial receptor.

The present invention includes a method of using artificial receptors. The present invention includes a method of screening candidate artificial receptors to find lead artificial receptors that bind a particular test ligand. Detecting test ligand bound to a candidate artificial receptor can be accomplished using known methods for detecting binding. For example, the method can employ test ligand labeled with a detectable label, such as a fluorophore or an enzyme that produces a detectable product. Alternatively, the method can employ an antibody (or other binding agent) specific for the test ligand and including a detectable label. In an embodiment, the scaffold artificial receptors in solution are in locations on a support. Each location may include one or more scaffold artificial receptors. The particular test ligand is added to each location. One or more of the locations that are labeled by the test ligand or that are more or most intensely labeled with the test ligand are selected as lead artificial receptors. The degree of labeling can be evaluated by evaluating the signal strength from the label. The amount of signal can be directly proportional to the amount of label and binding.

In an embodiment, the scaffold artificial receptor is made by coupling the building blocks to a scaffold in solution in a location on a support. The scaffold artificial receptors at each location can vary in identity of the building blocks and/or identity of the scaffold. Each location contains a different population of scaffold artificial receptors. The population of scaffold artificial receptors can be zero (e.g., a control), one, and greater than one, to an upper limit dependent on saturation of the solution. In an embodiment, the population is less than 1 M. In an embodiment, the population is less than 1 µM. In an embodiment, the population is less than 1 nM. In an embodiment, the population is less than 1 pM. In a further embodiment, the artificial receptor is screened for ligand binding in the locations on a support.

According to the present method, screening candidate artificial receptors against a test ligand can yield one or more lead artificial receptors. One or more lead artificial receptors can be a working artificial receptor. That is, the one or more lead artificial receptors can be useful for detecting the ligand of interest as is. The method can then employ the one or more artificial receptors as a working artificial receptor for monitoring or detecting the test ligand. Alternatively, the one or more lead artificial receptors can be employed in the method for developing a working artificial receptor. For example, the one or more lead artificial receptors can provide structural or other information useful for designing or screening for an improved lead artificial receptor or a working artificial receptor. Such designing or screening can include making and testing additional candidate artificial receptors including combinations of a subset of building blocks, a different set of building blocks, or a different number of building blocks.

The present invention includes a method of screening candidate artificial receptors to find lead artificial receptors that bind a particular test ligand. The method can include allowing movement of the building blocks that make up the artificial receptors. Movement of building blocks can include mobilizing the building block to move along or on the scaffold and/or to leave the scaffold and enter a fluid (e.g., liquid) phase separate from the scaffold or lawn.

In an embodiment, building blocks can be mobilized to move along or on the scaffold (translate or shuffle). Such translation can be employed, for example, to allow building blocks already bound to a test ligand to rearrange into a lower energy or tighter binding configuration still bound to the test ligand. Such translation can be employed, for example, to allow the ligand access to building blocks that are on the scaffold but not bound to the ligand. These building blocks can translate into proximity with and bind to a test ligand.

Building blocks can be induced to move along or on the scaffold or to be reversibly immobilized on the scaffold through any of a variety of mechanisms. For example, inducing mobility of building blocks can include altering the conditions of the scaffold or lawn. That is, altering the conditions can reverse the immobilization of the building blocks, thus mobilizing them. Reversibly immobilizing the building blocks after they have moved can include, for example, returning to the previous conditions. Suitable alterations of conditions include changing pH, changing temperature, changing polarity or hydrophobicity, changing ionic strength, changing nucleophilicity or electrophilicity (e.g. of solvent or solute), and the like.

A building block reversibly immobilized by hydrophobic interactions can be mobilized by increasing the temperature, by exposing the scaffold, or building block to a more hydrophobic solvent (e.g., an organic solvent or a surfactant), or by reducing ionic strength around the building block. In an embodiment, the organic solvent includes acetonitrile, acetic acid, an alcohol, tetrahydrofuran (THF), dimethylformamide (DMF), hydrocarbons such as hexane or octane, acetone, chloroform, methylene chloride, or the like, or mixture thereof. In an embodiment, the surfactant includes a nonionic surfactant, such as a nonylphenol ethoxylate, or the like. A building block that is mobile on a scaffold can be reversibly immobilized by hydrophobic interactions, for example, by decreasing the temperature, exposing the scaffold, or building block to a more hydrophilic solvent (e.g., an aqueous solvent) or increased ionic strength.

A building block reversibly immobilized by hydrogen bonding can be mobilized by increasing the ionic strength, concentration of hydrophilic solvent, or concentration of a competing hydrogen bonder in the environs of the building block. A building block that is mobile on a scaffold can be reversibly immobilized through an electrostatic interaction by decreasing ionic strength of the hydrophilic solvent, or the like.

A building block reversibly immobilized by an electrostatic interaction can be mobilized by increasing the ionic strength in the environs of the building block. Increasing ionic strength can disrupt electrostatic interactions. A building block that is mobile on a scaffold can be reversibly immobilized through an electrostatic interaction by decreasing ionic strength.

A building block reversibly immobilized by an imine, acetal, or ketal bond can be mobilized by decreasing the pH or increasing concentration of a nucleophilic catalyst in the environs of the building block. In an embodiment, the pH is about 1 to about 4. Imines, acetals, and ketals undergo acid catalyzed hydrolysis. A building block that is mobile on a scaffold can be reversibly immobilized by a reversible covalent interaction, such as by forming an imine, acetal, or ketal bond, by increasing the pH.

In an embodiment, building blocks can be mobilized to leave the scaffold and enter a fluid (e.g., liquid) phase separate from the scaffold (exchange). For example, building blocks can be exchanged onto and/or off of the scaffold. Exchange can be employed, for example, to allow building blocks on a scaffold but not bound to a test ligand to be removed from the scaffold. Exchange can be employed, for example, to add additional building blocks to the scaffold. The added building blocks can have structures selected based on knowledge of the structures of the building blocks in artificial receptors that bind the test ligand. The added building blocks can have structures selected to provide additional structural diversity. The added building blocks can include all of the building blocks.

A building block reversibly immobilized by hydrophobic interactions can be released from the scaffold by, for example, raising the temperature, e.g., of the scaffold and/or artificial receptor. For example, the hydrophobic interactions (e.g., the hydrophobic group on the scaffold and on the building block) can be selected to provide immobilized building block at about room temperature or below and release can be accomplished at a temperature above room temperature. For example, the hydrophobic interactions can be selected to provide immobilized building block at about refrigerator temperature (e.g., 4° C.) or below and release can be accomplished at a temperature of, for example, room temperature or above. By way of further example, a building block can be reversibly immobilized by hydrophobic interactions, for example, by contacting the surface or artificial receptor with a fluid containing the building block and that is at or below room temperature.

A building block reversibly immobilized by hydrophobic interactions can be released from the scaffold by, for example, contacting the artificial receptor with a sufficiently hydrophobic fluid (e.g., an organic solvent or a surfactant). In an embodiment, the organic solvent includes acetonitrile, acetic acid, an alcohol, tetrahydrofuran (THF), dimethylformamide (DMF), hydrocarbons such as hexane or octane, acetone, chloroform, methylene chloride, or the like, or mixture thereof. In an embodiment, the surfactant includes a nonionic surfactant, such as a nonylphenol ethoxylate, or the like.

A building block reversibly immobilized by an imine, acetal, or ketal bond can be released from the scaffold by, for example, contacting the artificial receptor with fluid having an acid pH or including a nucleophilic catalyst. In an embodiment, the pH is about 1 to about 4. A building block can be reversibly immobilized by a reversible covalent interaction, such as by forming an imine, acetal, or ketal bond, by contacting the surface or artificial receptor with fluid having a neutral or basic pH.

A building block reversibly immobilized by an electrostatic interaction can be released by, for example, contacting the artificial receptor with fluid having sufficiently high ionic strength to disrupt the electrostatic interaction. A building block can be reversibly immobilized through an electrostatic interaction by contacting the surface or artificial receptor with fluid having ionic strength that promotes electrostatic interaction between the building block and the scaffold and/or lawn.

The above specification, examples and data provide a complete description of the manufacture and use of the composition of the invention. Since many embodiments of the invention can be made without departing from the spirit and scope of the invention, the invention resides in the claims hereinafter appended.

The present invention may be better understood with reference to the following examples. These examples are intended to be representative of specific embodiments of the invention, and are not intended as limiting the scope of the invention.

EXAMPLES

Example 1

Synthesis of Building Blocks

Selected building blocks representative of the alkyl-aromatic-polar span of the an embodiment of the building blocks were synthesized and demonstrated effectiveness of these building blocks for making candidate artificial receptors. These building blocks were made on a framework that can be represented by tyrosine and included numerous recognition element pairs. These recognition element pairs include enough of the range from alkyl, to aromatic, to polar to represent a significant degree of the interactions and functional groups of the full set of 81 such building blocks.

Synthesis

Building block synthesis employed a general procedure outlined in Scheme 7, which specifically illustrates synthesis of a building block on a tyrosine framework with recognition element pair A4B4. This general procedure was employed for synthesis of building blocks including TyrA1B1 [1-1], TyrA2B2, TyrA2B4, TyrA2B6, TyrA2B8, TyrA4B2, TyrA4B4, TyrA4B6, TyrA4B8, TyrA6B2, TyrA6B4, TyrA6B6, TyrA6B8, TyrA8B2, TyrA8B4, TyrA8B6, TyrA8B8, and TyrA9B9, respectively.

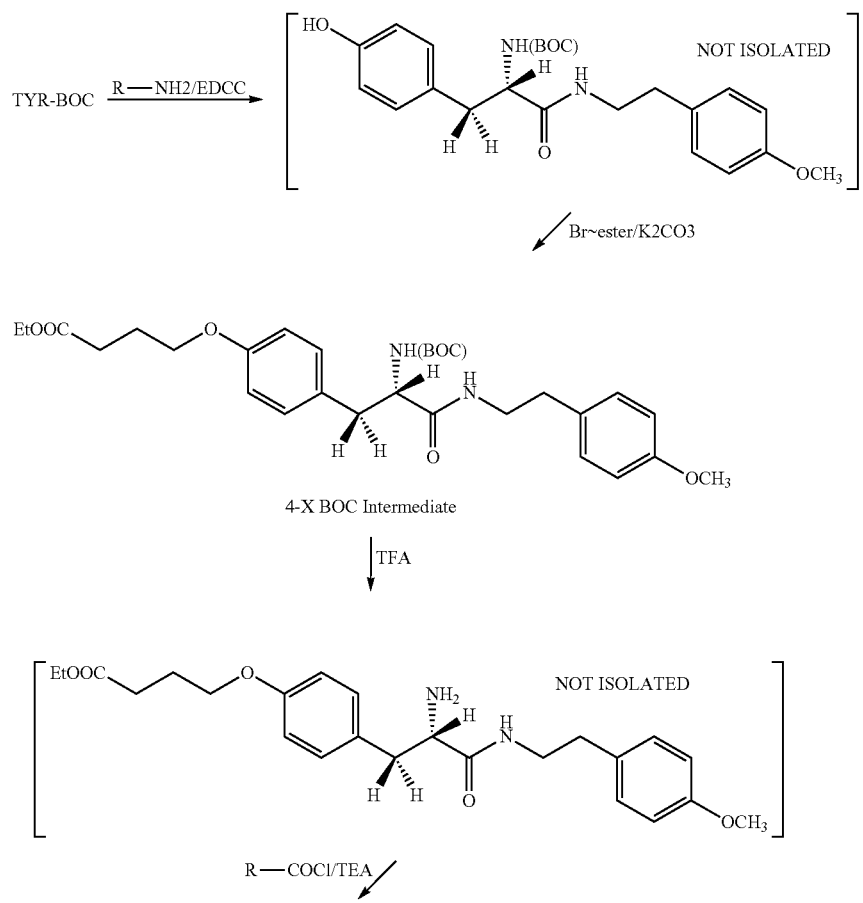

Scheme 7

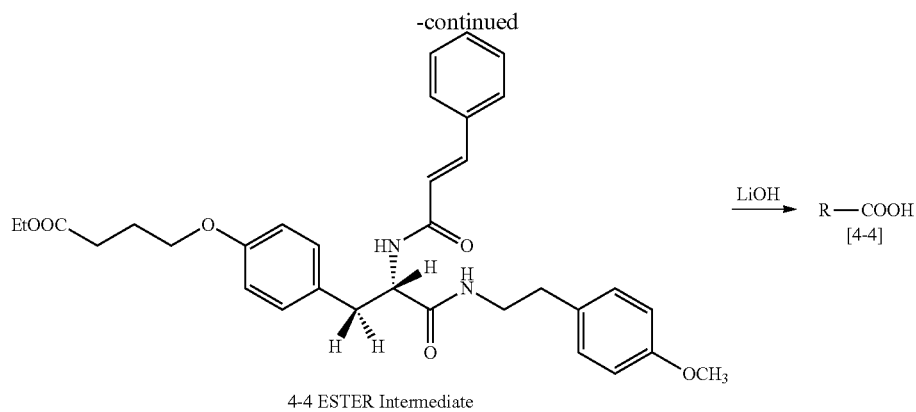

4-4 ESTER Intermediate

Results

Synthesis of the desired building blocks proved to be generally straightforward. These syntheses illustrate the relative simplicity of preparing the building blocks with 2 recognition elements having different structural characteristics or structures (e.g. A4B2, A6B3, etc.) once the building blocks with corresponding recognition elements (e.g. A2B2, A4B4, etc) have been prepared via their X BOC intermediate.

The conversion of one of these building blocks to a building block with a lipophilic linker can be accomplished by reacting the activated building block with, for example, dodecyl amine.

Example 2

Preparation and Evaluation of Microarrays of Candidate Artificial Receptors

Microarrays of candidate artificial receptors were made and evaluated for binding several protein ligands. The results obtained demonstrate the 1) the simplicity with which microarrays of candidate artificial receptors can be prepared, 2) binding affinity and binding pattern reproducibility, 3) significantly improved binding for building block heterogeneous receptor environments when compared to the respective homogeneous controls, and 4) ligand distinctive binding patterns (e.g., working receptor complexes).

Materials and Methods

Building blocks were synthesized and activated as described in Example 1. The building blocks employed in this example were TyrA1B1 [1-1], TyrA2B2, TyrA2B4, TyrA2B6, TyrA4B2, TyrA4B4, TyrA4B6, TyrA6B2, TyrA6B4, and TyrA6B6. The abbreviation for the building block including a linker, a tyrosine framework, and recognition elements AxBy is TyrAxBy.

Microarrays for the evaluation of the 130 n=2 and n=3, and for evaluation of the 273 n=2, n=3, and n=4, candidate receptor environments were prepared as follows by modifications of known methods. As used herein, "n" is the number of different building blocks employed in a receptor environment. Briefly: Amine modified (amine "lawn"; SuperAmine Microarray plates) microarray plates were purchased from Telechem Inc., Sunnyvale, Calif. (www.arrayit.com). These plates were manufactured specifically for microarray preparation and had a nominal amine load of 2-4 amines per square nm according to the manufacturer. The CAM microarrays were prepared using a pin microarray spotter instrument from Telechem Inc. (SpotBot™ Arrayer) typically with 200 um diameter spotting pins from Telechem Inc. (Stealth Micro Spotting Pins, SMP6) and 400-420 um spot spacing.

The 9 building blocks were activated in aqueous dimethylformamide (DMF) solution as described above. For preparing the 384-well feed plate, the activated building block solutions were diluted 10-fold with a solution of DMF/H$_2$O/PEG400 (90/10/10, v/v/v; PEG400 is polyethylene glycol nominal 400 FW, Aldrich Chemical Co., Milwaukee, Wis.). These stock solutions were aliquotted (10 μl per aliquot) into the wells of a 384-well microwell plate (Telechem Inc.). A separate series of controls were prepared by aliquotting 10 μl of building block with either 10 μl or 20 μl of the activated [1-1] solution. The plate was covered with aluminum foil and placed on the bed of a rotary shaker for 15 minutes at 1,000 RPM. This master plate was stored covered with aluminum foil at −20° C. when not in use.

For preparing the 384-well SpotBot™ plate, a well-to-well transfer (e.g. A-1 to A-1, A-2 to A-2, etc.) from the feed plate to a second 384-well plate was performed using a 411 transfer pipette. This plate was stored tightly covered with aluminum foil at −20° C. when not in use. The SpotBot™ was used to prepare up to 13 microarray plates per run using the 4 μl microwell plate. The SpotBot™ was programmed to spot from each microwell in quadruplicate. The wash station on the SpotBot™ used a wash solution of EtOH/H2O (20/80, v/v). This wash solution was also used to rinse the microarrays on completion of the SpotBot™ printing run. The plates were given a final rinse with deionized (DI) water, dried using a stream of compressed air, and stored at room temperature.

Certain of the microarrays were further modified by reacting the remaining amines with succinic anhydride to form a carboxylate lawn in place of the amine lawn.

The following test ligands and labels were used in these experiments:

1) r-Phycoerythrin, a commercially available and intrinsically fluorescent protein with a FW of 2,000,000.

2) Ovalbumin labeled with the Alexa™ fluorophore (Molecular Probes Inc., Eugene, Oreg.).

3) BSA, bovine serum albumin, labeled with activated Rhodamine (Pierce Chemical, Rockford, Ill.) using the known activated carboxylprotocol. BSA has a FW of 68,000; the material used for this study had ca. 1.0 rhodamine per BSA.

4) Horseradish peroxidase (HRP) modified with extra amines and labeled as the acetamide derivative or with a 2,3,7,8-tetrachlorodibenzodixoin derivative were available through known methods. Fluorescence detection of these HRP conjugates was based on the Alexa 647-tyramide kit available from Molecular Probes, Eugene, Oreg.

5) Cholera toxin labeled with the Alexa™ fluorophore (Molecular Probes Inc., Eugene, Oreg.).

Microarray incubation and analysis was conducted as follows: For test ligand incubation with the microarrays, solutions (e.g. 500 μl) of the target proteins in PBS-T (PBS with 20 μl/L of Tween-20) at typical concentrations of 10, 1.0 and 0.1 μg/ml were placed onto the surface of a microarray and allowed to react for, e.g., 30 minutes. The microarray was rinsed with PBS-T and DI water and dried using a stream of compressed air.

The incubated microarray was scanned using an Axon Model 4200A Fluorescence Microarray Scanner (Axon Instruments, Union City, Calif.). The Axon scanner and its associated software produce a false color 16-bit image of the fluorescence intensity of the plate. This 16-bit data is integrated using the Axon software to give a Fluorescence Units value (range 0-65,536) for each spot on the microarray. This data is then exported into an Excel file (Microsoft) for further analysis including mean, standard deviation and coefficient of variation calculations.

Results

The CARA™: Combinatorial Artificial Receptor Array™ concept has been demonstrated using a microarray format. A CARA microarray based on N=9 building blocks was prepared and evaluated for binding to several protein and substituted protein ligands. This microarray included 144 candidate receptors (18 n=1 controls plus 6 blanks; 36 n=2 candidate receptors; 84 n=3 candidate receptors). This microarray demonstrated: 1) the simplicity of CARA microarray preparation, 2) binding affinity and binding pattern reproducibility, 3) significantly improved binding for building block heterogeneous receptor environments when compared to the respective homogeneous controls, and 4) ligand distinctive binding patterns.

Reading the Arrays

Figure 6:
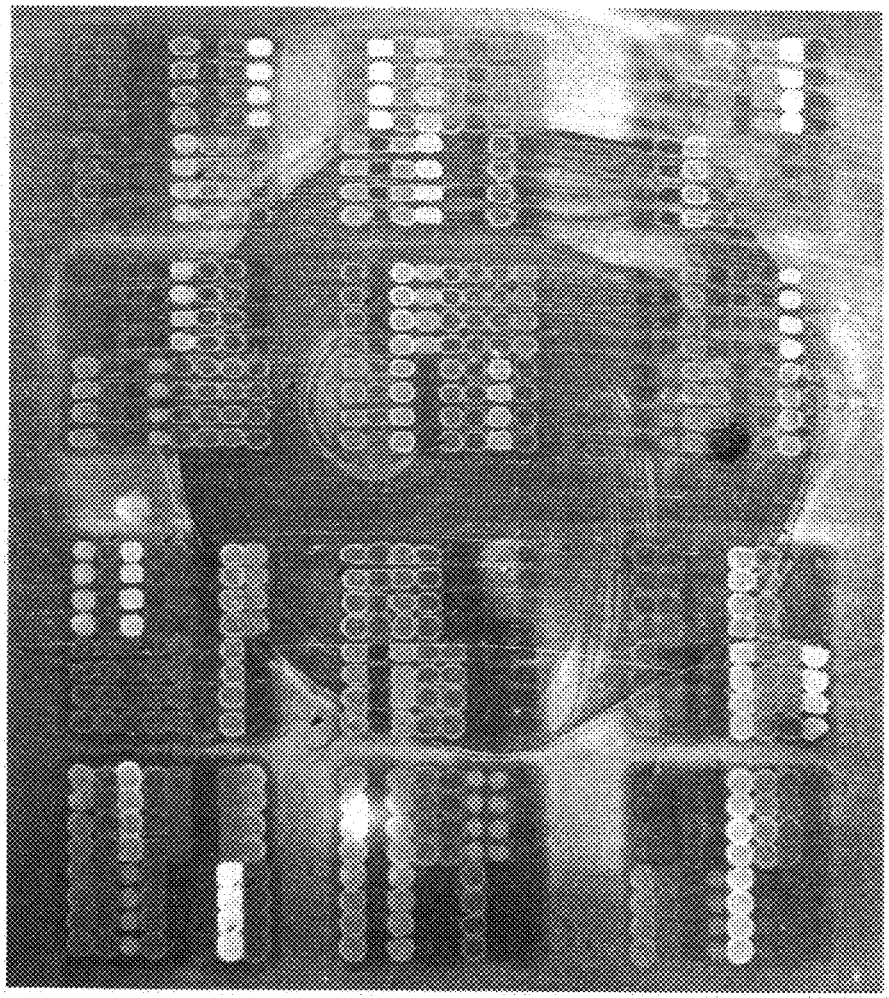
FIG. 6 schematically illustrates a false color fluorescence image of a labeled microarray according to an embodiment of the present invention.

A typical false color/gray scale image of a microarray that was incubated with 2.0 μg/ml r-phycoerythrin is shown in FIG. 6. This image illustrates that the processes of both preparing the microarray and probing it with a protein test ligand produced the expected range of binding as seen in the visual range of relative fluorescence from dark to bright spots.

The starting point in analysis of the data was to take the integrated fluorescence units data for the array of spots and normalize to the observed value for the [1-1] building block control. Subsequent analysis included mean, standard deviation and coefficient of variation calculations. Additionally, control values for homogeneous building blocks were obtained from the building block plus [1-1] data.

First Set of Experiments

The following protein ligands were evaluated for binding to the candidate artificial receptors in the microarray. The resulting Fluorescence Units versus candidate receptor environment data is presented in both a 2D format where the candidate receptors are placed along the X-axis and the Fluorescence Units are shown on the Y-axis and a 3D format where the Candidate Receptors are placed in an X-Y format and the Fluorescence Units are shown on the Z-axis. A key for the composition of each spot was developed (not shown). A key for the building blocks in each of the 2D and 3D representations of the results was also developed (not shown). The data presented are for 1-2 μg/ml protein concentrations.

Figure 7:
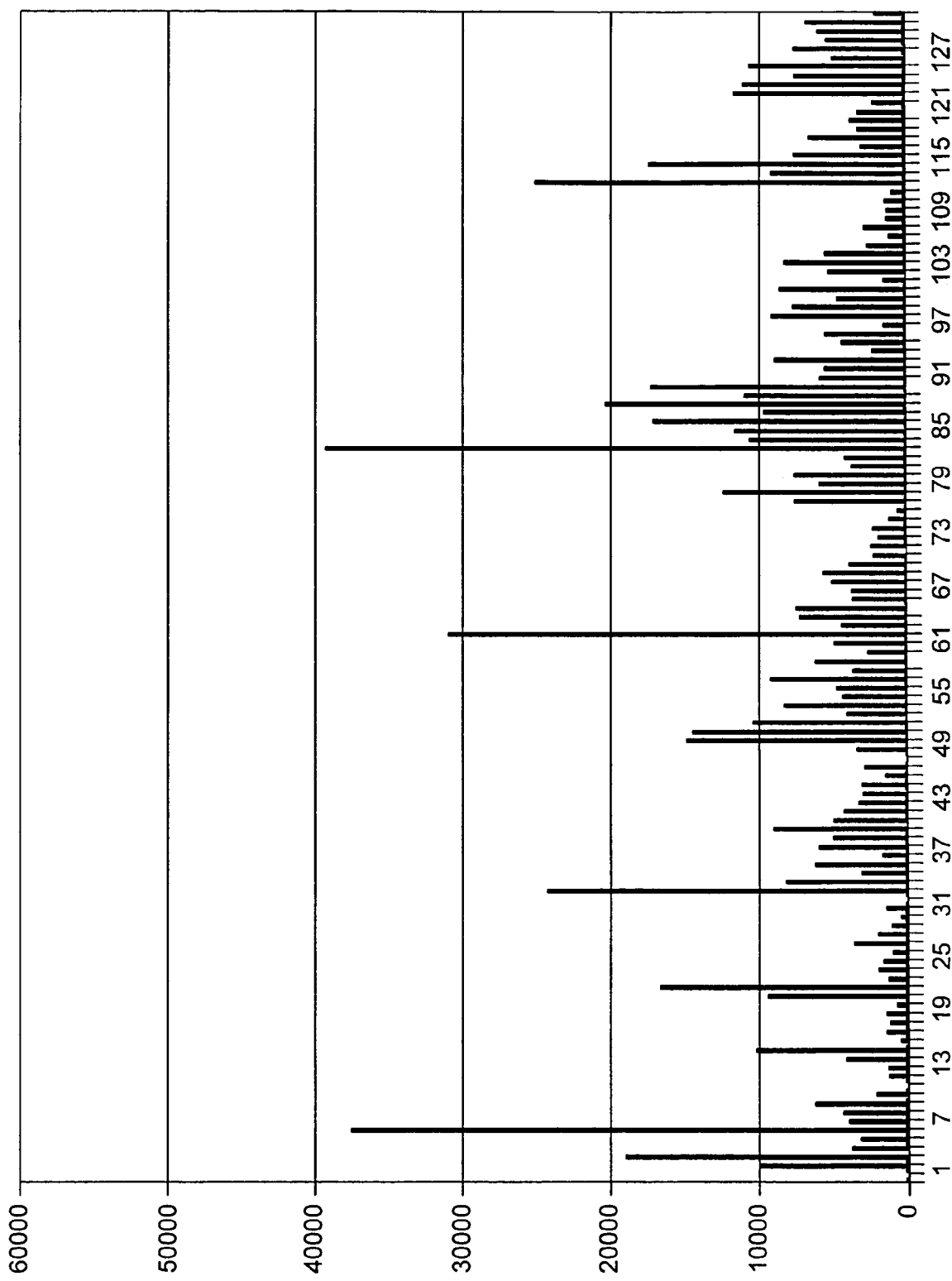
FIG. 7 schematically illustrates a two dimensional plot of data obtained for candidate artificial receptors contacted with and/or binding phycoerythrin.
Figure 8:
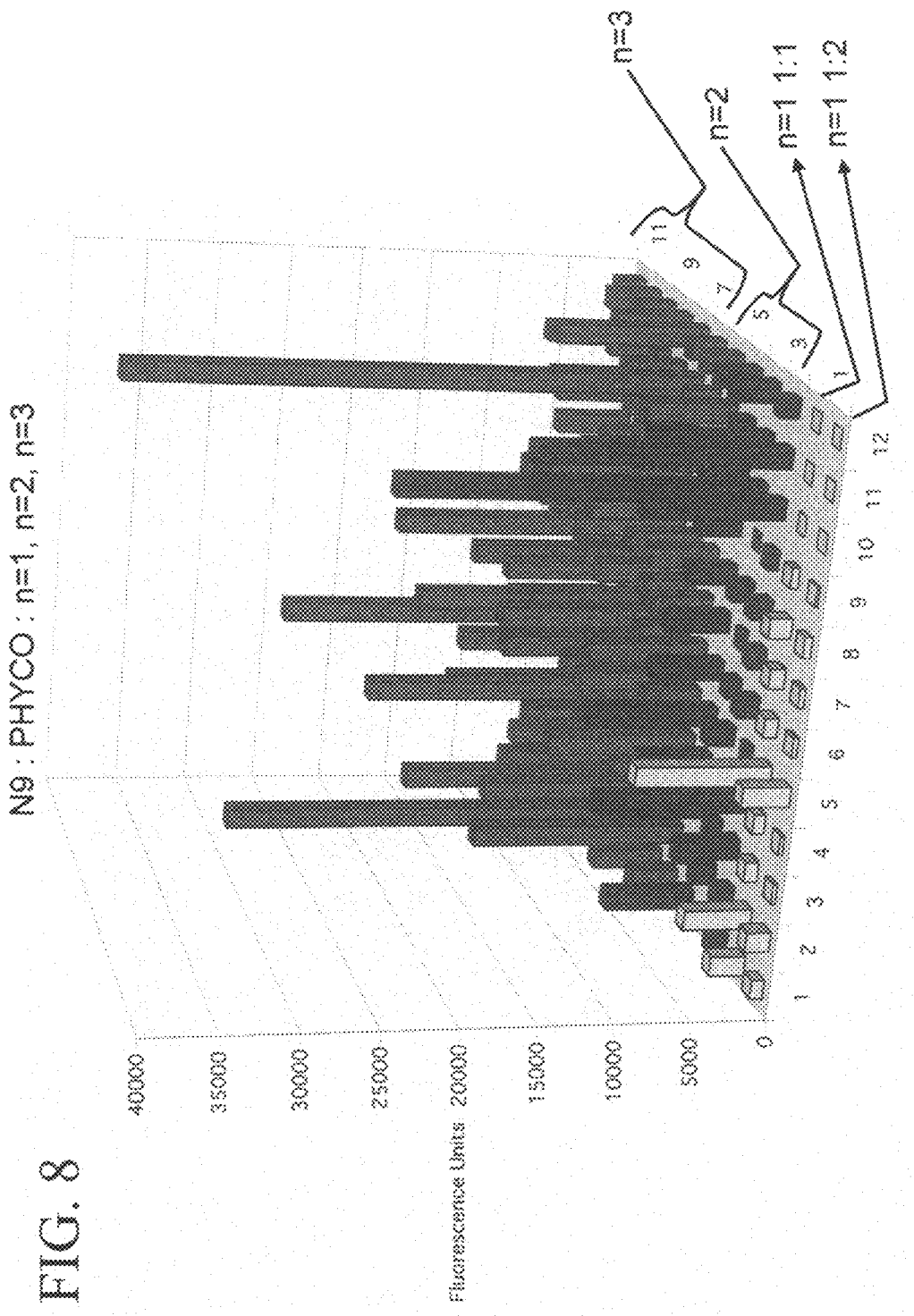
FIG. 8 schematically illustrates a three dimensional plot of data obtained for candidate artificial receptors contacted with and/or binding phycoerythrin.
Figure 9:
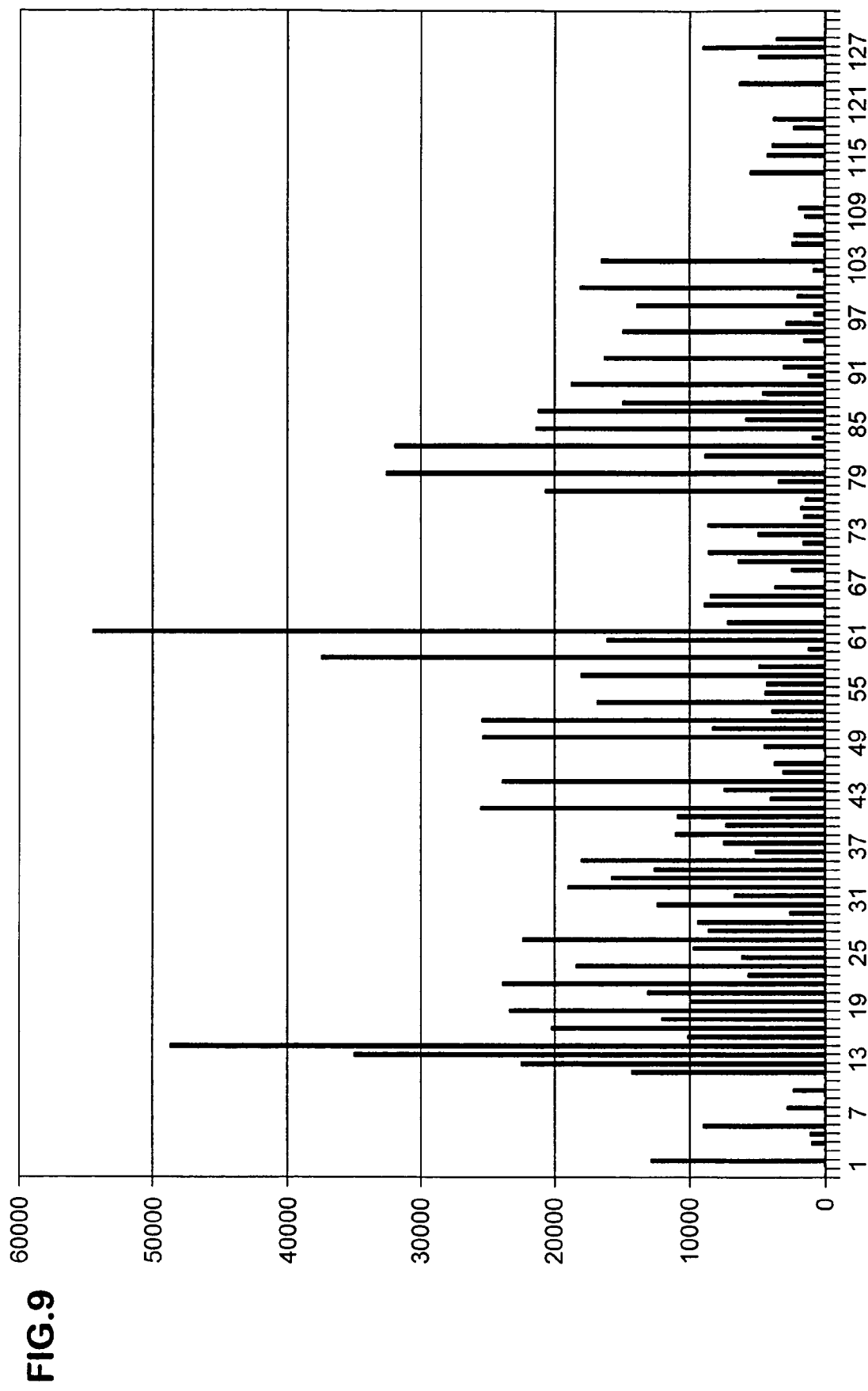
FIG. 9 schematically illustrates a two dimensional plot of data obtained for candidate artificial receptors contacted with and/or binding a fluorescent derivative of ovalbumin.
Figure 10:
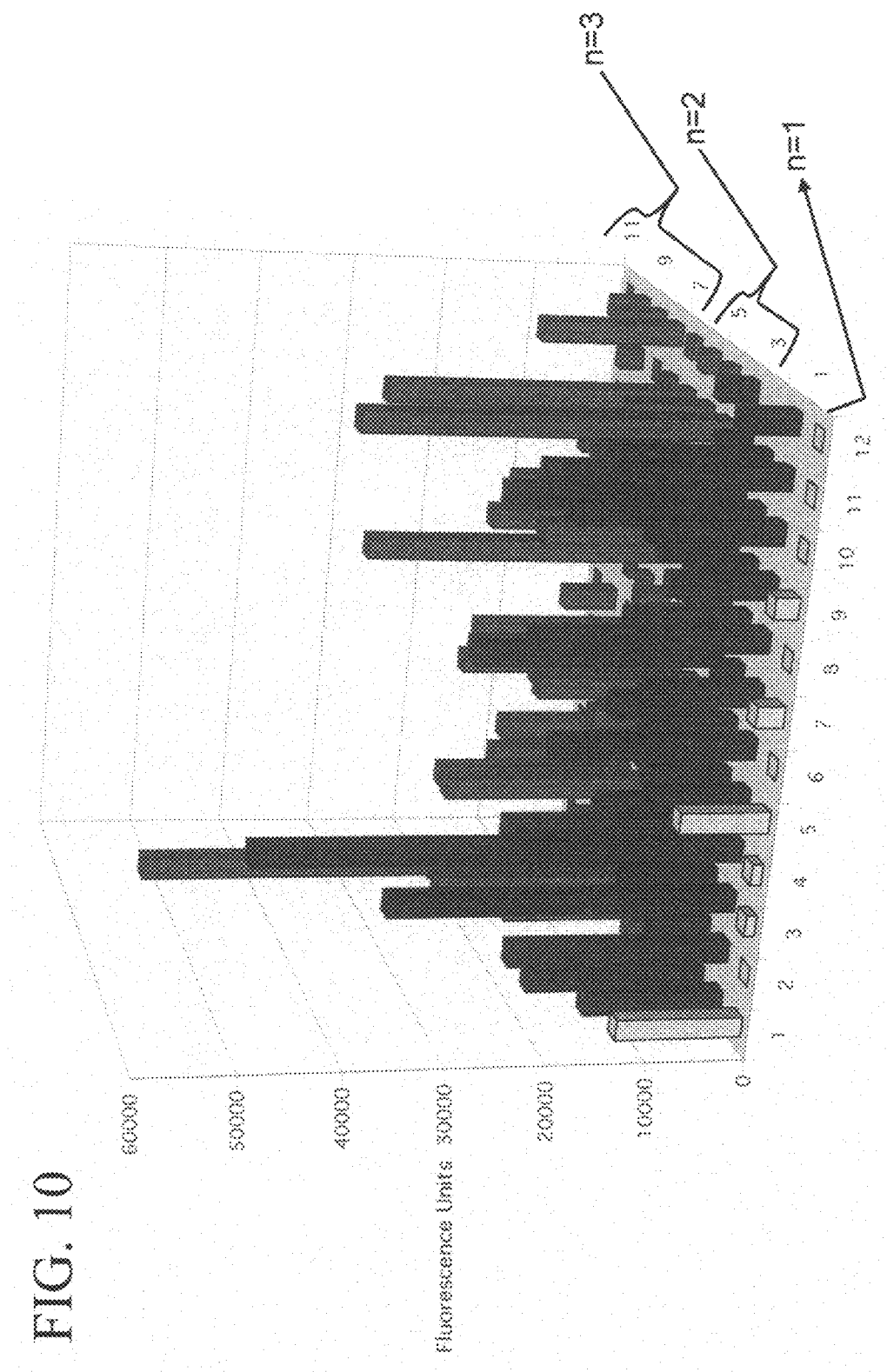
FIG. 10 schematically illustrates a three dimensional plot of data obtained for candidate artificial receptors contacted with and/or binding a fluorescent derivative of ovalbumin.
Figure 11:
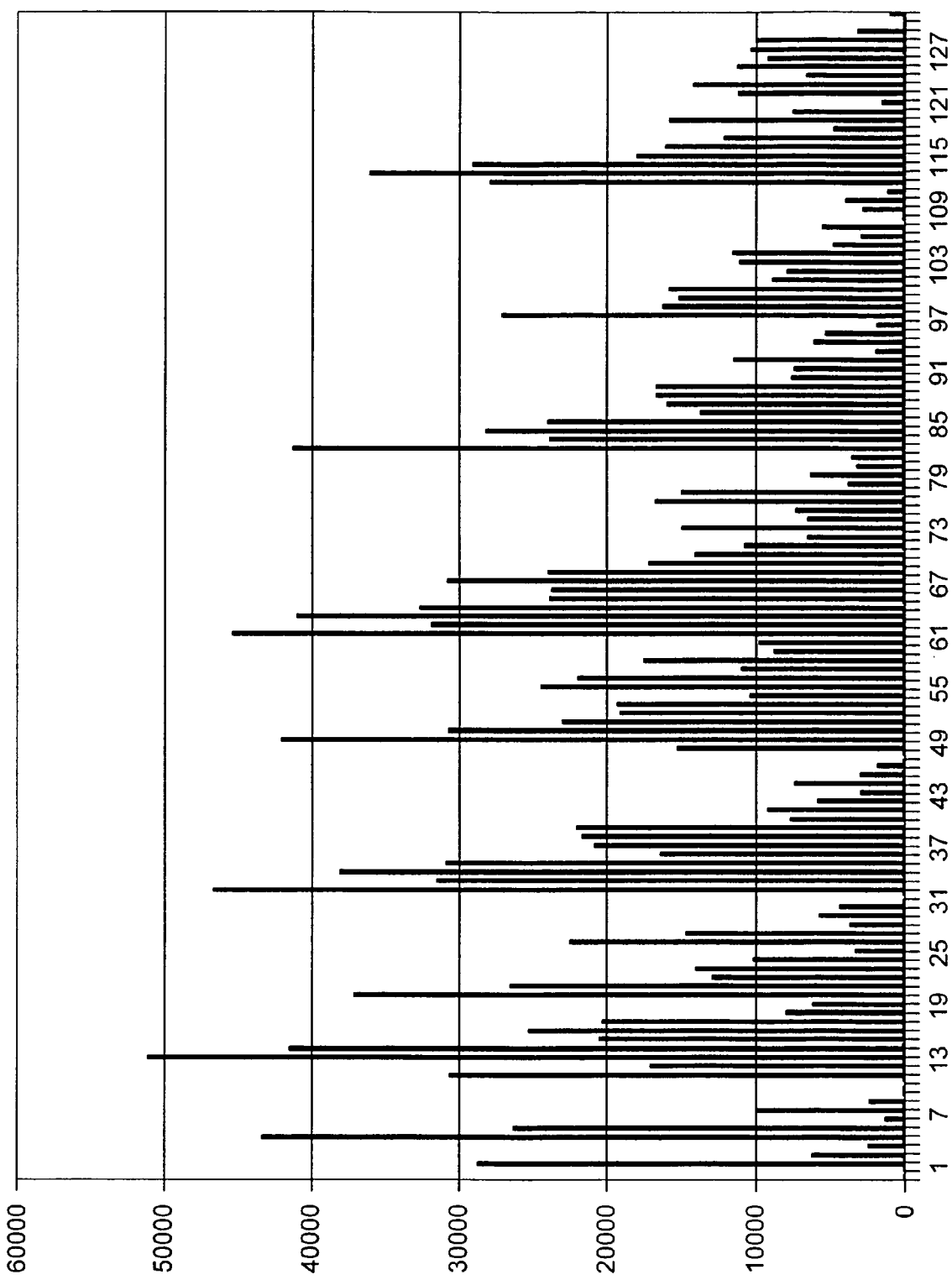
FIG. 11 schematically illustrates a two dimensional plot of data obtained for candidate artificial receptors contacted with and/or binding a fluorescent derivative of bovine serum albumin.
Figure 12:
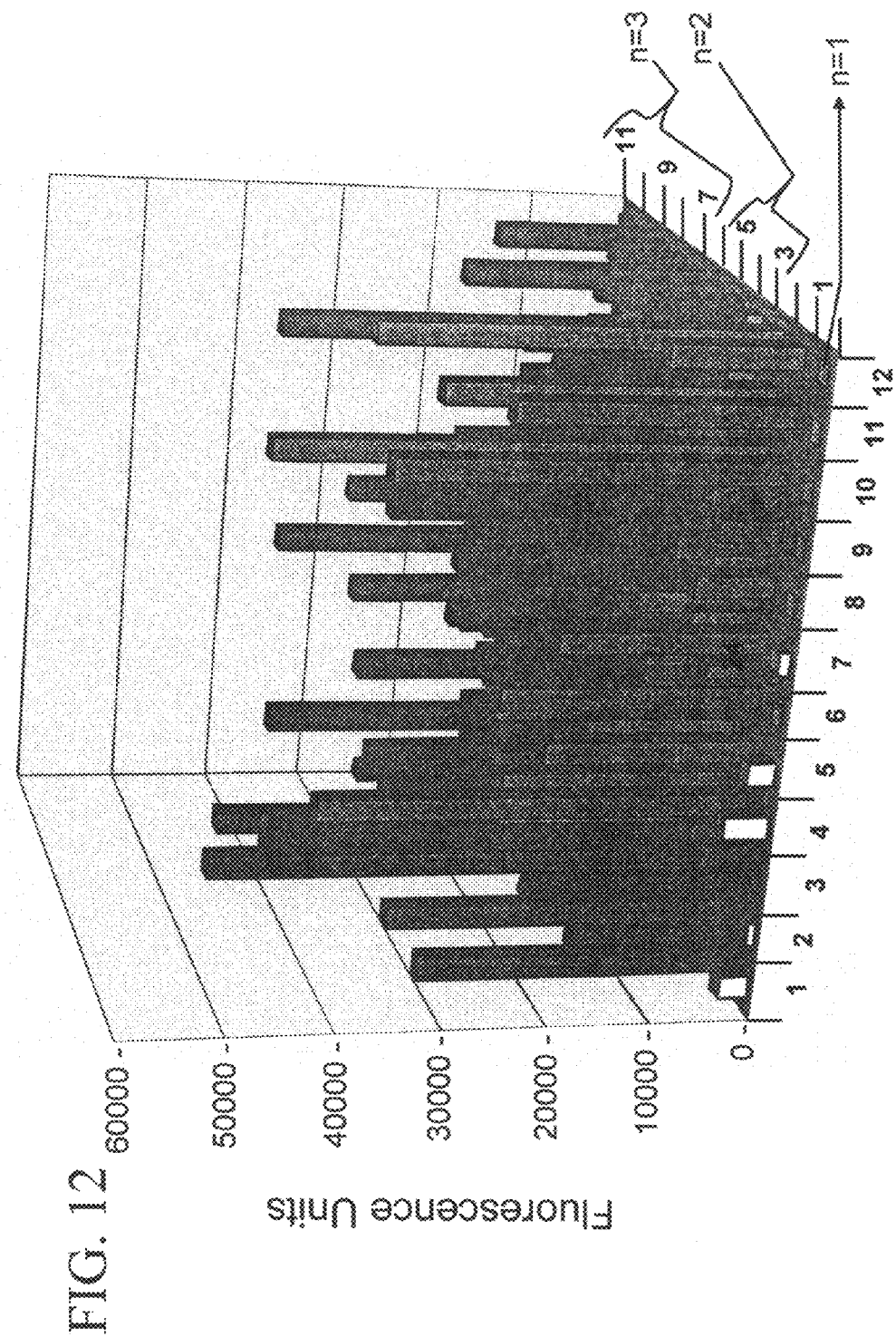
FIG. 12 schematically illustrates a three dimensional plot of data obtained for candidate artificial receptors contacted with and/or binding a fluorescent derivative of bovine serum albumin.
Figure 13:
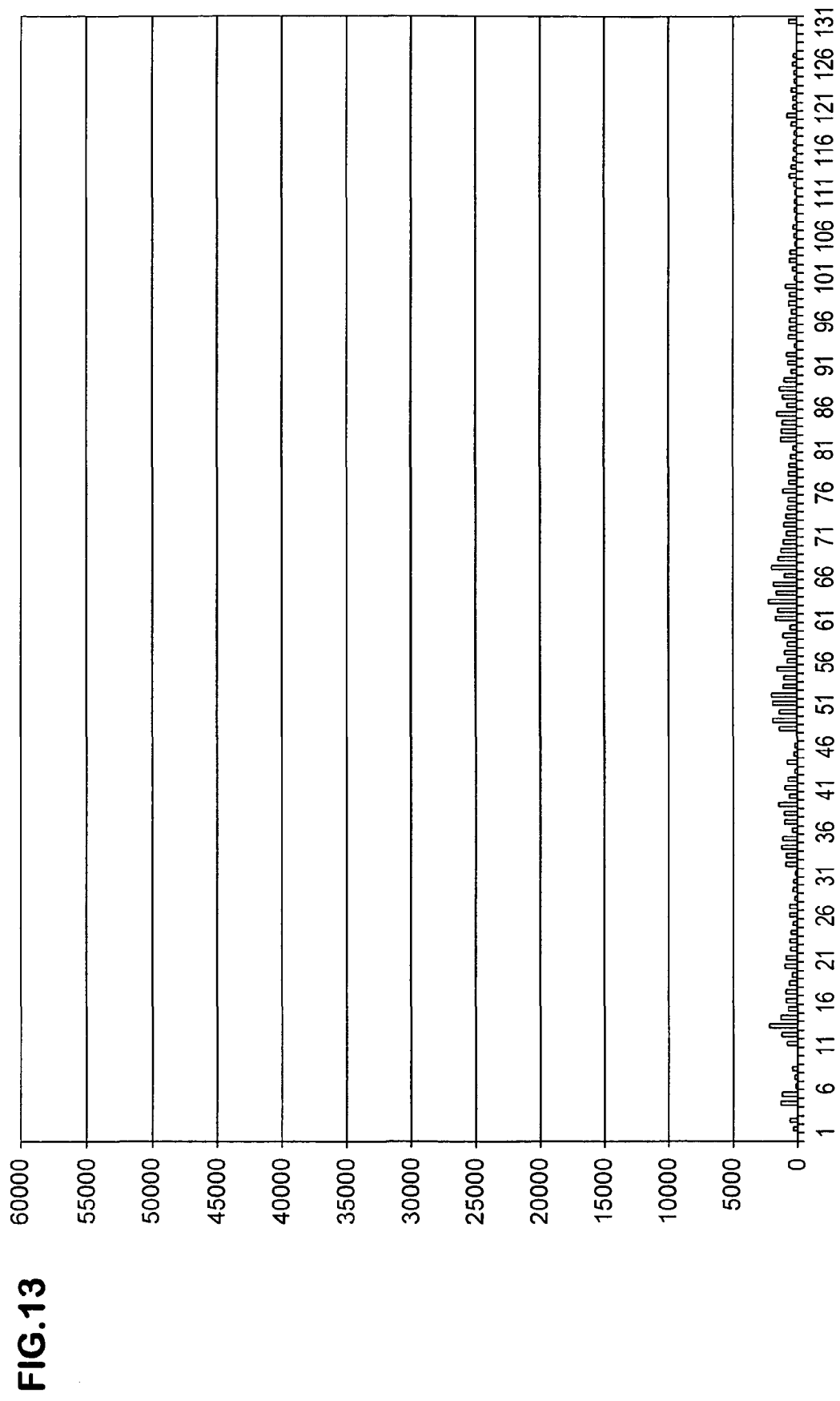
FIG. 13 schematically illustrates a two dimensional plot of data obtained for candidate artificial receptors contacted with and/or binding an acetylated horseradish peroxidase.
Figure 14:
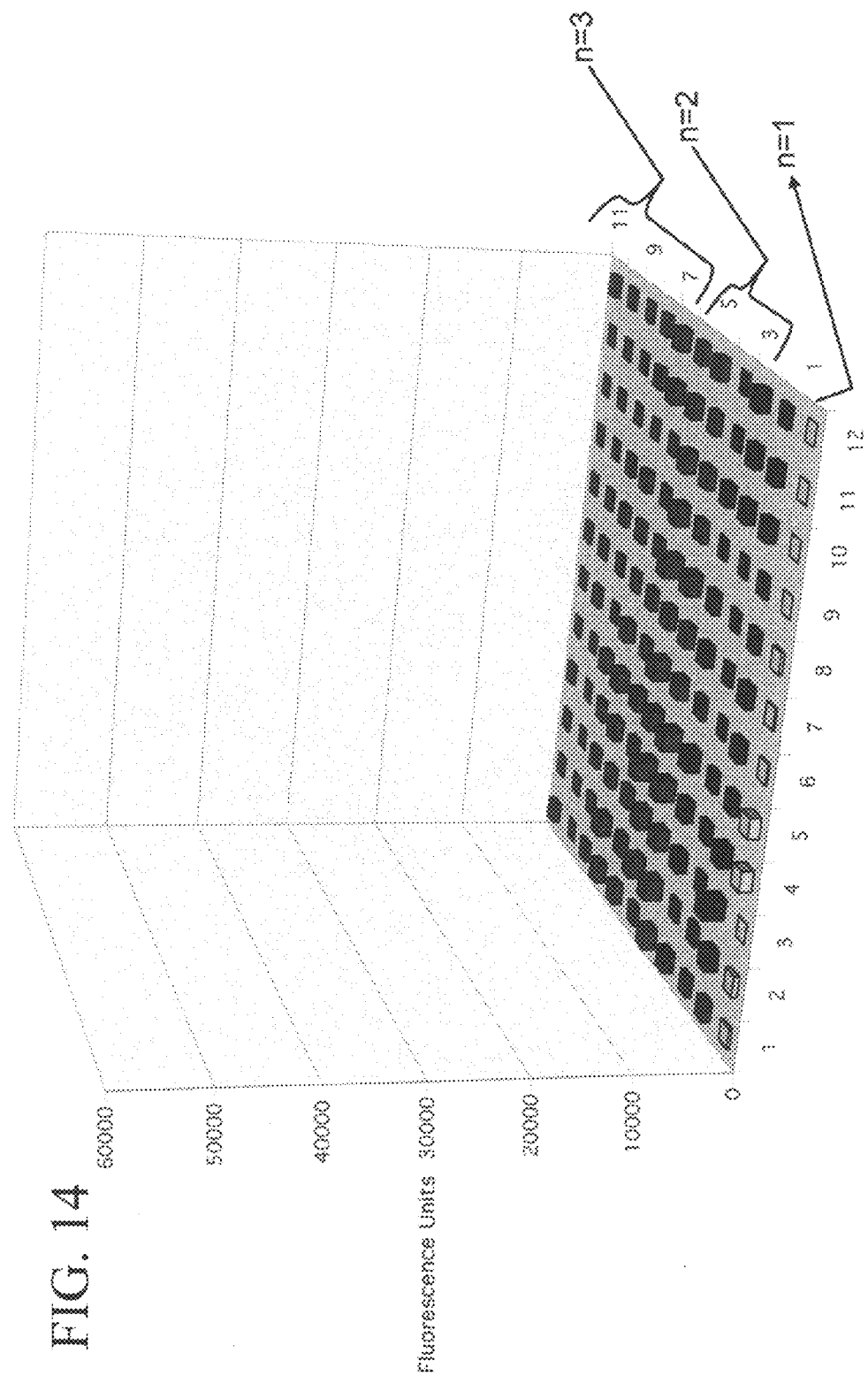
FIG. 14 schematically illustrates a three dimensional plot of data obtained for candidate artificial receptors contacted with and/or binding an acetylated horseradish peroxidase.
Figure 15:
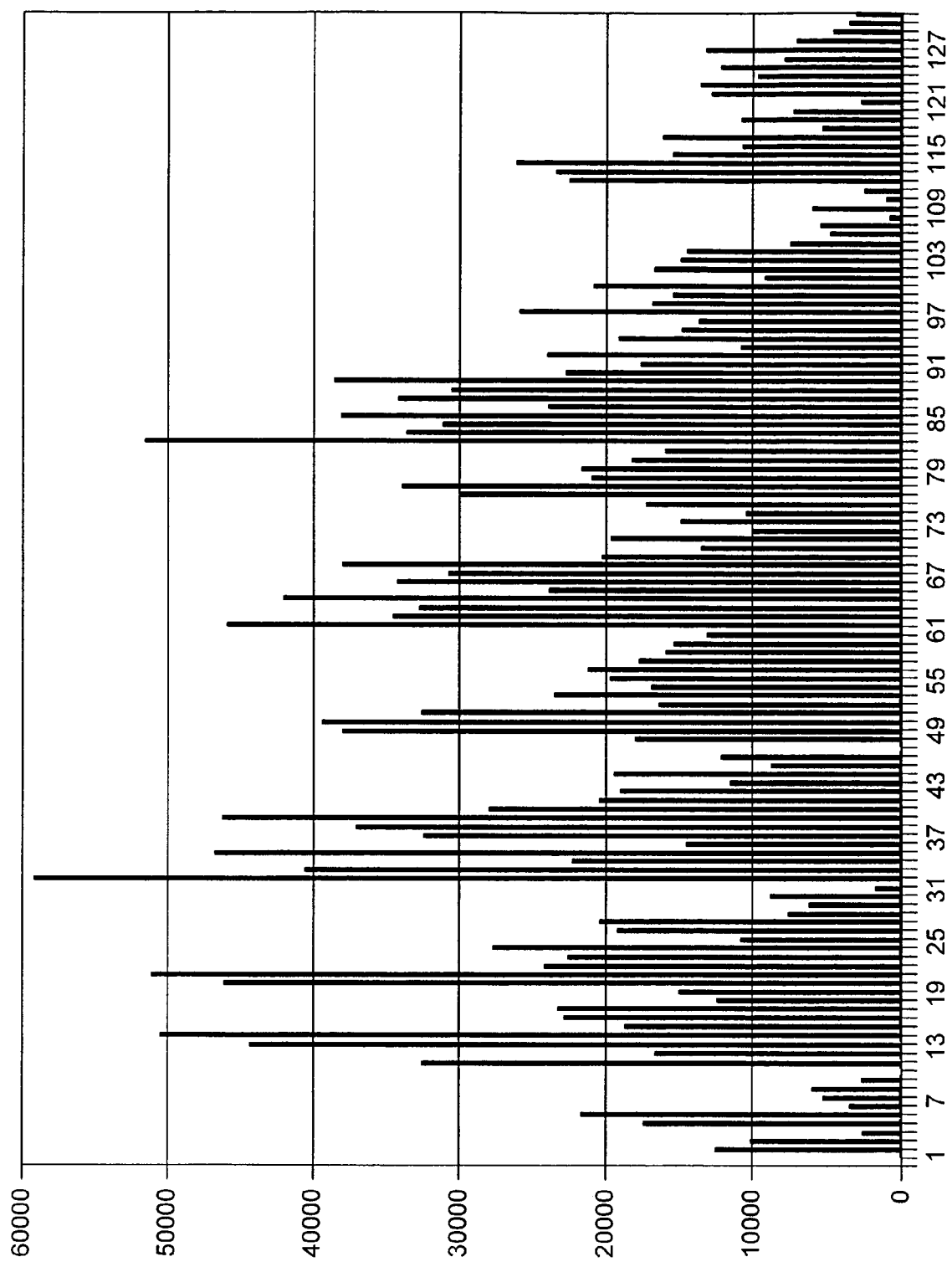
FIG. 15 schematically illustrates a two dimensional plot of data obtained for candidate artificial receptors contacted with and/or binding a TCDD derivative of horseradish peroxidase.
Figure 16:
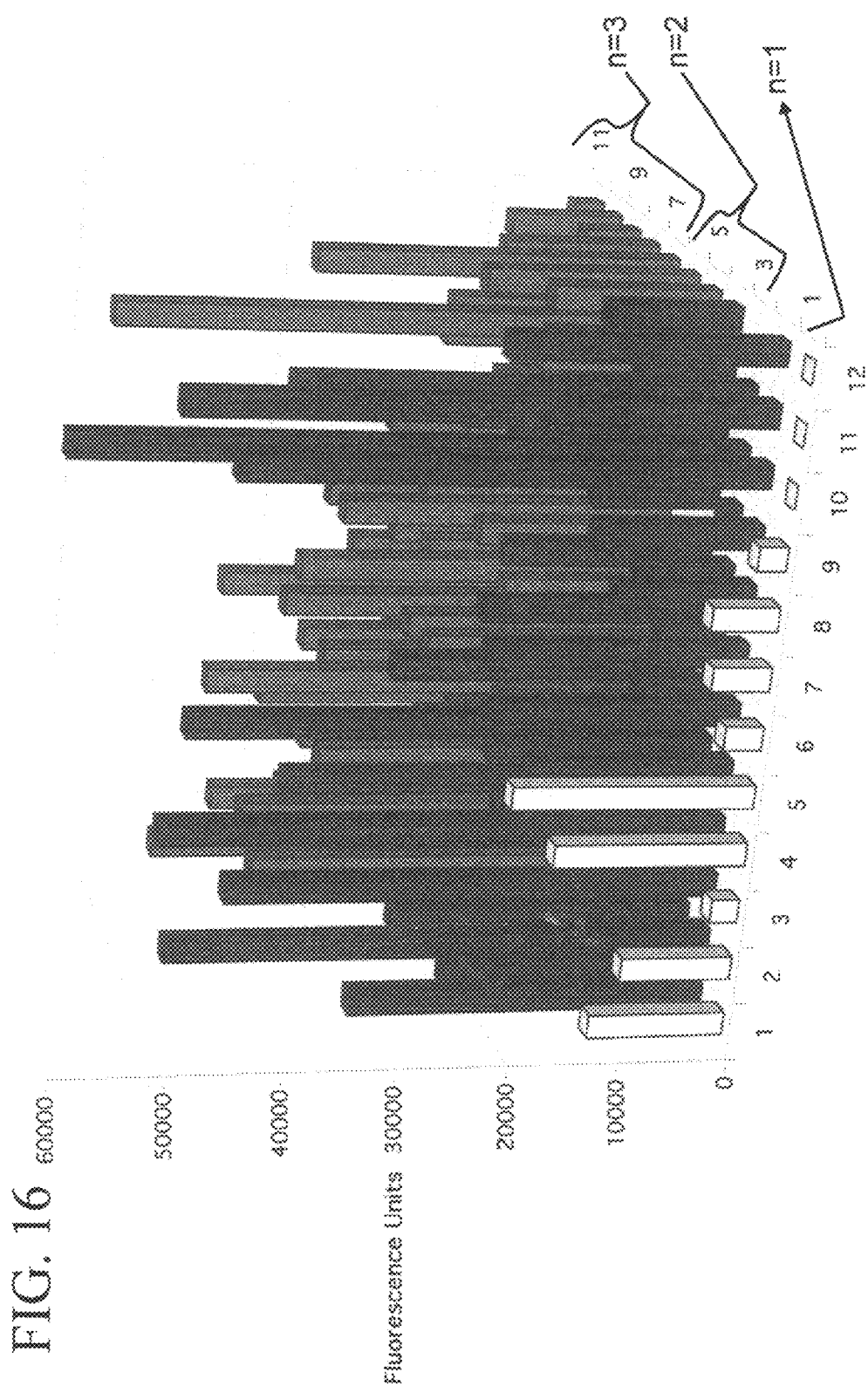
FIG. 16 schematically illustrates a three dimensional plot of data obtained for candidate artificial receptors contacted with and/or binding a TCDD derivative of horseradish peroxidase.

FIGS. 7 and 8 illustrate binding data for r-phycoerythrin (intrinsic fluorescence). FIGS. 9 and 10 illustrate binding data for ovalbumin (commercially available with fluorescence label). FIGS. 11 and 12 illustrate binding data for bovine serum albumin (labeled with rhodamine). FIGS. 13 and 14 illustrate binding data for HRP-NH-Ac (fluorescent tyramide read-out). FIGS. 15 and 16 illustrate binding data for HRP-NH-TCDD (fluorescent tyramide read-out).

These results demonstrate not only the application of the CARA microarray to candidate artificial receptor evaluation but also a few of the many read-out methods (e.g. intrinsic fluorescence, fluorescently labeled, in situ fluorescence labeling) which can be utilized for high throughput candidate receptor evaluation.

The evaluation of candidate receptors benefits from reproducibility. The following results demonstrate that the present microarrays provided reproducible ligand binding.

Figure 17:
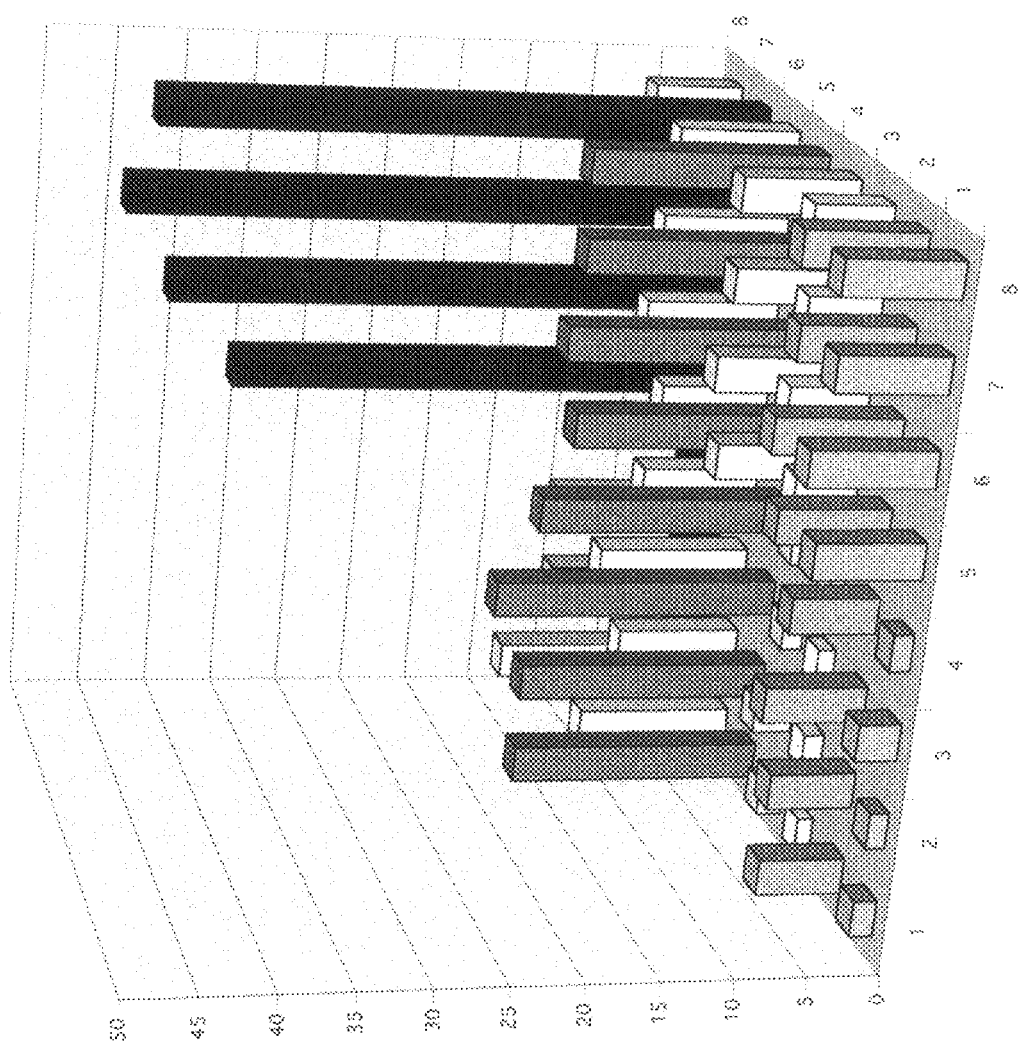
FIG. 17 schematically illustrates a subset of the data illustrated in FIG. 5.

The microarrays were printed with each combination of building blocks spotted in quadruplicate. Visual inspection of a direct plot (FIG. 17) of the raw fluorescence data (from the run illustrated in FIG. 6) for one block of binding data obtained for r-phycoerythrin demonstrates that the candidate receptor environment "spots" showed reproducible binding to the test ligand. Further analysis of the r-phycoerythrin data (FIG. 6) led to only 9 out of 768 spots (1.2%) being deleted as outliers. Analysis of the r-phycoerythrin quadruplicate data for the entire array gives a mean standard deviation for each experimental quadruplicate set of 938 fluorescence units, with a mean coefficient of variation of 19.8%.

Although these values are acceptable, a more realistic comparison employed the standard deviation and coefficient of variation of the more strongly bound, more fluorescent receptors. The overall mean standard deviation unrealistically inflates the coefficient of variation for the weakly bound, less fluorescent receptors. The coefficient of variation for the 19 receptors with greater than 10,000 Fluorescent Units of bound target is 11.1%, which is well within the range required to produce meaningful binding data.

One goal of the CARA approach is the facile preparation of a significant number of candidate receptors through combinations of structurally simple building blocks. The following results establish that both the individual building blocks and combinations of building blocks have a significant, positive effect on test ligand binding.

The binding data illustrated in FIGS. 15-16 demonstrate that heterogeneous combinations of building blocks (n=2, n=3) are dramatically superior candidate receptors made from a single building block (n=1). For example, FIG. 8 illustrates both the diversity of binding observed for n=2, n=3 candidate receptors with fluorescent units ranging from 0 to ca. 40,000. These data also illustrate and the ca. 10-fold improvement in binding affinity obtained upon going from the homogeneous (n=1) to heterogeneous (n=2, n=3) receptor environments.

Figure 18:
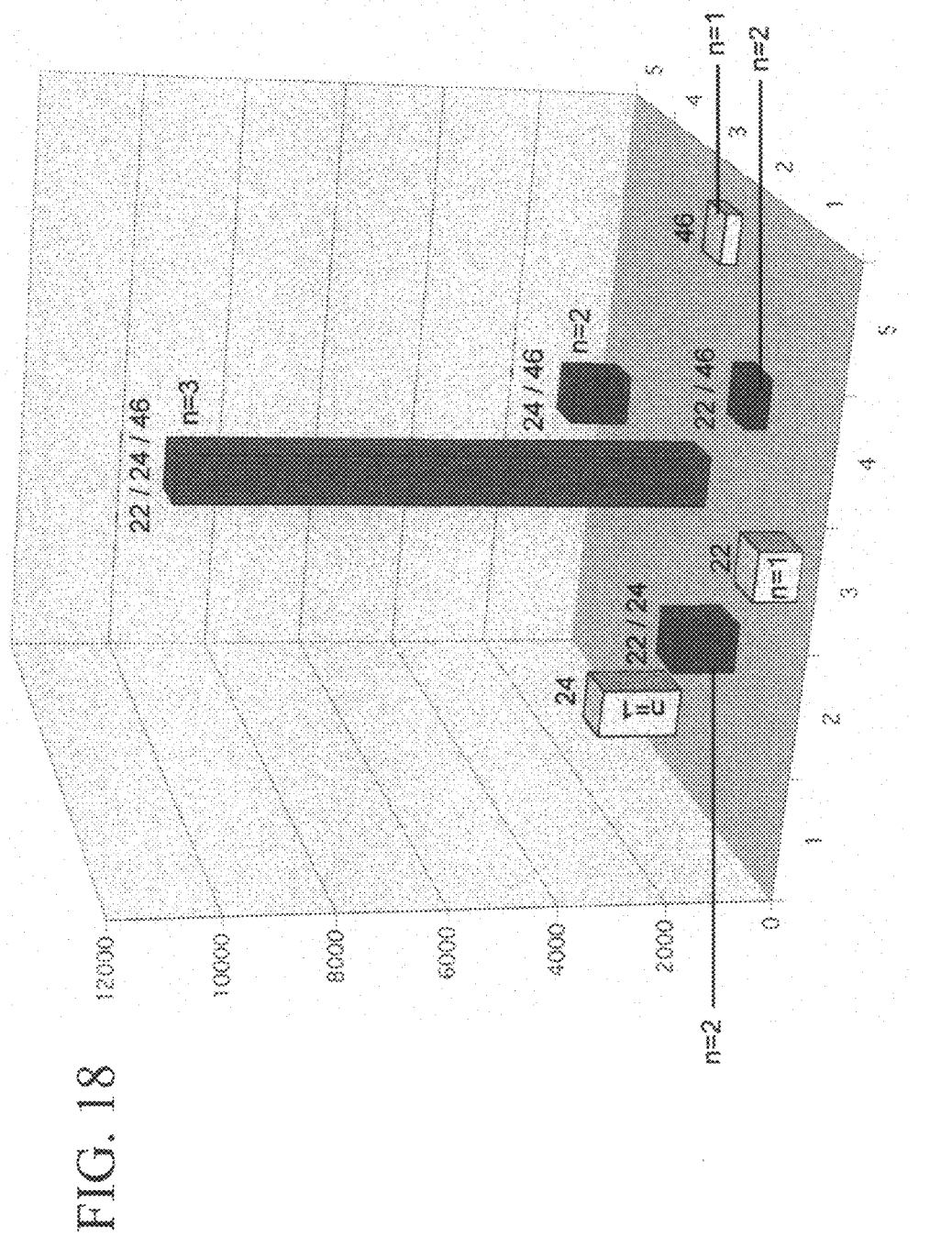
FIG. 18 schematically illustrates a subset of the data illustrated in FIG. 5.
Figure 19:
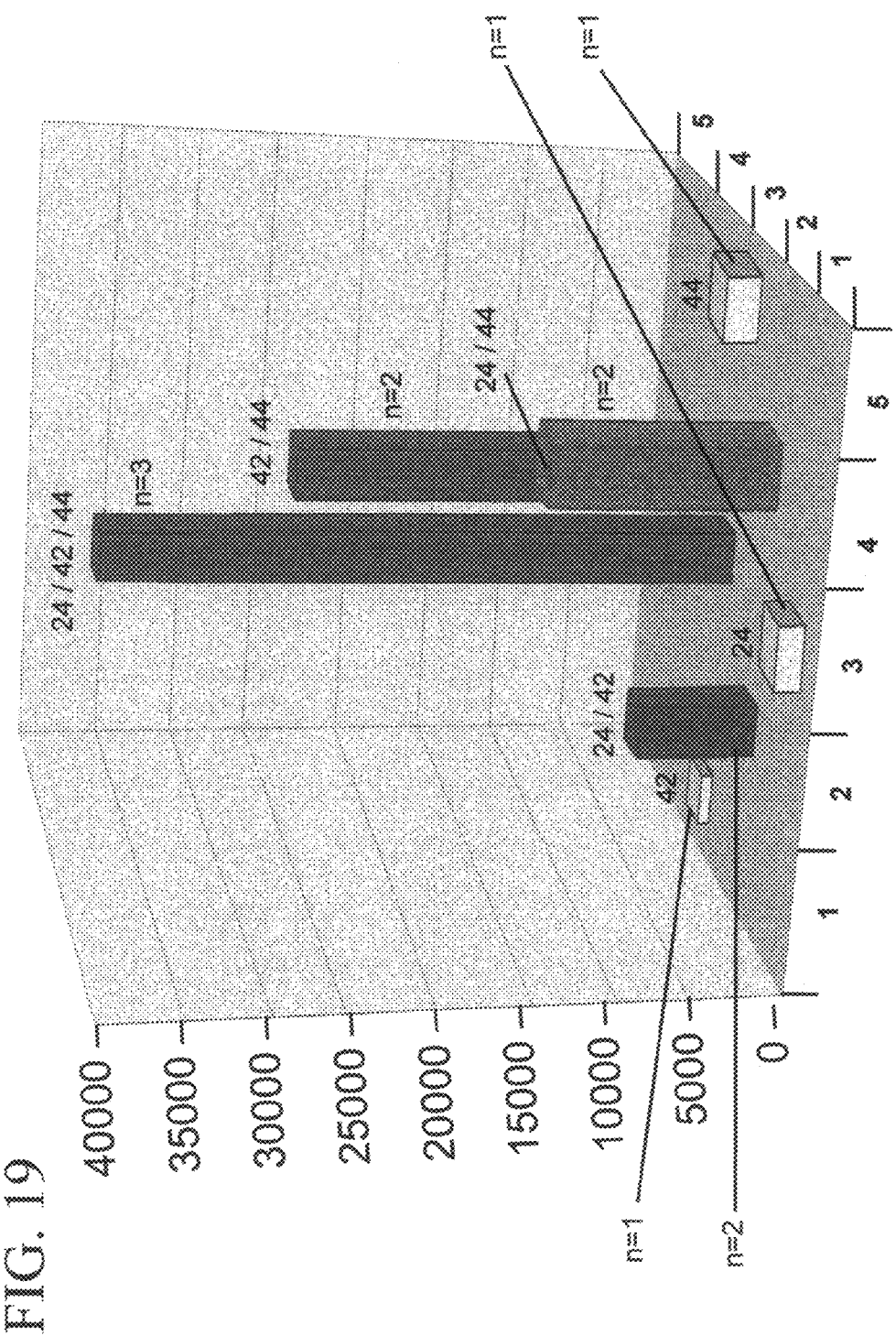
FIG. 19 schematically illustrates a subset of the data illustrated in FIG. 5.

The effect of heterogeneous building blocks is most easily observed by comparing selected n=3 receptor environments candidate receptors including 1 or 2 of those building blocks (their n=2 and n=1 subsets). FIGS. 18 and 19 illustrate this comparison for two different n=3 receptor environments using the r-phycoerythrin data. In these examples, it is clear that progression from the homogeneous system (n=1) to the heterogeneous systems (n=2, n=3) produces significantly enhanced binding.

Figure 20:
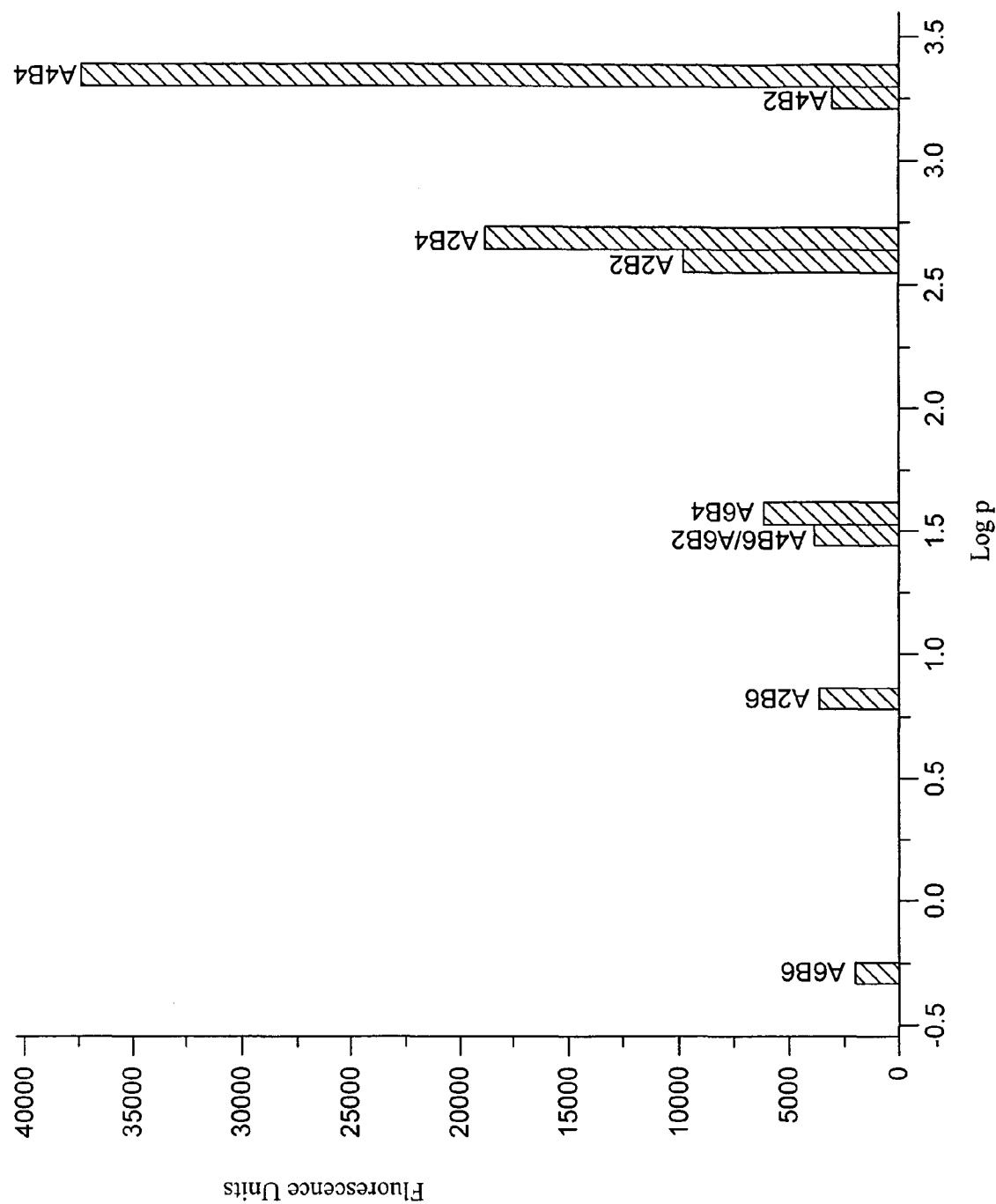
FIG. 20 schematically illustrates a correlation of binding data for phycoerythrin against logP for the building blocks making up the artificial receptor.
Figure 21:
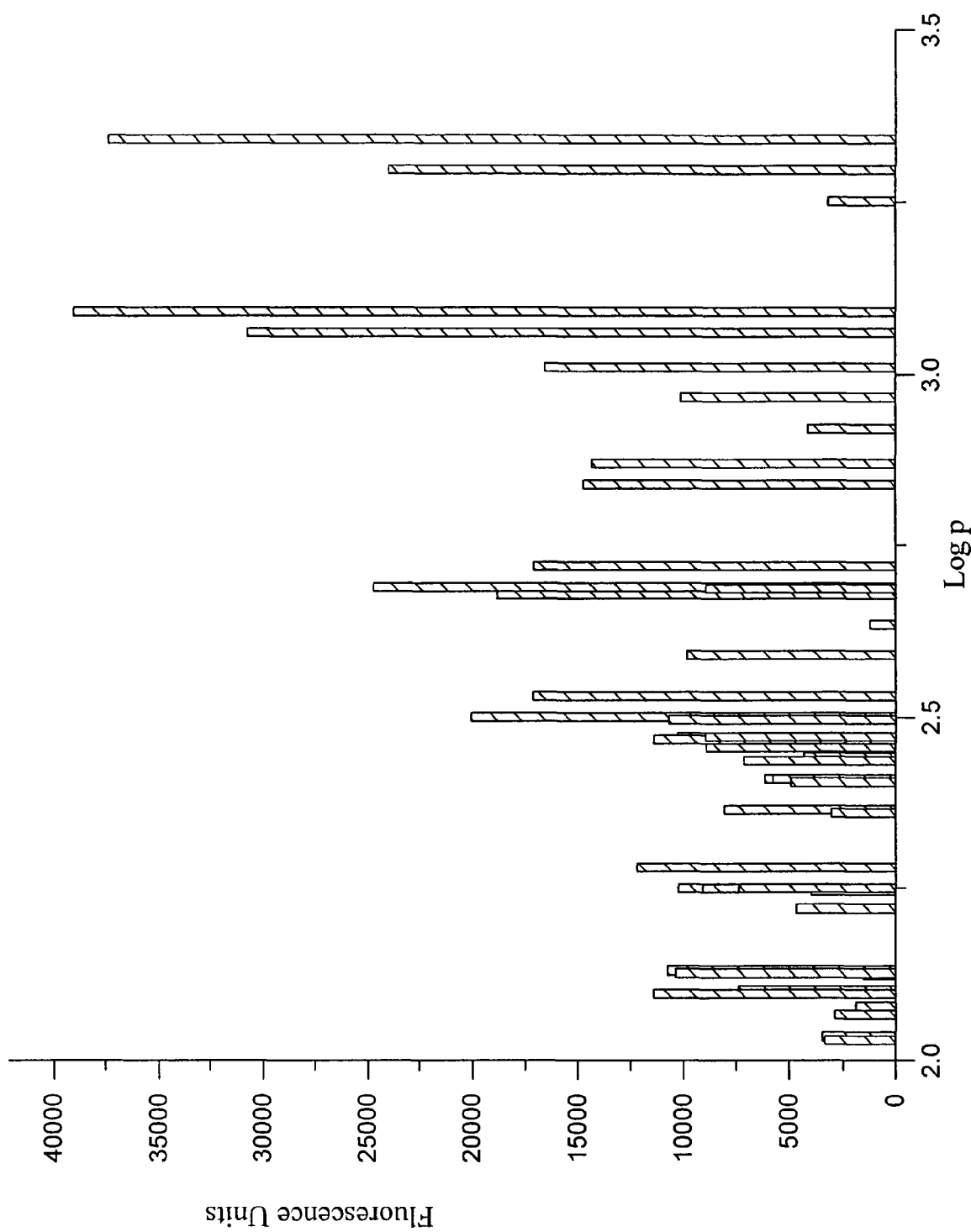
FIG. 21 schematically illustrates a correlation of binding data for phycoerythrin against logP for the building blocks making up the artificial receptor.

Although van der Waals interactions are an important part of molecular recognition, it is important to establish that the observed binding is not a simple case of hydrophobic/hydrophilic partitioning. That is, that the observed binding was the result of specific interactions between the individual building blocks and the target The simplest way to evaluate the effects of hydrophobicity and hydrophilicity is to compare building block logP value with observed binding. LogP is a known and accepted measure of lipophilicity, which can be measured or calculated by known methods for each of the building blocks. FIGS. 20 and 21 establish that the observed target binding, as measured by fluorescence units, is not directly proportional to building block logP. The plots in FIGS. 20 and 21 illustrate a non-linear relationship between binding (fluorescence units) and building block logP.

One advantage of the present methods and arrays is that the ability to screen large numbers of candidate receptor environments will lead to a combination of useful target affinities and to significant target binding diversity. High target affinity is useful for specific target binding, isolation, etc. while binding diversity can provide multiplexed target detection systems. This example employed a relatively small number of building blocks to produce ca. 120 binding environments. The following analysis of the present data clearly demonstrates that even a relatively small number of binding environments can produce diverse and useful artificial receptors.

The target binding experiments performed for this study used protein concentrations including 0.1 to 10 μg/ml. Considering the BSA data as representative, it is clear that some of the receptor environments readily bound 1.0 μg/ml BSA concentrations near the saturation values for fluorescence units (see, e.g., FIG. 12). Based on these data and the formula weight of 68,000 for BSA, several of the receptor environments readily bind BSA at ca. 15 picomole/ml or 15 nanomolar concentrations. Additional experiments using lower concentrations of protein (data not shown) indicate that, even with a small selection of candidate receptor environments, femptomole/ml or picomolar detection limits have been attained.

Figure 22:
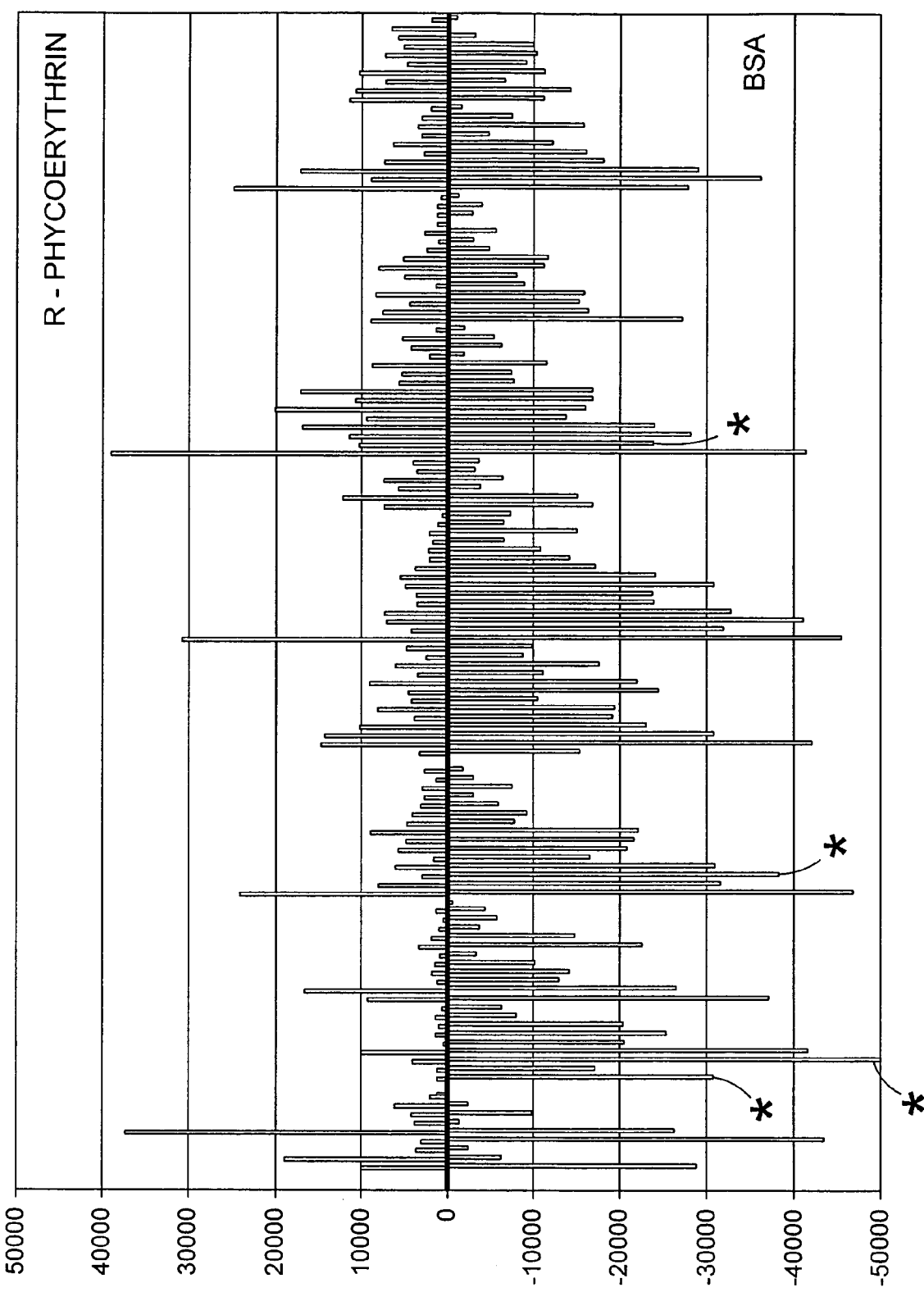
FIG. 22 schematically illustrates a two dimensional plot comparing data obtained for candidate artificial receptors contacted with and/or binding phycoerythrin to data obtained for candidate artificial receptors contacted with and/or binding a fluorescent derivative of bovine serum albumin.

One goal of artificial receptor development is the specific recognition of a particular target. FIG. 22 compares the observed binding for r-phycoerythrin and BSA. Comparison of the overall binding pattern indicates some general similarities. However, comparison of specific features of binding for each receptor environment demonstrates that the two targets have distinctive recognition features as indicated by the (*) in FIG. 22.

Figure 23:
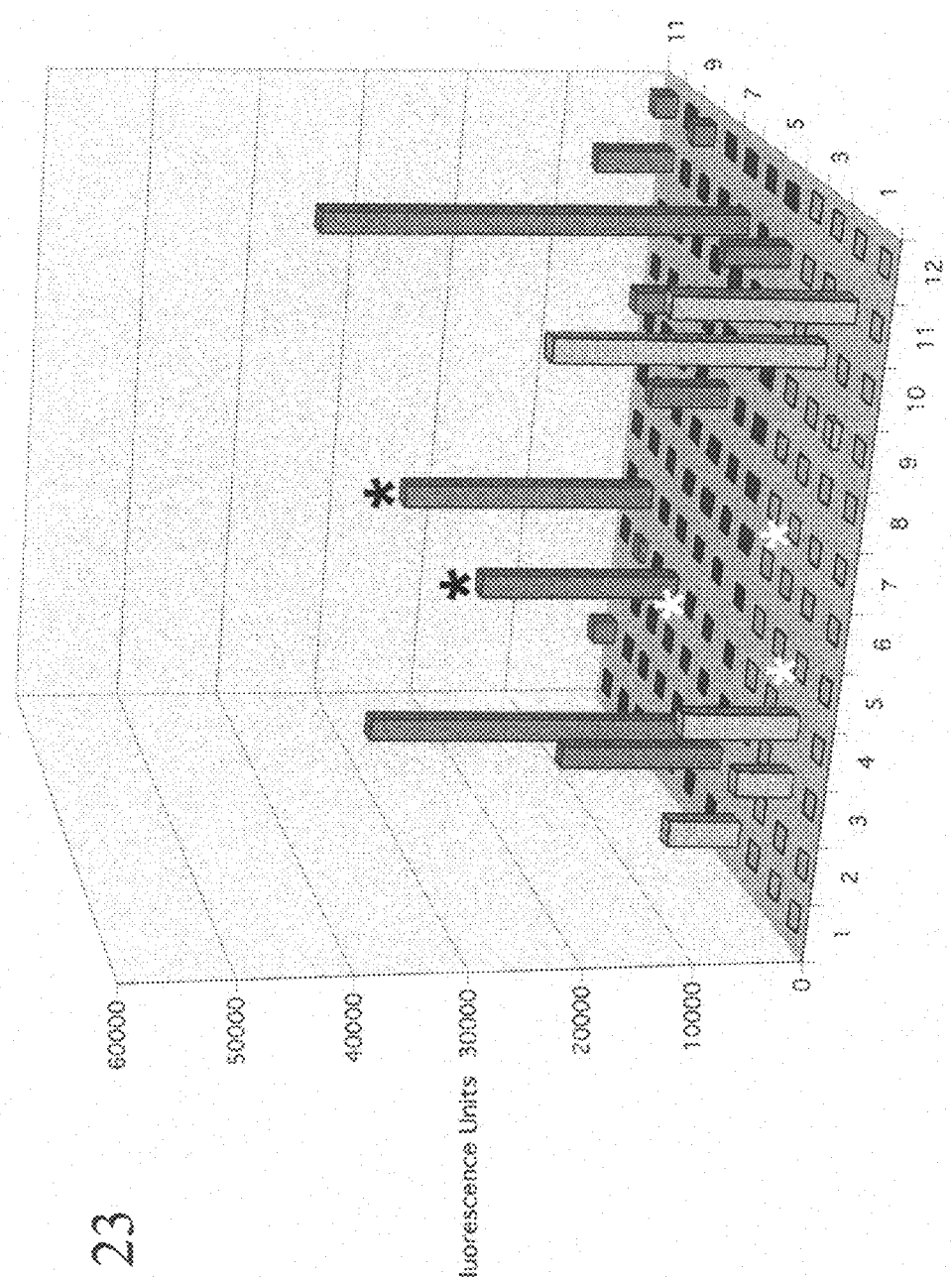
FIGS. 23, 24, and 25 schematically illustrate subsets of data from FIGS. 5, 9, and 7, respectively, and demonstrate that the array of artificial receptors according to the present invention yields receptors distinguished between three analytes, phycoerythrin, bovine serum albumin, and ovalbumin.
Figure 24:
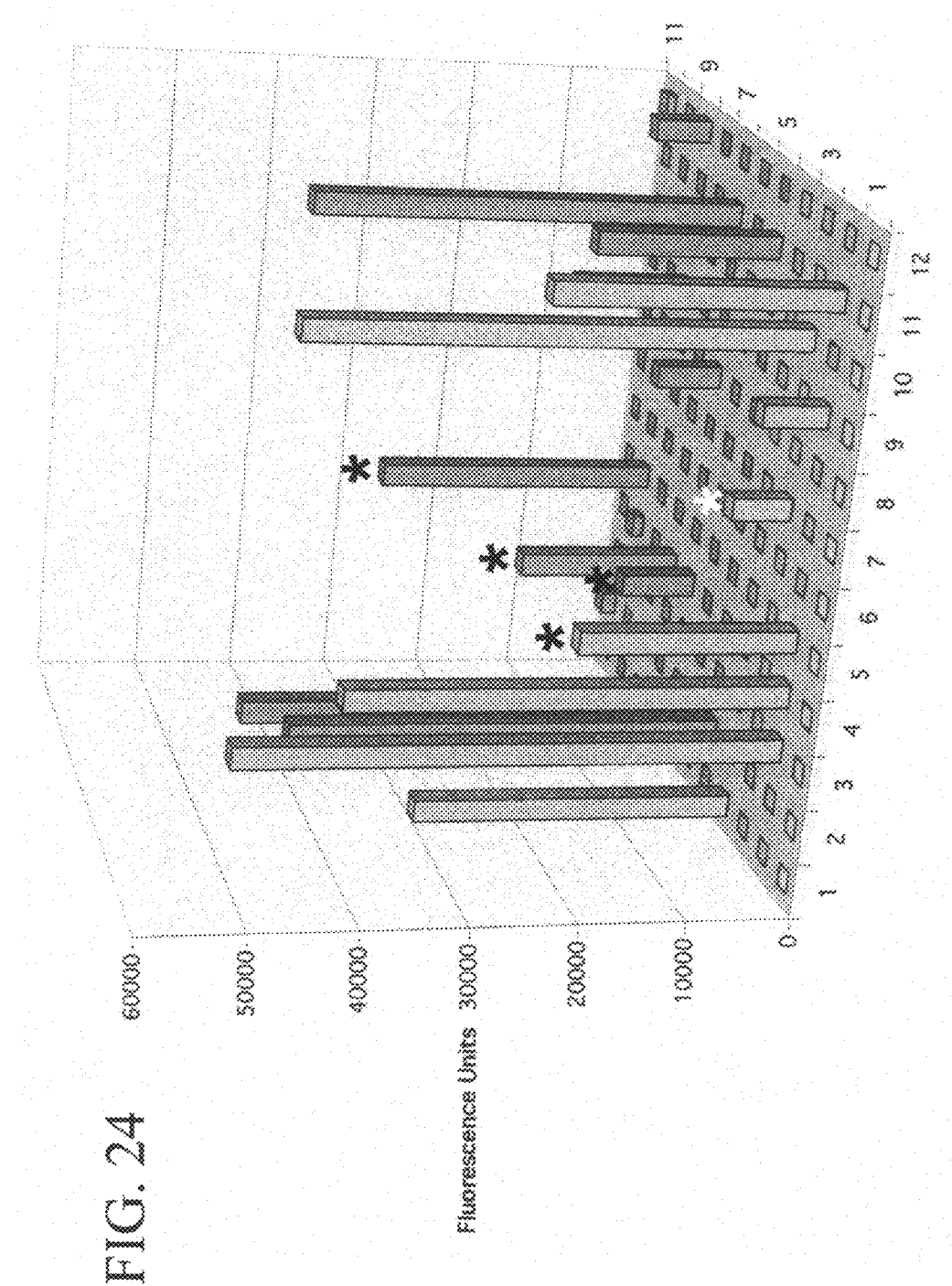
Figure 25:
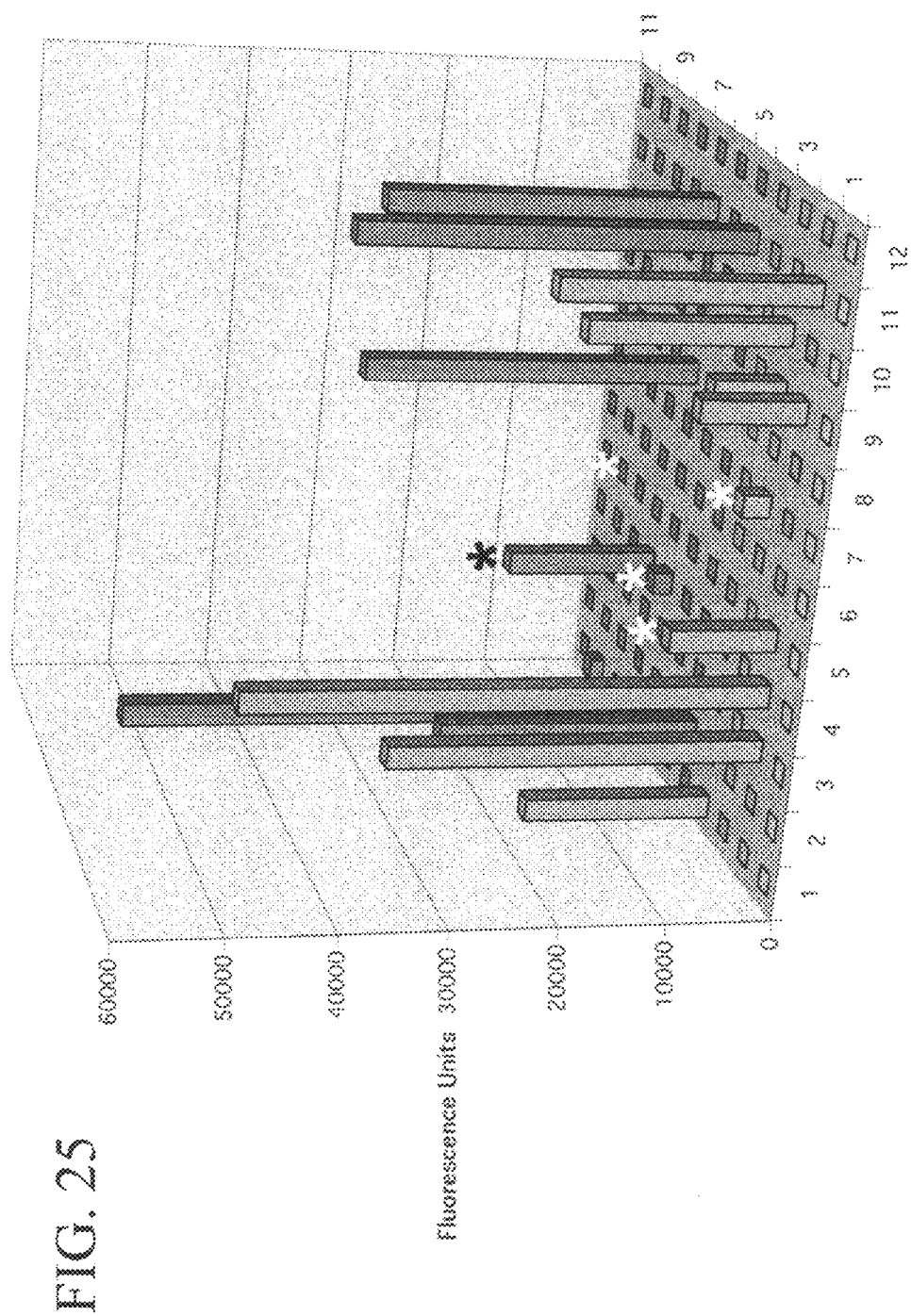

One goal of artificial receptor development is to develop receptors which can be used for the multiplexed detection of specific targets. Comparison of the r-phycoerythrin, BSA and ovalbumin data from this study (FIGS. 8, 10, and 12) were used to select representative artificial receptors for each target. FIGS. 23, 24, and 25 employ data obtained in the present example to illustrate identification of each of these three targets by their distinctive binding patterns.

Conclusions

The optimum receptor for a particular target requires molecular recognition which is greater than the expected sum of the individual hydrophilic, hydrophobic, ionic, etc. interactions. Thus, the identification of an optimum (specific, sensitive) artificial receptor from the limited pool of candidate receptors explored in this prototype study, was not expected and not likely. Rather, the goal was to demonstrate that all of the key components of the CARA: Combinatorial Artificial Receptor Array concept could be assembled to form a functional receptor microarray. This goal has been successfully demonstrated.

This study has conclusively established that CARA microarrays can be readily prepared and that target binding to the candidate receptor environments can be used to identify artificial receptors and test ligands. In addition, these results demonstrate that there is significant binding enhancement for the building block heterogeneous (n=2, n=3, or n=4) candidate receptors when compared to their homogeneous (n=1) counterparts. When combined with the binding pattern recognition results and the demonstrated importance of both the heterogeneous receptor elements and heterogeneous building blocks, these results clearly demonstrate the significance of the CARA Candidate Artificial Receptor->Lead Artificial Receptor->Working Artificial Receptor strategy.

Example 3

Preparation and Evaluation of Microarrays of Candidate Artificial Receptors Including Reversibly Immobilized Building Blocks Microarrays of candidate artificial receptors including building blocks immobilized through van der Waals interactions were made and evaluated for binding of a protein ligand. The evaluation was conducted at several temperatures, above and below a phase transition temperature for the lawn (vide infra).

Materials and Methods

Building blocks 2-2, 2-4, 2-6, 4-2, 4-4, 4-6, 6-2, 6-4, 6-6 where prepared as described in Example 1. The C12 amide was prepared using the previously described carbodiimide activation of the carboxyl followed by addition of dodecylamine. This produced a building block with a 12 carbon alkyl chain linker for reversible immobilization in the C18 lawn.

Amino lawn microarray plates (Telechem) were modified to produce the C18 lawn by reaction of stearoyl chloride (Aldrich Chemical Co.) in A) dimethylformamide/PEG 400 solution (90:10, v/v, PEG 400 is polyethylene glycol average MW 400 (Aldrich Chemical Co.) or B) methylene chloride/TEA solution (100 ml methylene chloride, 200 μl triethylamine) using the lawn modification procedures generally described in Example 2.

The C18 lawn plates where printed using the SpotBot standard procedure as described in Example 2. The building blocks were in printing solutions prepared by solution of ca. 10 mg of each building block in 300 μl of methylene chloride and 100 μl methanol. To this stock was added 900 μl of dimethylformamide and 100 μl of PEG 400. The 36 combinations of the 9 building blocks taken two at a time (N9:n2, 36 combinations) where prepared in a 384-well microwell plate which was then used in the SpotBot to print the microarray in quadruplicate. A random selection of the print positions contained only print solution.

The selected microarray was incubated with a 1.0 μg/ml solution of the test ligand, cholera toxin subunit B labeled with the Alexa™ fluorophore (Molecular Probes Inc., Eugene, Oreg.), using the following variables: 1) the microarray was washed with methylene chloride, ethanol and water to create a control plate; and 2) the microarray was incubated at 4° C., 23° C., or 44° C. After incubation, the plate(s) were rinsed with water, dried and scanned (AXON 4100A). Data analysis was as described in Example 2.

Results

Figure 26:
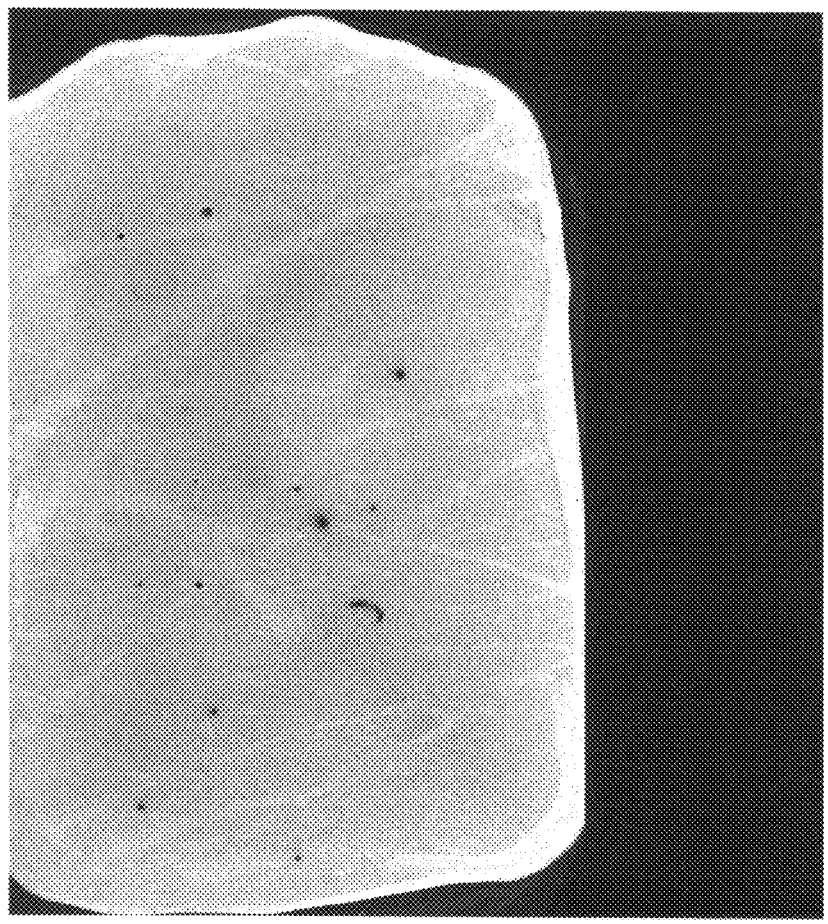
FIG. 26 schematically illustrates a gray scale image of the fluorescence signal from a scan of a control plate which was prepared by washing off the building blocks with organic solvent before incubation with the test ligand.
Figure 27:
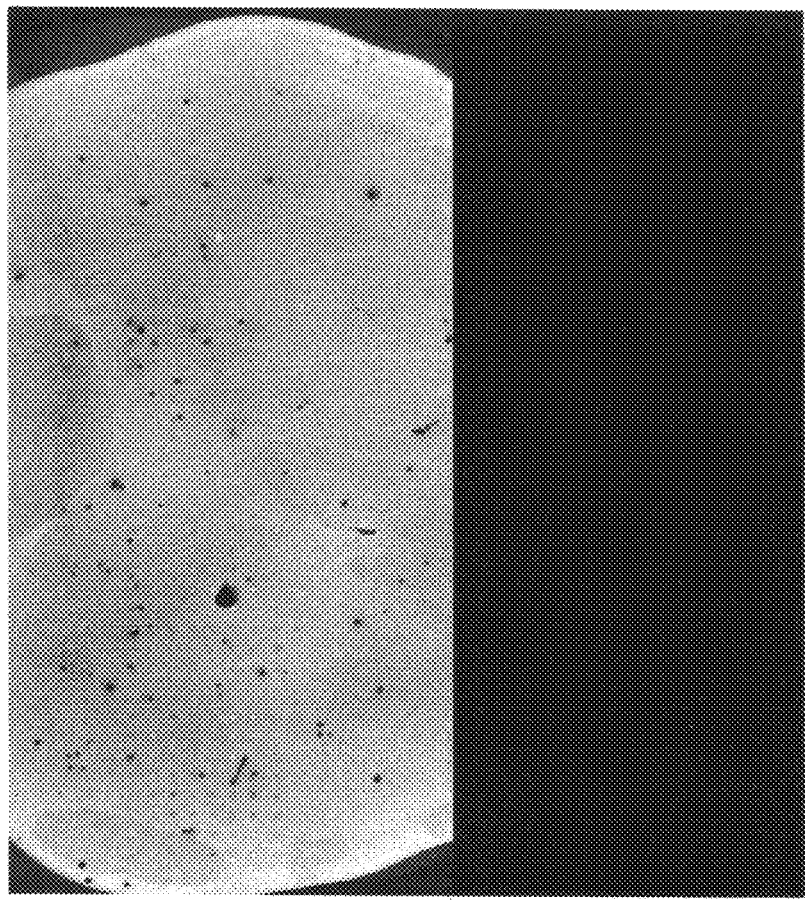
FIG. 27 schematically illustrates a gray scale image of the fluorescence signal from a scan of an experimental plate which was incubated with 1.0 µg/ml Cholera Toxin B at 23° C.
Figure 28:
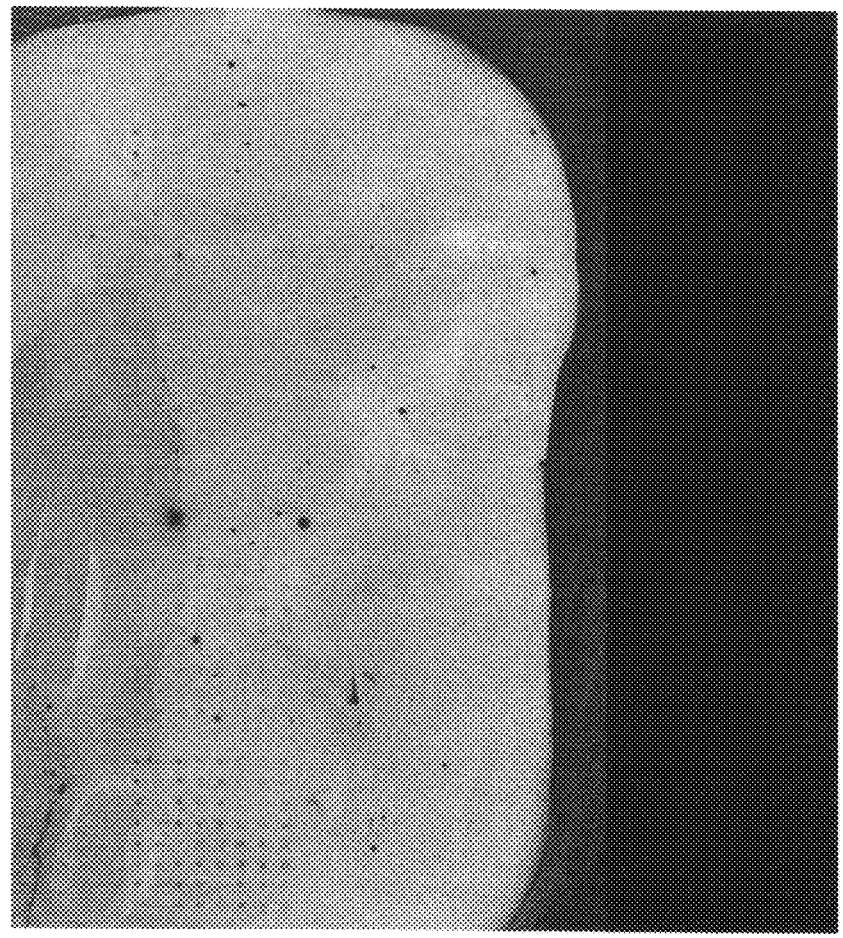
FIG. 28 schematically illustrates a gray scale image of the fluorescence signal from a scan of an experimental plate which was incubated with 1.0 µg/ml Cholera Toxin B at 3° C.
Figure 29:
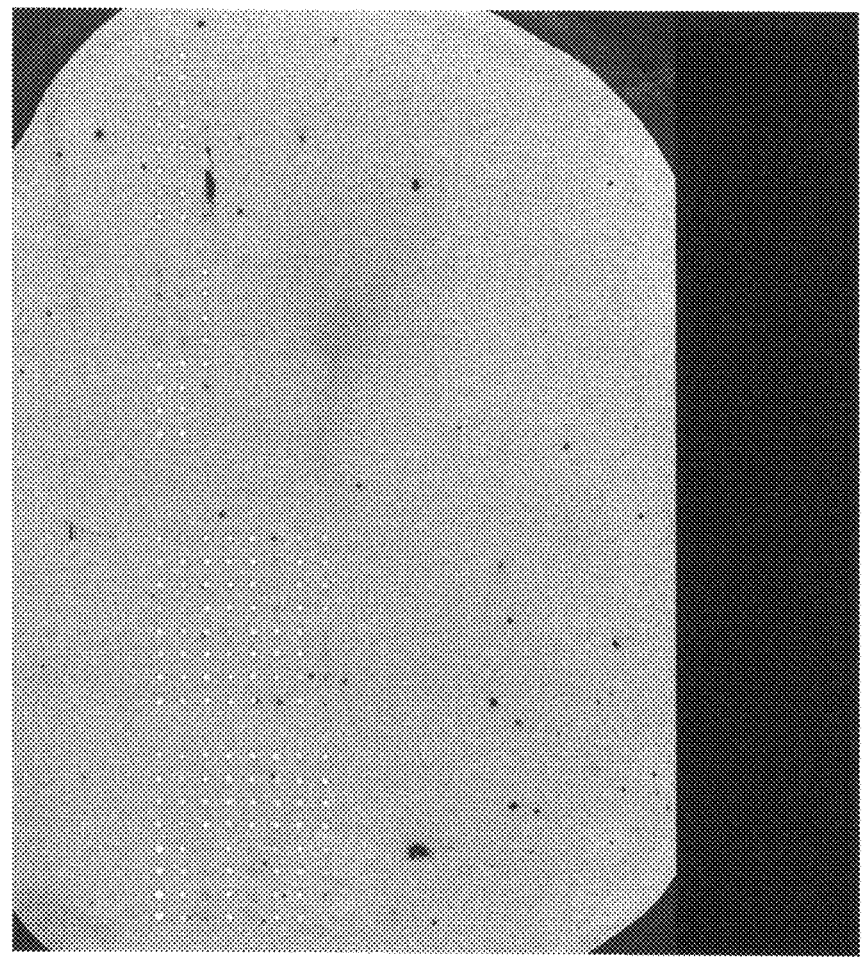
FIG. 29 schematically illustrates a gray scale image of the fluorescence signal from a scan of an experimental plate which was incubated with 1.0 µg/ml Cholera Toxin B at 43° C.
Figure 30:
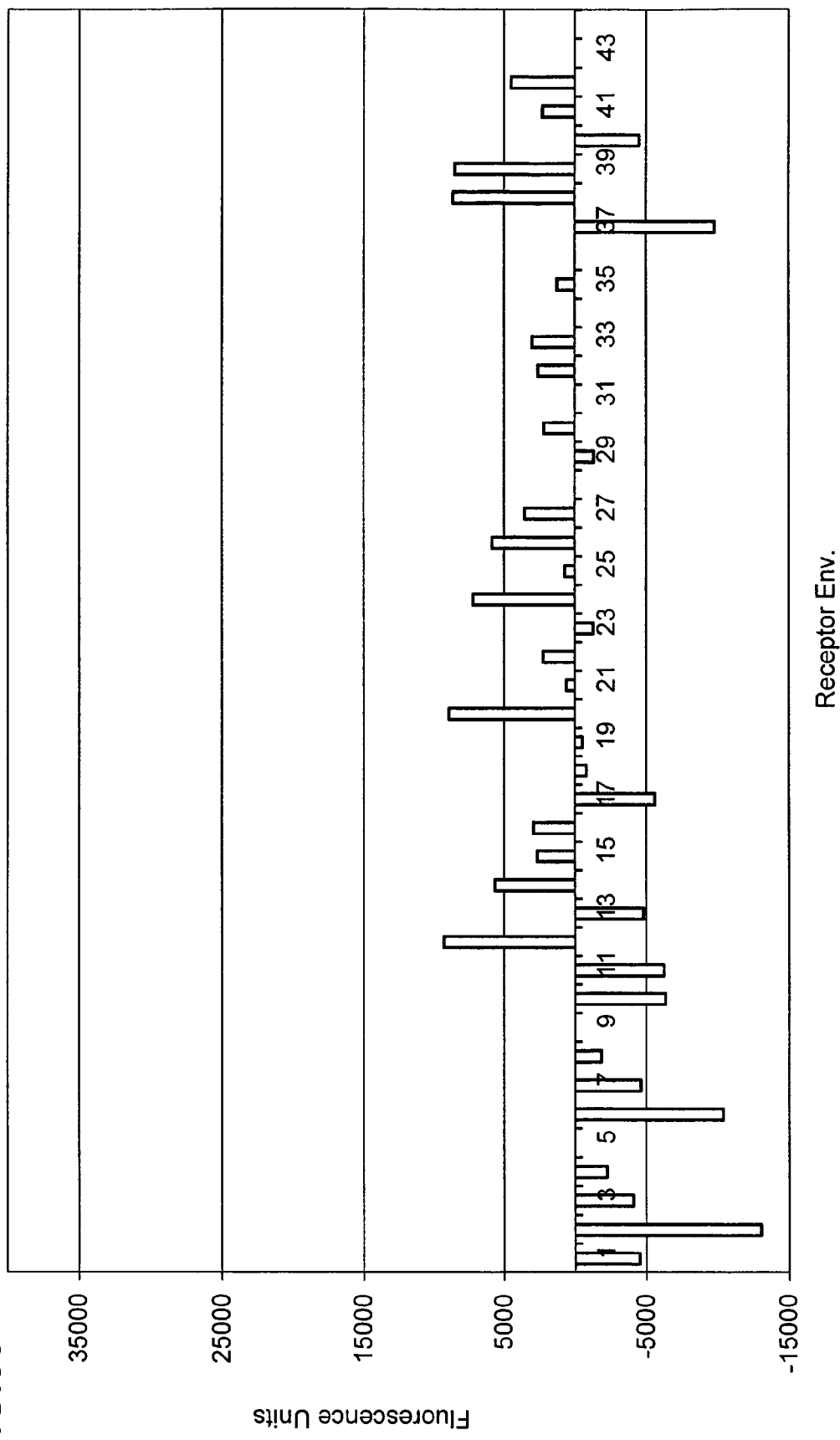
FIGS. 30-32 schematically illustrate plots of the fluorescence signals obtained from the candidate artificial receptors illustrated in FIGS. 24-29.
Figure 31:
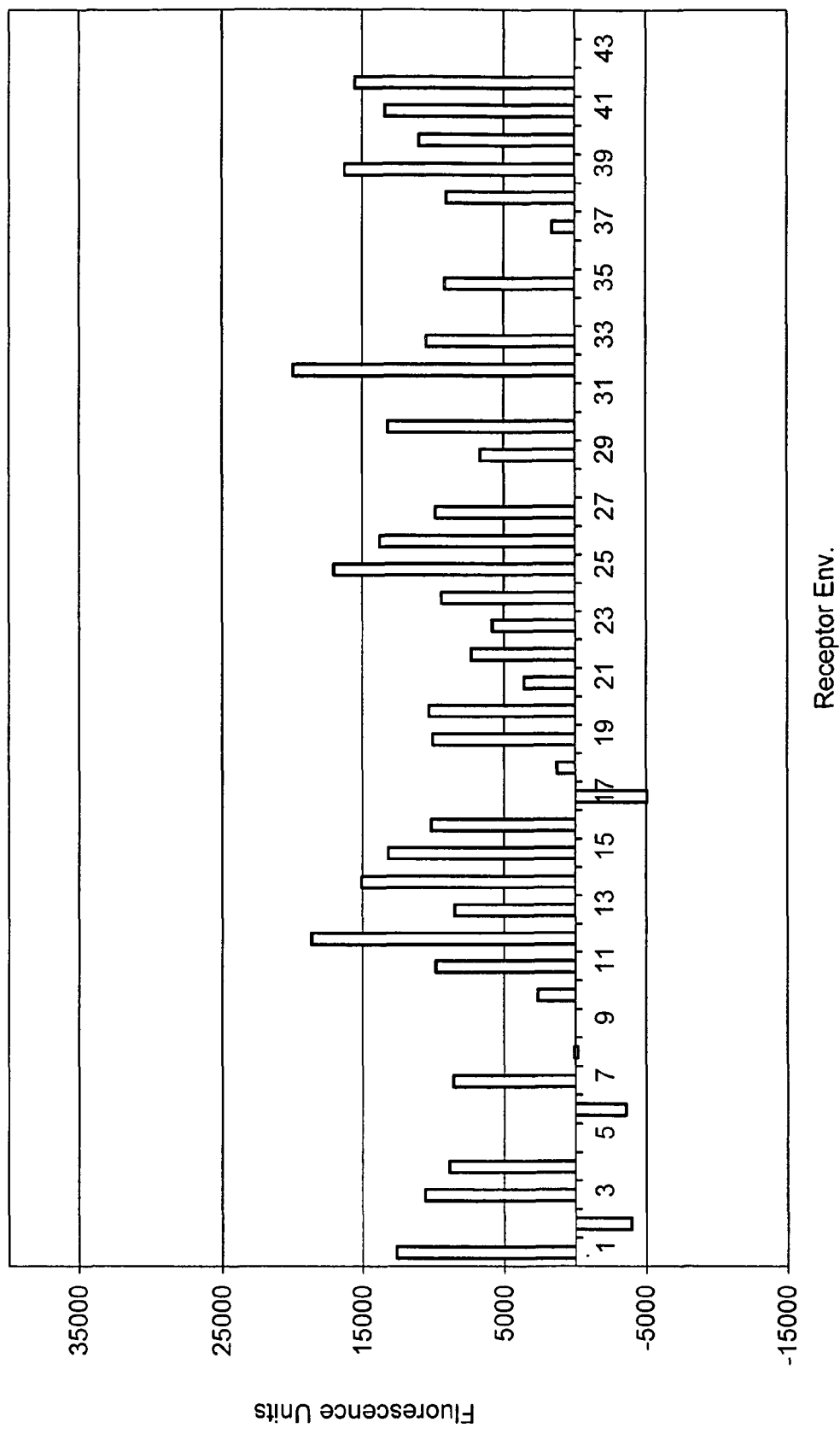
Figure 32:
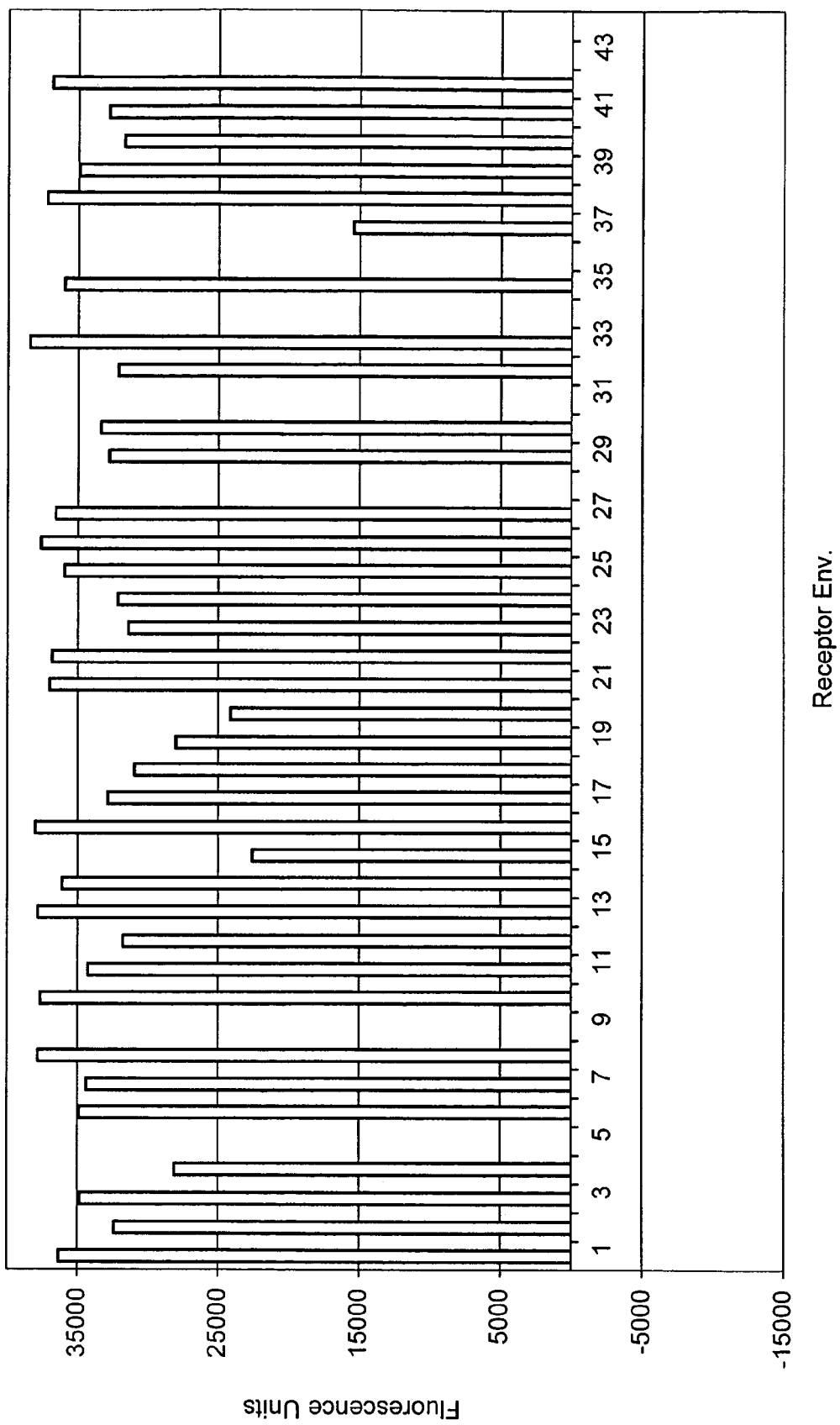

A control array from which the building blocks had been removed by washing with organic solvent did not bind cholera toxin (FIG. 26). FIGS. 27-29 illustrate fluorescence signals from arrays printed identically, but incubated with cholera toxin at 4° C., 23° C., or 44° C., respectively. Spots of fluorescence can be seen in each array, with very pronounced spots produced by incubation at 44° C. The fluorescence values for the spots in each of these three arrays are shown in FIGS. 30-32. Fluorescence signal generally increases with temperature, with many nearly equally large signals observed after incubation at 44° C. Linear increases with temperature can reflect expected improvements in binding with temperature. Nonlinear increases reflect rearrangement of the building blocks on the surface to achieve improved binding, which occurred above the phase transition for the lipid surface (vide infra).

Figure 33:
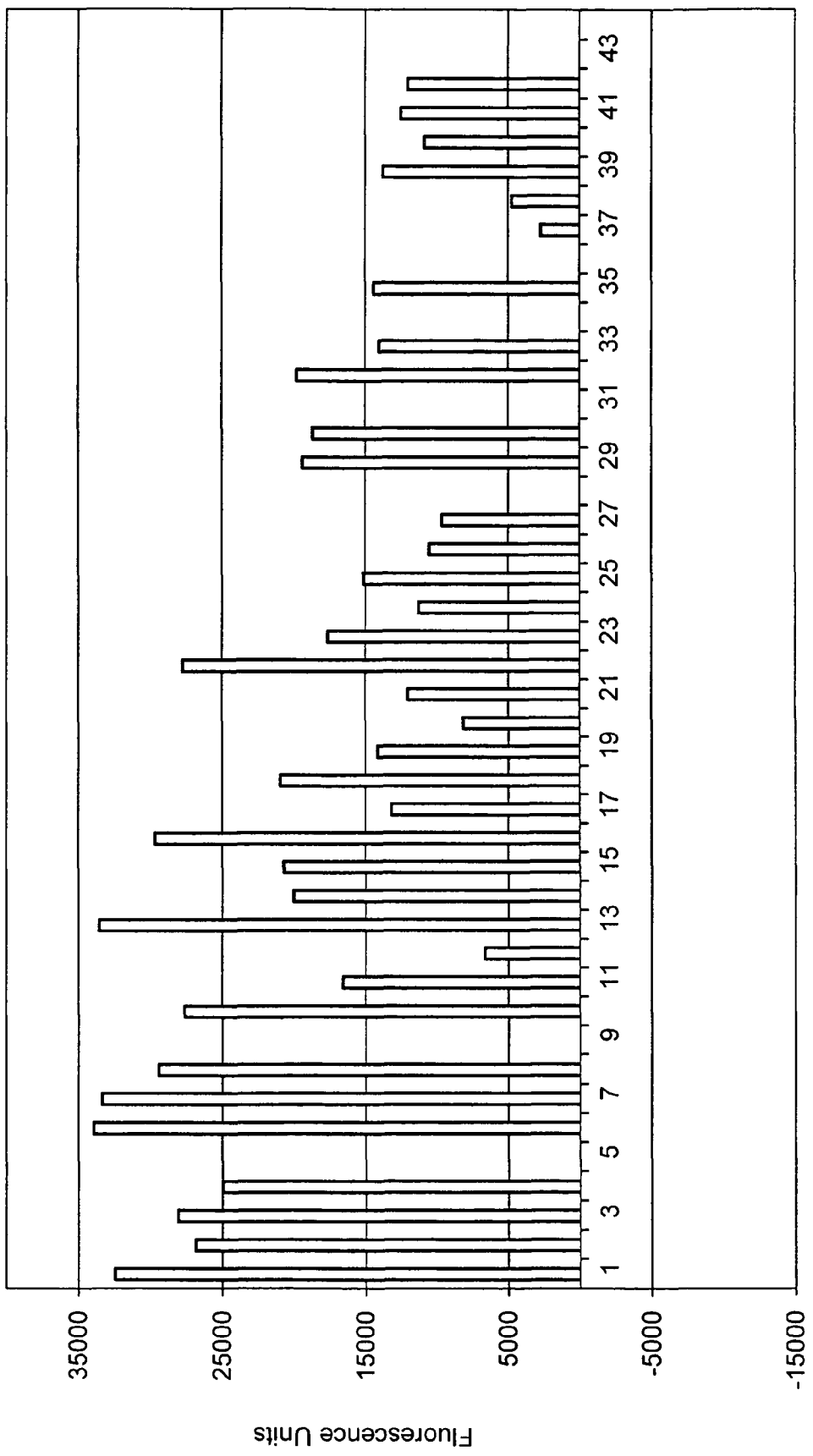
FIG. 33 schematically illustrate plots of the fluorescence signals obtained from the combinations of building blocks employed in the present studies, when those building blocks are covalently linked to the support. Binding was conducted at 23° C.
Figure 39:
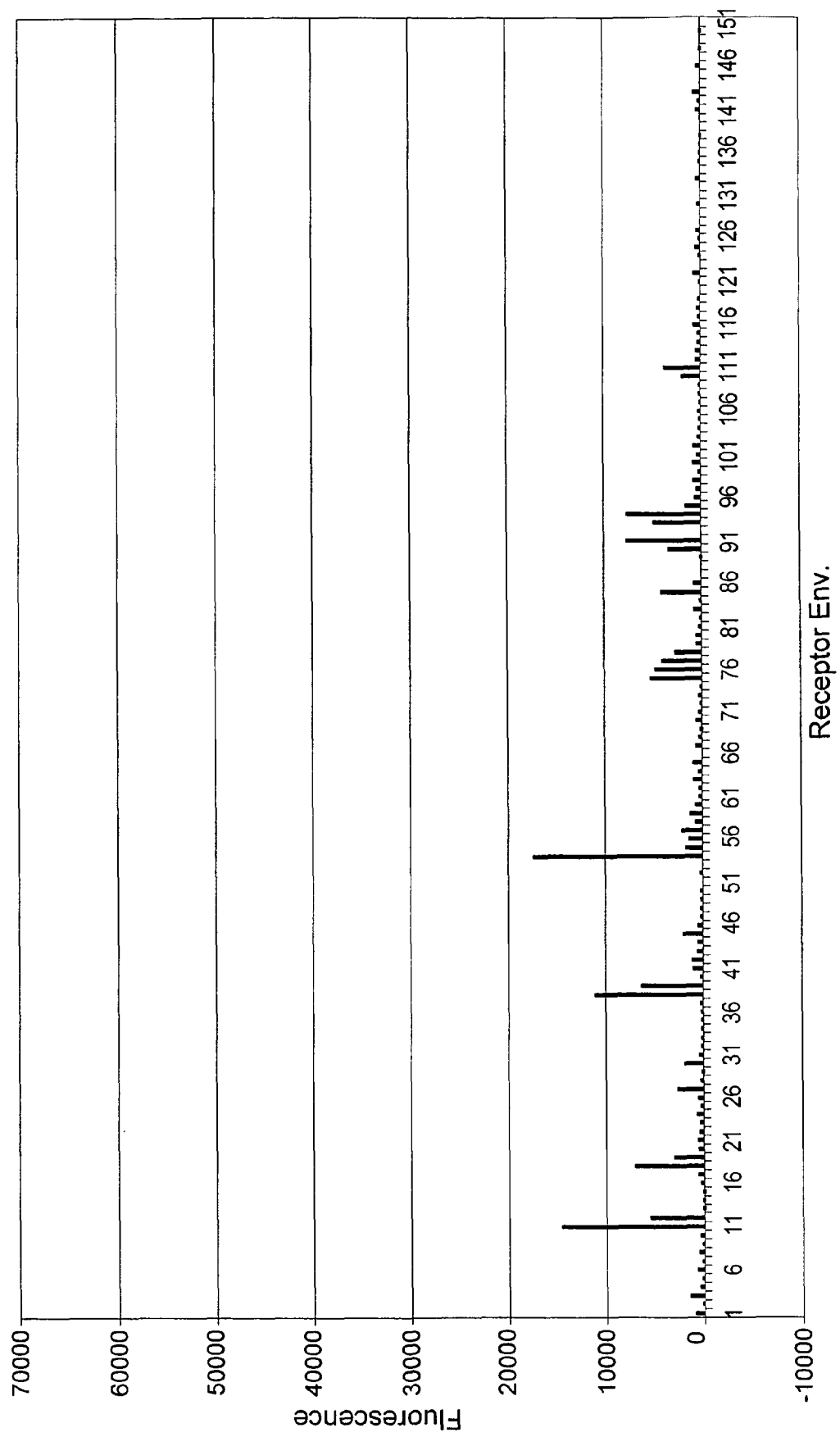
FIG. 39 illustrates the fluorescence signals due to cholera toxin binding that were detected upon competition with GM1 OS (0.34 µM) in an experiment reported in Example 4.

FIG. 33 can be compared to FIG. 39. The fluorescence signals plotted in FIG. 39 resulted from binding to reversibly immobilized building blocks on a support at 23° C. The fluorescence signals plotted in FIG. 33 resulted from binding to covalently immobilized building blocks on a support at 23° C. These figures compare the same combinations of building blocks in the same relative positions, but immobilized in two different ways.

Figure 34:
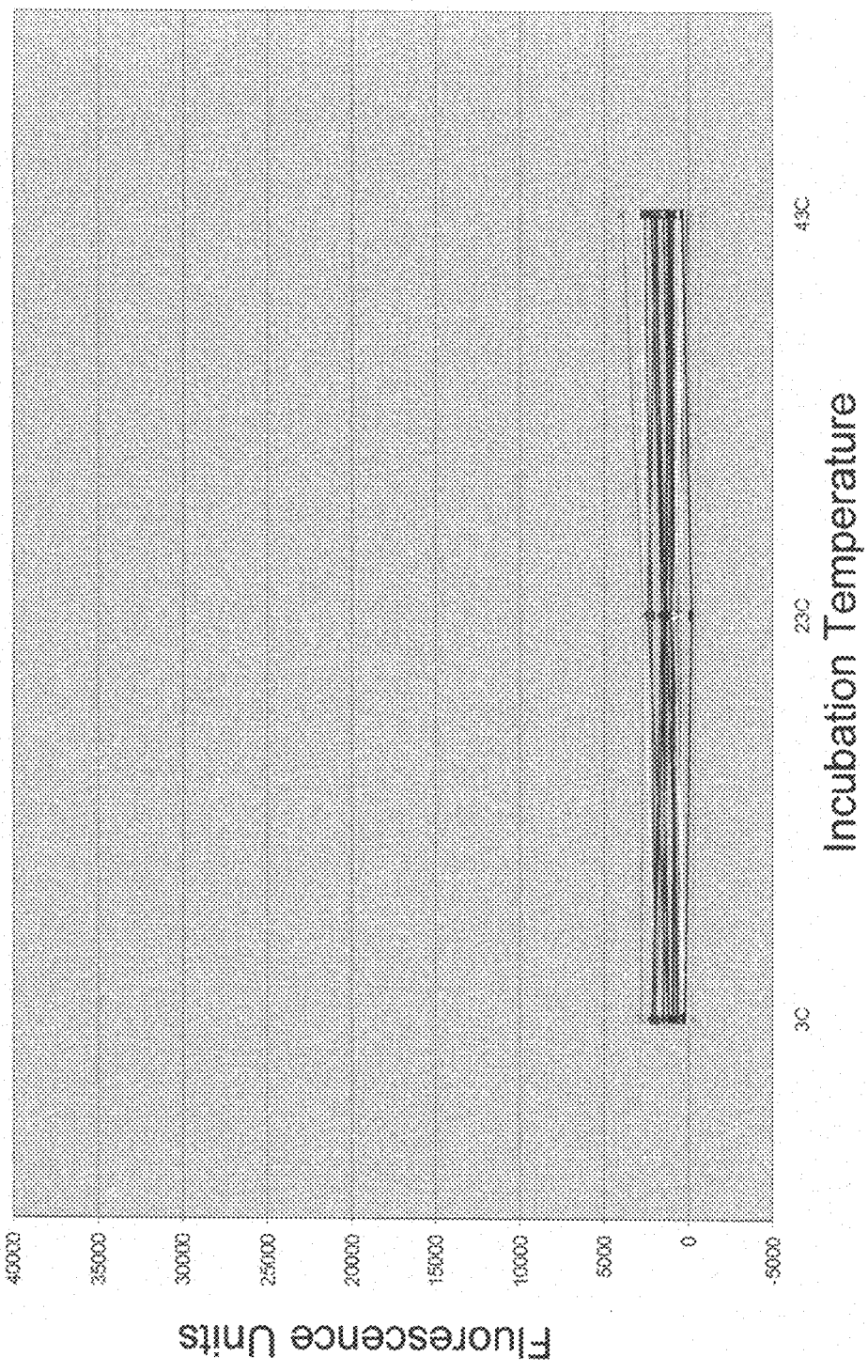
FIG. 34 schematically illustrates the changes in fluorescence signal from individual combinations of covalently immobilized building blocks at 4° C., 23° C., or 44° C.

The binding to covalently immobilized building blocks was also evaluated at 4° C., 23° C., or 44° C. FIG. 34 illustrates the changes in fluorescence signal from individual combinations of covalently immobilized building blocks at 4° C., 23° C., or 44° C. Binding increased modestly with temperature. The mean increase in binding was 1.3-fold. A plot of the fluorescence signal for each of the covalently immobilized artificial receptors at 23° C. against its signal at 44° C. (not shown) yields a linear correlation with a correlation coefficient of 0.75. This linear correlation indicates that the mean 1.3-fold increase in binding is a thermodynamic effect and not optimization of binding.

Figure 35:
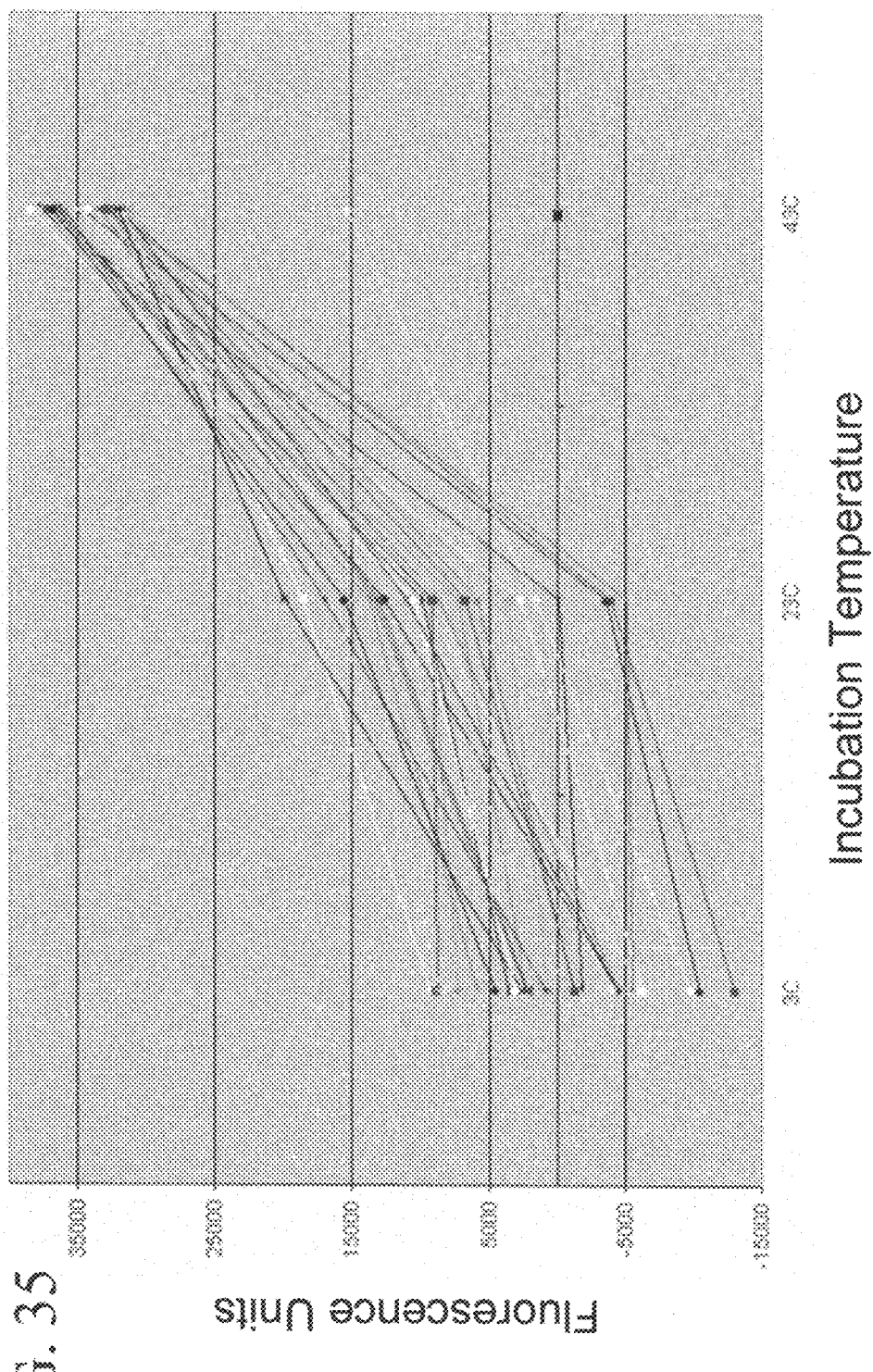
FIG. 35 schematically illustrates a graph of the changes in fluorescence signal from individual combinations of building blocks at 4° C., 23° C., or 44° C.

FIG. 35 illustrates the changes in fluorescence signal from individual combinations of reversibly immobilized building blocks at 4° C., 23° C., or 44° C. This graph illustrates that at least one combination of building blocks (candidate artificial receptor) exhibited a signal that remained constant as temperature increased. At least one candidate artificial receptor exhibited an approximately linear increase in signal as temperature increased. Such a linear increase indicates normal temperature effects on binding. The candidate artificial receptor with the lowest binding signal at 4° C. became one of the best binders at 44° C. This indicates that rearrangement of the building blocks of this receptor above the phase transition for the lawn, which increases the building blocks' mobility, produced increased binding. Other receptors characterized by greater changes in binding between 23° C. and 44° C. (compared to between 4° C. and 23° C.) also underwent dynamic affinity optimization.

FIG. 36 illustrates the data presented in FIG. 34 (lines marked A) and the data presented in FIG. 35 (lines marked B). The increases in binding observed with the reversibly immobilized building blocks are significantly greater than the increases observed with covalently bound building blocks. Binding to reversibly immobilized building blocks increased from 23° C. and 44° C. by a median value of 6.1-fold and a mean value of 24-fold. This confirms that movement of the reversibly immobilized building blocks within the receptors increased binding (i.e., the receptor underwent dynamic affinity optimization).

A plot of the fluorescence signal for each of the reversibly immobilized artificial receptors at 23° C. against its signal at 44° C. (not shown) yields no correlation (correlation coefficient of 0.004). A plot of the fluorescence signal for each of the reversibly immobilized artificial receptors at 44° C. against the signal for the corresponding covalently immobilized receptor (not shown) also yields no correlation (correlation coefficient 0.004). This lack of correlation provides further evidence that movement of the reversibly immobilized building blocks within the receptors increased binding.

Figure 37:
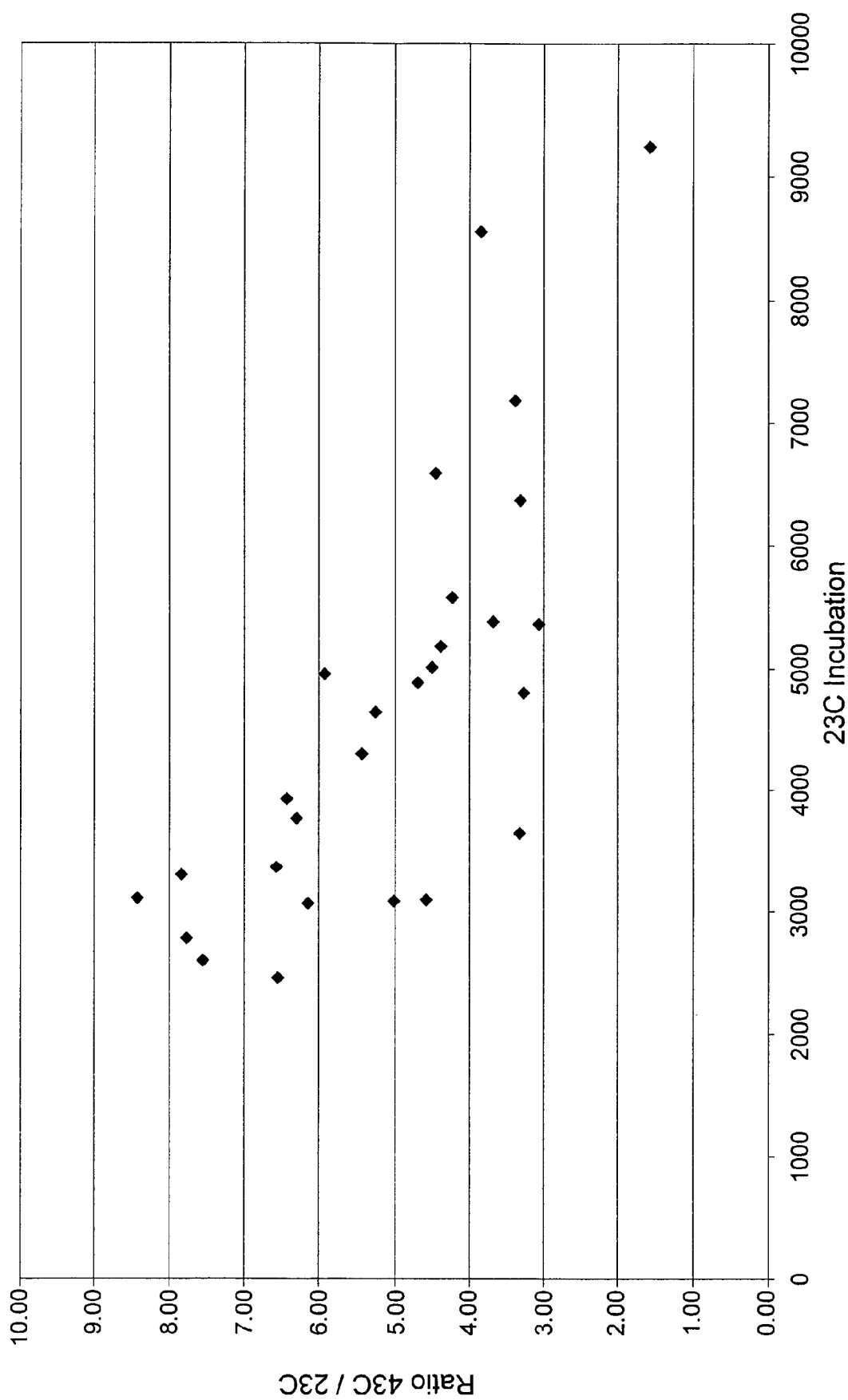
FIG. 37 schematically illustrates a graph of the fluorescence signal at 44° C. divided by the signal at 23° C. against the fluorescence signal obtained from binding at 23° C. for the artificial receptors with reversibly immobilized receptors.

FIG. 37 illustrates a graph of the fluorescence signal at 44° C. divided by the signal at 23° C. against the fluorescence signal obtained from binding at 23° C. for the artificial receptors with reversibly immobilized receptors. This comparison indicates that the binding enhancement is independent of the initial affinity of the receptor for the test ligand.

Table 1 identifies the reversibly immobilized building blocks making up each of the artificial receptors, lists the fluorescence signal (binding strength) at 44° C. and 23° C., and the ratios of the observed binding at these two temperatures. These data illustrate that each artificial receptor reflects a unique attribute for each combination of building blocks relative to the role of each individual building block.

TABLE 1

| Building Blocks Making Up Receptor | Signal at 44° C. | Signal at 23° C. | Ratio of Signals, 44° C./23° C. |
|---|---|---|---|
| 22 24 | 24136 | 4611 | 5.23 |
| 22 26 | 16660 | 43 | 387.44 |
| 22 42 | 17287 | −167 | −103.51 |
| 22 44 | 16726 | 275 | 60.82 |
| 22 46 | 25016 | 3903 | 6.41 |
| 22 62 | 13990 | 3068 | 4.56 |
| 22 64 | 15294 | 3062 | 4.99 |
| 22 66 | 11980 | 3627 | 3.30 |
| 24 26 | 22688 | 1291 | 17.57 |
| 24 42 | 26808 | −662 | −40.50 |
| 24 44 | 23154 | 904 | 25.61 |
| 24 46 | 42197 | 2814 | 15.00 |
| 24 62 | 19374 | 2567 | 7.55 |
| 24 64 | 27599 | 262 | 105.34 |
| 24 66 | 16238 | 5334 | 3.04 |
| 26 42 | 22282 | 4974 | 4.48 |
| 26 44 | 26240 | 530 | 49.51 |
| 26 46 | 23144 | 4273 | 5.42 |
| 26 62 | 29022 | 4920 | 5.90 |
| 26 64 | 23416 | 5551 | 4.22 |
| 26 66 | 19553 | 5353 | 3.65 |
| 42 44 | 29093 | 6555 | 4.44 |
| 42 46 | 18637 | 3039 | 6.13 |
| 42 62 | 22643 | 4853 | 4.67 |
| 42 64 | 20836 | 6343 | 3.28 |
| 42 66 | 14391 | 9220 | 1.56 |
| 44 46 | 25600 | 3266 | 7.84 |
| 44 62 | 15544 | 4771 | 3.26 |
| 44 64 | 25842 | 3073 | 8.41 |
| 44 66 | 22471 | 5142 | 4.37 |
| 46 62 | 32764 | 8522 | 3.84 |
| 46 64 | 21901 | 3343 | 6.55 |
| 46 66 | 23516 | 3742 | 6.28 |
| 62 64 | 24069 | 7149 | 3.37 |
| 62 66 | 15831 | 2424 | 6.53 |
| 64 66 | 21310 | 2746 | 7.76 |

Conclusions

This experiment demonstrated that an array including reversibly immobilized building blocks binds a protein substrate, like an array with covalently immobilized building blocks. The binding increased nonlinearly as temperature increased, indicating that movement of the building blocks increased binding. Many of the candidate artificial receptors demonstrated improved binding upon mobilization of the building blocks.

Example 4

The Oligosaccharide Portion of GM1 Competes with Artificial Receptors for Binding to Cholera Toxin Microarrays of candidate artificial receptors were made and evaluated for binding of cholera toxin. The arrays were also evaluated for disrupting that binding. Disrupting of binding employed a compound that binds to cholera toxin, the oligosaccharide moiety from GM1 (GM1 OS). The results obtained demonstrate that a ligand of a protein specifically disrupted binding of the protein to the microarray.

Materials and Methods

Building blocks were synthesized and activated as described in Example 1. The building blocks employed in this example were TyrA1B1 [1-1], TyrA2B2, TyrA2B4, TyrA2B6, TyrA2B8, TyrA3B3, TyrA3B5, TyrA3B7, TyrA4B2, TyrA4B4, TyrA4B6, TyrA4B8, TyrA5B3, TyrA5B5, TyrA5B7, TyrA6B2, TyrA6B4, TyrA6B6, TyrA6B8, TyrA7B3, TyrA7B5, TyrA7B7, TyrA8B2, TyrA8B4, TyrA8B6, and TyrA8B8. The abbreviation for the building block including a linker, a tyrosine framework, and recognition elements AxBy is TyrAxBy.

Microarrays for the evaluation of the 171 n=2 candidate receptor environments were prepared as follows by modifications of known methods. An "n=2" receptor environment includes two different building blocks. Briefly: Amine modified (amine "lawn"; SuperAmine Microarray plates) microarray plates were purchased from Telechem Inc., Sunnyvale, Calif. These plates were manufactured specifically for microarray preparation and had a nominal amine load of 2-4 amines per square nm according to the manufacturer. The microarrays were prepared using a pin microarray spotter instrument from Telechem Inc. (SpotBot™ Arrayer) typically with 200lm diameter spotting pins from Telechem Inc. (Stealth Micro Spotting Pins, SMP6) and 400-420 μm spot spacing.

The 19 building blocks were activated in aqueous dimethylformamide (DMF) solution as described above. For preparing the 384-well feed plate, the activated building block solutions were diluted 10-fold with a solution of DMF/H$_2$O/PEG400 (90/10/10, v/v/v; PEG400 is polyethylene glycol nominal 400 FW, Aldrich Chemical Co., Milwaukee, Wis.). These stock solutions were aliquotted (10 μl per aliquot) into the wells of a 384-well microwell plate (Telechem Inc.). Control spots included the building block [1-1]. The plate was covered with aluminum foil and placed on the bed of a rotary shaker for 15 minutes at 1,000 RPM. This master plate was stored covered with aluminum foil at −20° C. when not in use.

For preparing the 384-well SpotBot™ plate, a well-to-well transfer (e.g. A-1 to A-1, A-2 to A-2, etc.) from the feed plate to a second 384-well plate was performed using a 4 μl transfer pipette. This plate was stored tightly covered with aluminum foil at −20° C. when not in use. The SpotBot™ was used to prepare up to 13 microarray plates per run using the 4 μl microwell plate. The SpotBot™ was programmed to spot from each microwell in quadruplicate. The wash station on the SpotBot™ used a wash solution of EtOH/H2O (20/80, v/v). This wash solution was adjusted to pH 4 with 1 M HCl and used to rinse the microarrays on completion of the SpotBot™ printing run. The plates were given a final rinse with deionized (DI) water, dried using a stream of compressed air, and stored at room temperature. The microarrays were further modified by reacting the remaining amines with acetic anhydride to form an acetamide lawn in place of the amine lawn.

The test ligand employed in these experiments was cholera toxin labeled with the Alexa™ fluorophore (Molecular Probes Inc., Eugene, Oreg.). The candidate disruptor employed in these experiments was GM1 OS (GM1 oligosaccharide), a known ligand for cholera toxin.

Microarray incubation and analysis was conducted as follows: For control incubations with the microarrays, solutions (e.g. 500 μl) of the cholera toxin in PBS-T (PBS with 20 μl/L of Tween-20) at a concentrations of 1.7 pmol/ml (0.1 μg/ml) was placed onto the surface of a microarray and allowed to react for 30 minutes. For disruptor incubations with the microarrays, solutions (e.g. 500 μl) of the cholera toxin (1.7 pmol/ml, 0.1 g/ml) and the desired concentration of GM1 OS in PBS-T (PBS with 20 μl/L of Tween-20) was placed onto the surface of a microarray and allowed to react for 30 minutes. GM1 OS was added at 0.34 and at 5.1 μM in separate experiments. After either of these incubations, the microarray was rinsed with PBS-T and DI water and dried using a stream of compressed air.

The incubated microarray was scanned using an Axon Model 4200A Fluorescence Microarray Scanner (Axon Instruments, Union City, Calif.). The Axon scanner and its associated software produce a false color 16-bit image of the fluorescence intensity of the plate. This 16-bit data is integrated using the Axon software to give a Fluorescence Units value (range 0-65,536) for each spot on the microarray. This data is then exported into an Excel file (Microsoft) for further analysis including mean, standard deviation and coefficient of variation calculations.

Table 2 identified the building blocks in each of the first 150 receptor environments.

TABLE 2

| | Building Blocks |
|---|---|
| 1 | 22 24 |
| 2 | 22 28 |
| 3 | 22 42 |
| 4 | 22 46 |
| 5 | 22 55 |
| 6 | 22 64 |
| 7 | 22 68 |
| 8 | 22 82 |
| 9 | 22 86 |
| 10 | 24 26 |
| 11 | 24 33 |
| 12 | 24 44 |
| 13 | 26 77 |
| 14 | 26 84 |
| 15 | 26 88 |
| 16 | 28 42 |
| 17 | 22 26 |
| 18 | 22 33 |
| 19 | 22 44 |
| 20 | 22 48 |
| 21 | 22 62 |
| 22 | 22 66 |
| 23 | 22 77 |
| 24 | 22 84 |
| 25 | 22 88 |
| 26 | 24 28 |
| 27 | 24 42 |
| 28 | 26 82 |
| 29 | 26 85 |
| 30 | 28 33 |
| 31 | 28 44 |
| 32 | 28 46 |
| 33 | 28 55 |
| 34 | 28 64 |
| 35 | 28 68 |
| 36 | 28 82 |
| 37 | 28 86 |
| 38 | 33 42 |
| 39 | 33 46 |
| 40 | 42 88 |
| 41 | 44 48 |
| 42 | 44 62 |
| 43 | 44 66 |
| 44 | 44 77 |
| 45 | 44 84 |
| 46 | 44 88 |
| 47 | 46 55 |
| 48 | 28 48 |
| 49 | 28 62 |

TABLE 2-continued

| | Building Blocks | |
|---|---|---|
| 50 | 28 | 66 |
| 51 | 28 | 77 |
| 52 | 28 | 84 |
| 53 | 28 | 88 |
| 54 | 33 | 44 |
| 55 | 44 | 46 |
| 56 | 44 | 55 |
| 57 | 44 | 64 |
| 58 | 44 | 68 |
| 59 | 44 | 82 |
| 60 | 44 | 86 |
| 61 | 46 | 48 |
| 62 | 46 | 62 |
| 63 | 24 | 46 |
| 64 | 24 | 55 |
| 65 | 24 | 64 |
| 66 | 24 | 68 |
| 67 | 24 | 82 |
| 68 | 24 | 86 |
| 69 | 26 | 28 |
| 70 | 26 | 42 |
| 71 | 26 | 46 |
| 72 | 26 | 55 |
| 73 | 26 | 64 |
| 74 | 26 | 68 |
| 75 | 33 | 48 |
| 76 | 33 | 63 |
| 77 | 33 | 66 |
| 78 | 33 | 77 |
| 79 | 24 | 48 |
| 80 | 24 | 62 |
| 81 | 24 | 66 |
| 82 | 24 | 77 |
| 83 | 24 | 84 |
| 84 | 24 | 88 |
| 85 | 26 | 33 |
| 86 | 26 | 44 |
| 87 | 26 | 48 |
| 88 | 26 | 62 |
| 89 | 26 | 66 |
| 90 | 33 | 55 |
| 91 | 33 | 64 |
| 92 | 33 | 68 |
| 93 | 33 | 82 |
| 94 | 33 | 84 |
| 95 | 33 | 88 |
| 96 | 42 | 46 |
| 97 | 42 | 55 |
| 98 | 42 | 64 |
| 99 | 42 | 68 |
| 100 | 42 | 82 |
| 101 | 42 | 86 |
| 102 | 46 | 88 |
| 103 | 48 | 62 |
| 104 | 48 | 66 |
| 105 | 46 | 77 |
| 106 | 48 | 84 |
| 107 | 48 | 88 |
| 108 | 55 | 64 |
| 109 | 55 | 68 |
| 110 | 33 | 86 |
| 111 | 42 | 44 |
| 112 | 42 | 48 |
| 113 | 42 | 62 |
| 114 | 42 | 66 |
| 115 | 42 | 77 |
| 116 | 42 | 84 |
| 117 | 48 | 55 |
| 118 | 48 | 64 |
| 119 | 48 | 68 |
| 120 | 48 | 82 |
| 121 | 48 | 86 |
| 122 | 55 | 62 |
| 123 | 55 | 66 |
| 124 | 55 | 77 |
| 125 | 46 | 64 |
| 126 | 46 | 68 |
| 127 | 46 | 82 |
| 128 | 46 | 86 |
| 129 | 62 | 77 |
| 130 | 62 | 84 |
| 131 | 62 | 88 |
| 132 | 64 | 68 |
| 133 | 64 | 82 |
| 134 | 64 | 86 |
| 135 | 66 | 68 |
| 136 | 66 | 82 |
| 137 | 66 | 86 |
| 138 | 68 | 77 |
| 139 | 68 | 84 |
| 140 | 68 | 88 |
| 141 | 46 | 66 |
| 142 | 46 | 77 |
| 143 | 46 | 84 |
| 144 | 62 | 82 |
| 145 | 62 | 86 |
| 146 | 64 | 66 |
| 147 | 64 | 77 |
| 148 | 64 | 84 |
| 149 | 64 | 88 |
| 150 | 66 | 77 |

Results

Low Concentration of GM1 OS

Figure 38:
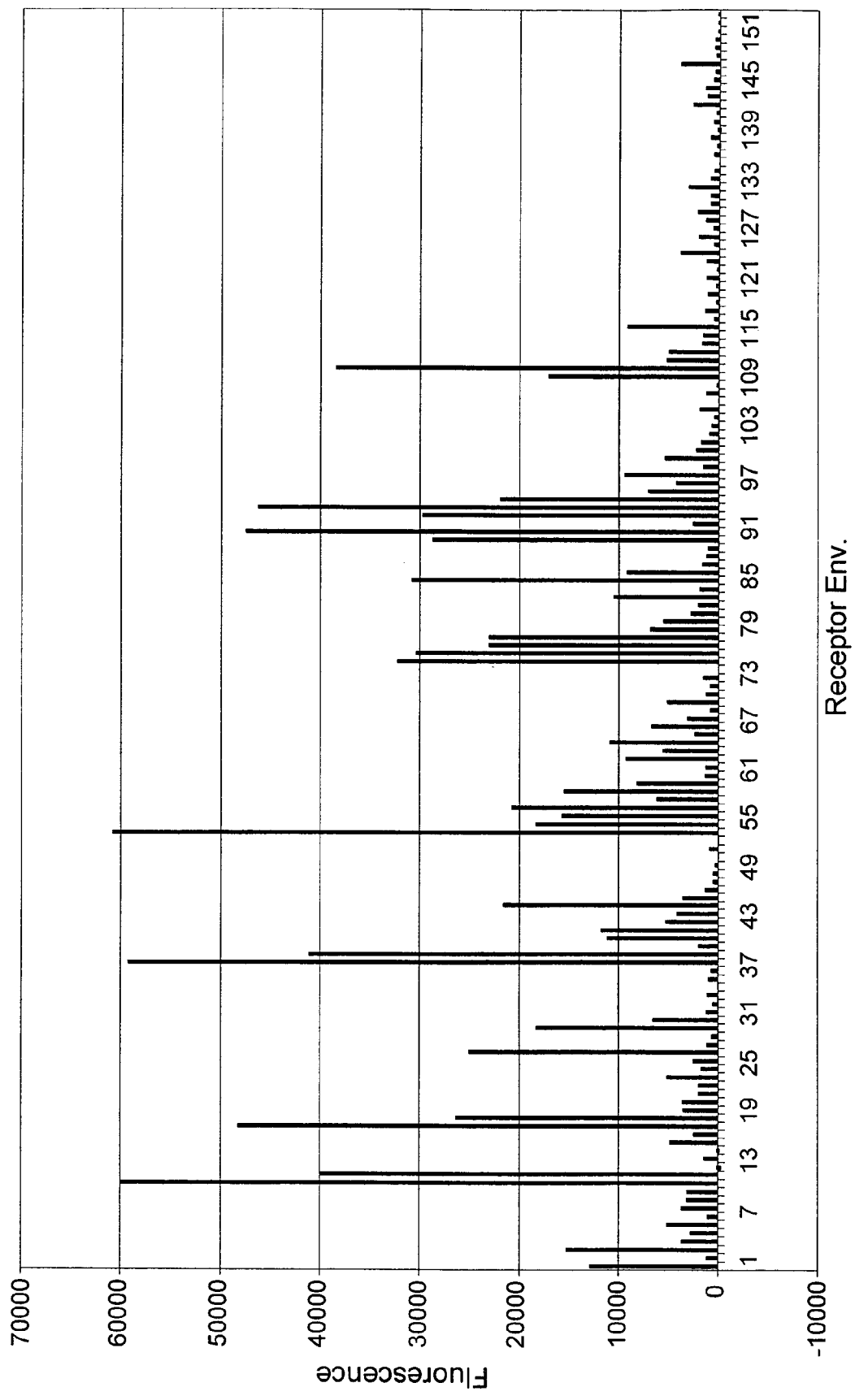
FIG. 38 illustrates fluorescence signals produced by binding of cholera toxin to a microarray of the present candidate artificial receptors followed by washing with buffer in an experiment reported in Example 4.

FIG. 38 illustrates binding of cholera toxin to the microarray of candidate artificial receptor followed by washing with buffer produced fluorescence signals. These fluorescence signals demonstrate that the cholera toxin bound strongly to certain receptor environments, weakly to others, and undetectably to some. Comparison to experiments including those reported in Example 2 indicates that cholera toxin binding was reproducible from array to array and from month to month.

Binding of cholera toxin was also conducted with competition from GM1 OS (0.34 µM). FIG. 39 illustrates the fluorescence signals due to cholera toxin binding that were detected after this competition. Notably, many of the signals illustrated in FIG. 39 are significantly smaller than the corresponding signals recorded in FIG. 38. The small signals observed in FIG. 39 represent less cholera toxin bound to the array. GM1 OS significantly disrupted binding of cholera toxin to many of the receptor environments.

Figure 40:
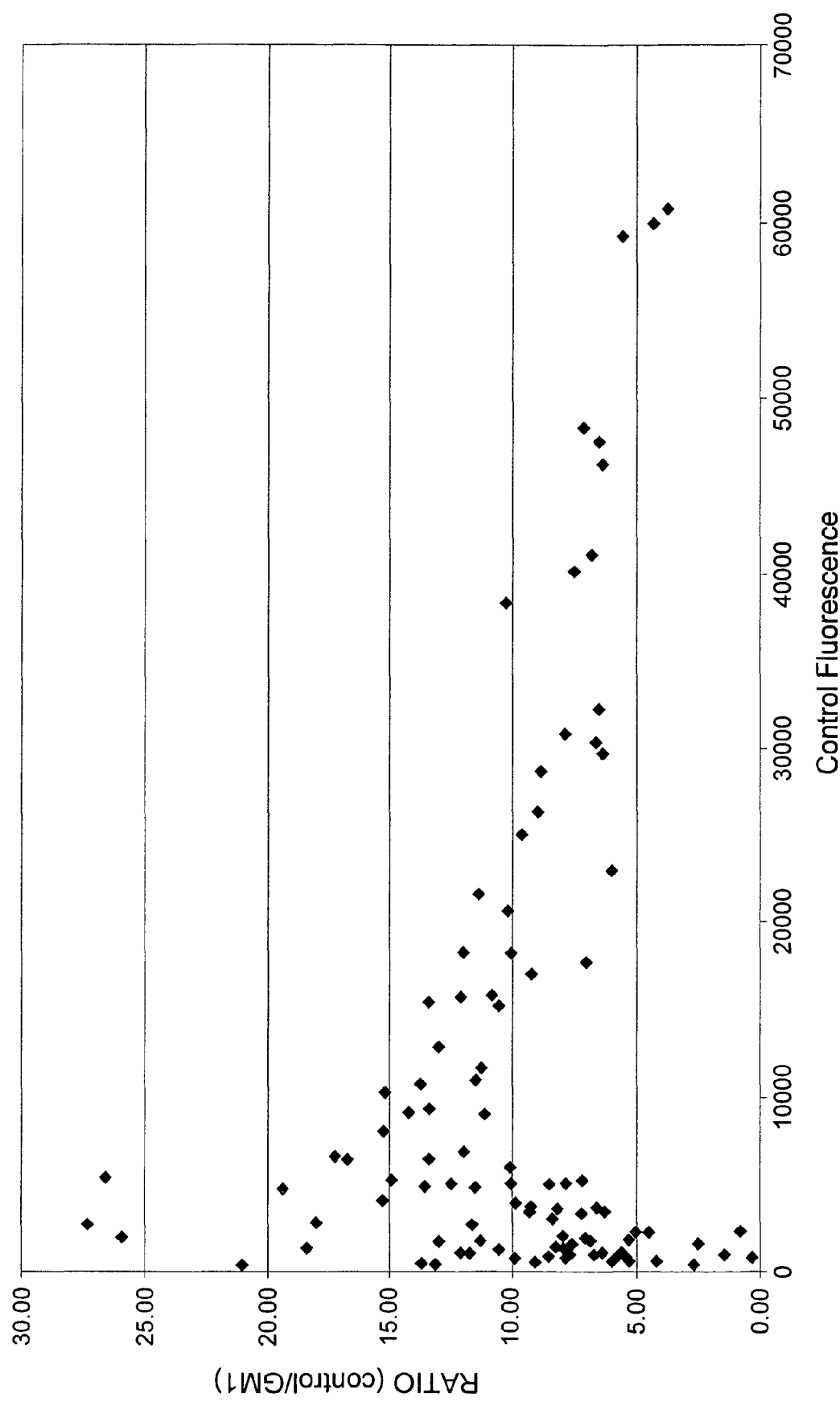
FIG. 40 illustrates the ratio of the amount bound in the absence of GM1 OS to the amount bound in competition with GM1 OS (0.34 µM) in an experiment reported in Example 4.

The disruption in cholera toxin binding caused by GM1 OS can be visualized as the ratio of the amount bound in the absence of GM1 OS to the amount bound in competition with GM1 OS. This ratio is illustrated in FIG. 40. The larger the ratio, the less cholera toxin remained bound to the artificial receptor after competition with GM1 OS. The ratio can be as large as about 30. The ratios are independent of the quantity bound in the control.

High Concentration of GM1 OS

Figure 41:
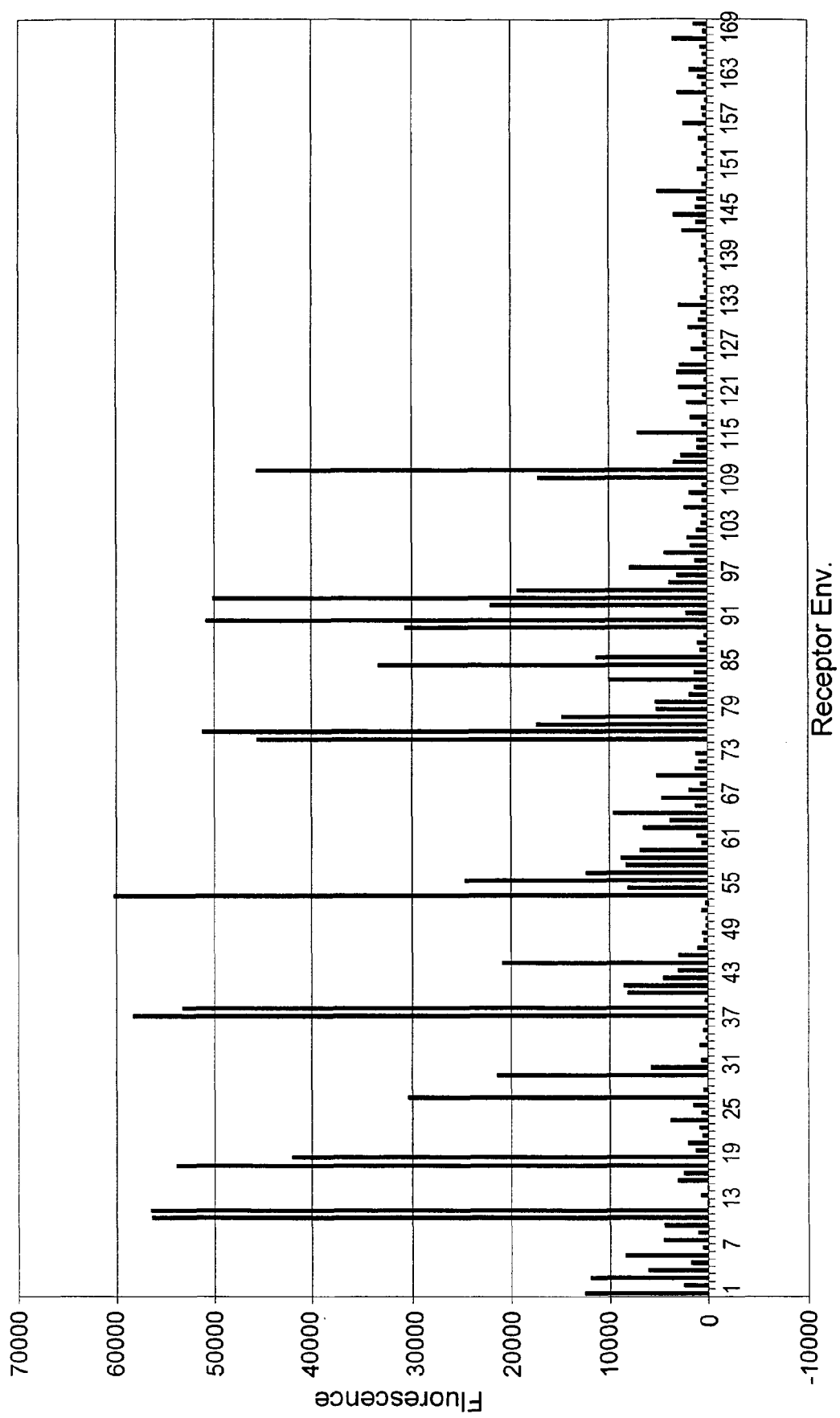
FIG. 41 illustrates fluorescence signals produced by binding of cholera toxin to a microarray of the present candidate artificial receptors followed by washing with buffer in an experiment reported in Example 4 and for comparison with competition experiments using 5.1 µM GM1 OS.
Figure 42:
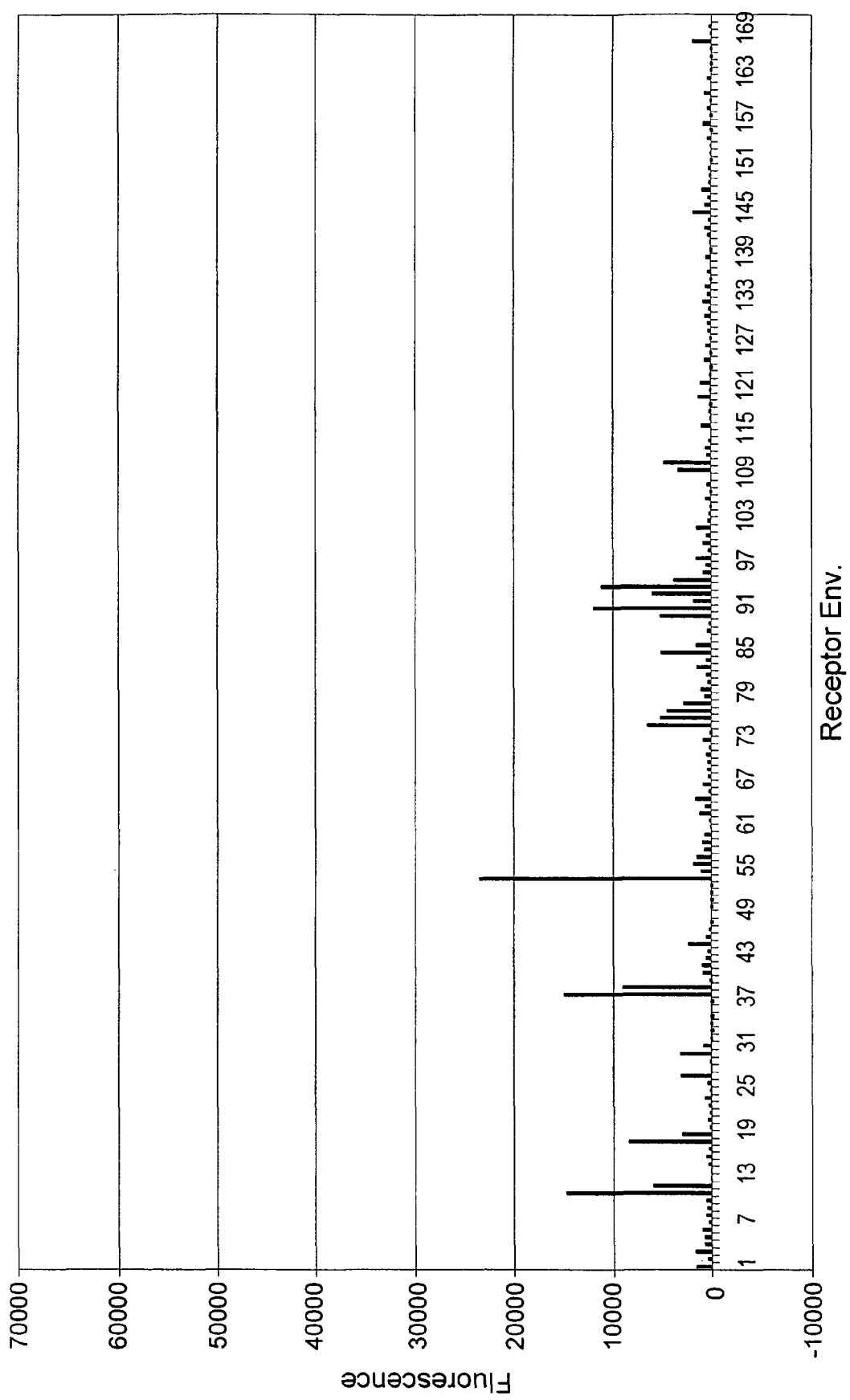
FIG. 42 illustrates the fluorescence signals due to cholera toxin binding that were detected upon competition with GM1 OS (5.1 µM) in an experiment reported in Example 4.
Figure 43:
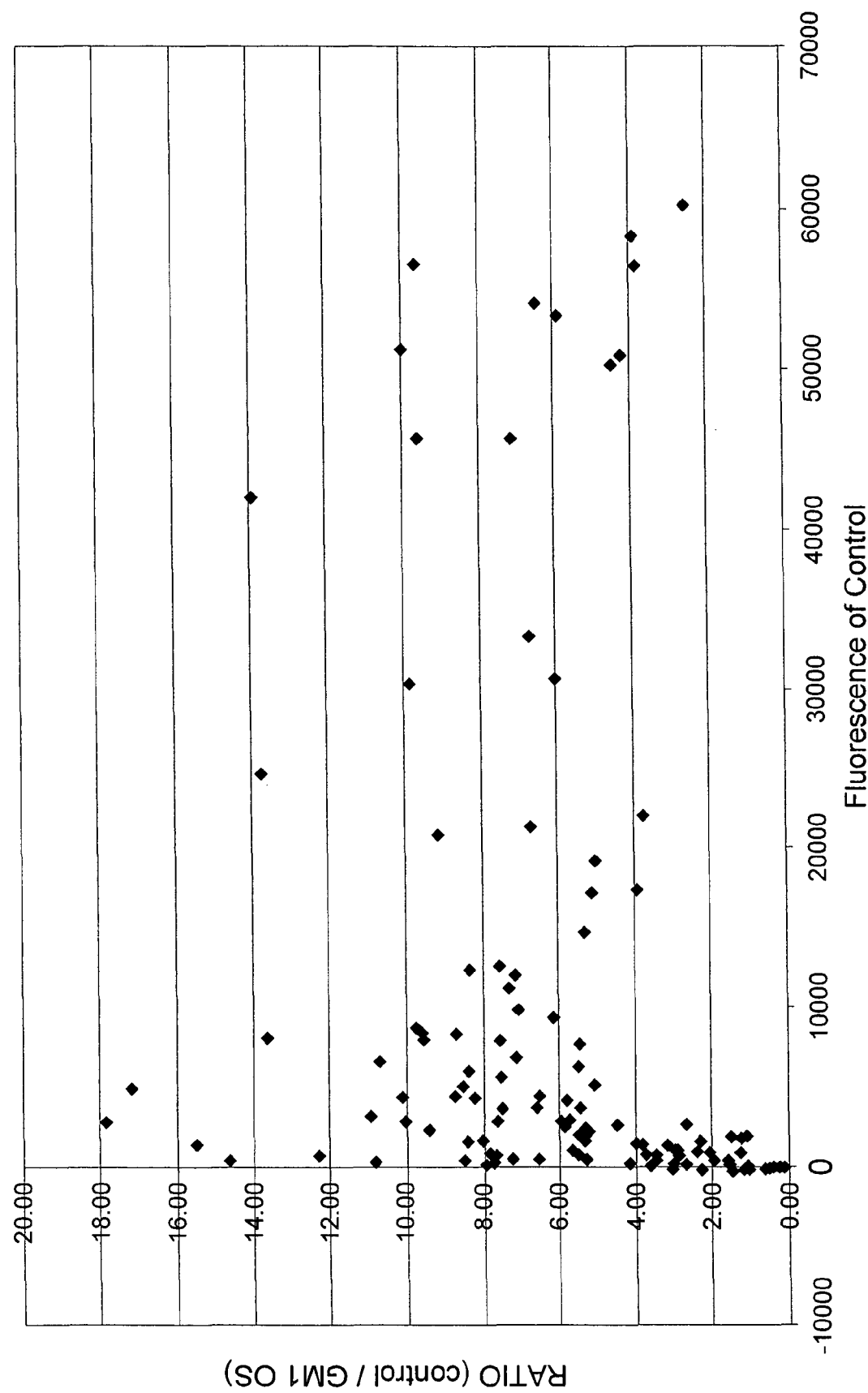
FIG. 43 illustrates the ratio of the amount bound in the absence of GM1 OS to the amount bound in competition with GM1 OS (5.1 µM) in an experiment reported in Example 4.

Binding of cholera toxin to the microarray of candidate artificial receptors followed by washing with buffer produced fluorescence signals illustrated in FIG. 41. As before, cholera toxin was reproducible and it bound strongly to certain receptor environments, weakly to others, and undetectably to some. FIG. 42 illustrates the fluorescence signals detected due to cholera toxin binding that were detected upon competition with GM1 OS at 5.1 µM. Again, GM1 OS significantly disrupted binding of cholera toxin to many of the receptor environments.

Figure 44:
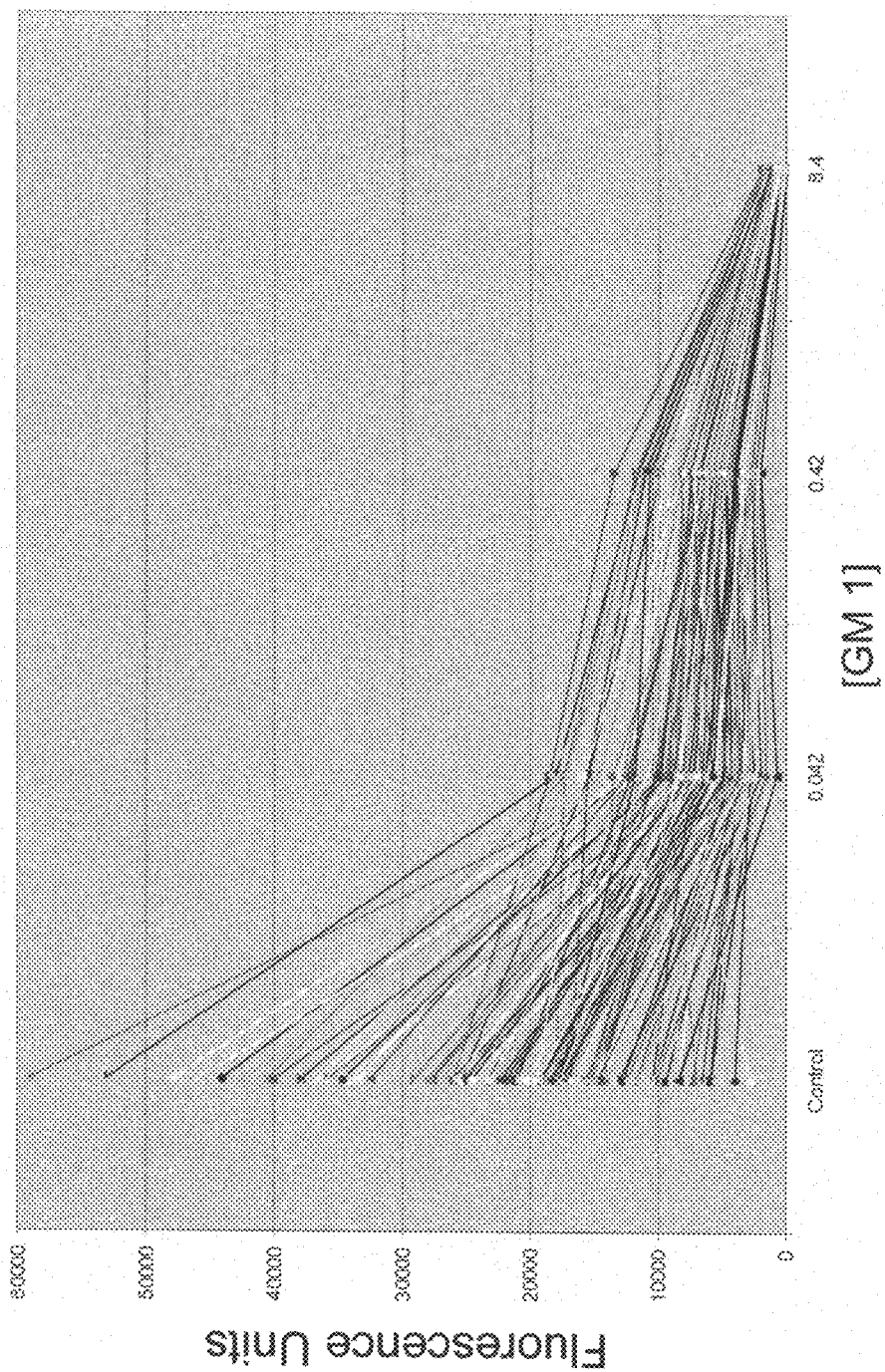
FIG. 44 illustrates the fluorescence signals produced by binding of cholera toxin to the microarray of candidate artificial receptors alone and in competition with each of the three concentrations of GM1 in the experiment reported in Example 5.

This disruption is presented as the ratio of the amount bound in the absence of GM1 OS to the amount bound after contacting with GM1 OS in FIG. 44. The ratios range up to about 18 and are independent of the quantity bound in the control.

Conclusions

This experiment demonstrated that binding of a test ligand to an artificial receptor of the present invention can be diminished (e.g., competed) by a candidate disruptor molecule. In this case the test ligand was the protein cholera toxin and the candidate disruptor was a compound known to bind to cholera toxin, GM1 OS. The degree to which binding of the test ligand was disrupted was independent of the degree to which the test ligand bound to the artificial receptor.

Example 5

GM1 Competes with Artificial Receptors for Binding to Cholera Toxin

Microarrays of candidate artificial receptors were made and evaluated for binding of cholera toxin. The arrays were also evaluated for disrupting that binding. Disrupting of binding employed a compound that binds to cholera toxin, the liposaccharide GM1. The results obtained demonstrate that a ligand of a protein specifically disrupts binding of the protein to the microarray.

Materials and Methods

Building blocks were synthesized and activated as described in Example 1. The building blocks employed in this example were TyrA1B1 [1-1], TyrA2B2, TyrA2B4, TyrA2B6, TyrA4B2, TyrA4B4, TyrA4B6, TyrA6B2, TyrA6B4, and TyrA6B6 in groups of 4 building blocks per artificial receptor. The abbreviation for the building block including a linker, a tyrosine framework, and recognition elements AxBy is TyrAxBy.

Microarrays for the evaluation of the 126 n=4 candidate receptor environments were prepared as described above for Example 4. The test ligand employed in these experiments was cholera toxin labeled with the Alexa™ fluorophore (Molecular Probes Inc., Eugene, Oreg.). Cholera toxin was employed at 5.3 nM in both the control and the competition experiments. The candidate disruptor employed in these experiments was GM1, a known ligand for cholera toxin, which competed at concentrations of 0.042, 0.42, and 8.4 µM. Microarray incubation and analysis was conducted as described for Example 4.

Table 3 identifies the building blocks in each receptor environment.

TABLE 3

| | Building Blocks |
|---|---|
| 1 | 22 24 26 42 |
| 2 | 22 24 26 44 |
| 3 | 22 24 26 46 |
| 4 | 22 24 26 61 |
| 5 | 22 24 26 64 |
| 6 | 22 24 26 66 |
| 7 | 22 24 42 44 |
| 8 | 22 24 42 46 |
| 9 | 22 24 42 62 |
| 10 | 22 24 42 46 |
| 11 | 22 24 42 66 |
| 12 | 22 24 44 46 |
| 13 | 22 24 44 62 |
| 14 | 22 24 44 64 |
| 15 | 22 24 44 66 |
| 16 | 22 24 46 62 |
| 17 | 22 24 46 64 |
| 18 | 22 24 46 66 |
| 19 | 22 24 62 64 |
| 20 | 22 24 62 66 |
| 21 | 22 24 64 66 |
| 22 | 22 26 42 44 |
| 23 | 22 26 42 46 |
| 24 | 22 26 42 62 |
| 25 | 22 26 42 64 |
| 26 | 22 26 42 66 |
| 27 | 22 26 44 46 |
| 28 | 22 26 44 62 |
| 29 | 22 26 44 64 |
| 30 | 22 26 44 66 |
| 31 | 22 26 46 62 |
| 32 | 22 26 46 64 |
| 33 | 22 26 46 66 |
| 34 | 22 26 62 64 |
| 35 | 22 26 62 66 |
| 36 | 22 26 64 66 |
| 37 | 22 42 44 46 |
| 38 | 22 42 44 62 |
| 39 | 22 42 44 64 |
| 40 | 22 42 44 66 |
| 41 | 22 42 46 62 |
| 42 | 22 42 46 64 |
| 43 | 22 42 46 66 |
| 44 | 22 42 62 64 |
| 45 | 22 42 62 66 |
| 46 | 22 42 64 66 |
| 47 | 22 44 46 62 |
| 48 | 22 44 46 64 |
| 49 | 22 44 46 66 |
| 50 | 22 44 62 64 |
| 51 | 22 44 62 66 |
| 52 | 22 44 64 66 |
| 53 | 22 46 62 64 |
| 54 | 22 46 62 66 |
| 55 | 22 46 64 66 |
| 56 | 22 62 64 66 |
| 57 | 24 26 42 44 |
| 58 | 24 26 42 46 |
| 59 | 24 26 42 62 |
| 60 | 24 26 42 64 |
| 61 | 24 26 42 66 |
| 62 | 24 26 44 46 |
| 63 | 24 26 44 62 |
| 64 | 24 26 44 64 |
| 65 | 24 26 44 66 |
| 66 | 24 26 46 62 |
| 67 | 24 26 46 64 |
| 68 | 24 26 46 66 |
| 69 | 24 26 62 64 |
| 70 | 24 26 62 66 |
| 71 | 24 26 64 66 |
| 72 | 24 42 44 46 |
| 73 | 24 42 44 62 |
| 74 | 24 42 44 64 |
| 75 | 24 42 44 66 |
| 76 | 24 42 46 62 |
| 77 | 24 42 46 64 |
| 78 | 24 42 46 66 |
| 79 | 24 42 62 64 |
| 80 | 24 42 62 66 |
| 81 | 24 42 64 66 |
| 82 | 24 44 46 62 |
| 83 | 24 44 46 64 |
| 84 | 24 44 46 66 |
| 85 | 24 44 62 64 |
| 86 | 24 44 62 66 |
| 87 | 24 44 64 66 |
| 88 | 24 46 62 64 |
| 89 | 24 46 62 66 |
| 90 | 24 46 64 66 |
| 91 | 24 62 64 66 |
| 92 | 26 42 44 46 |
| 93 | 26 42 44 62 |
| 94 | 26 42 44 64 |

TABLE 3-continued

| | Building Blocks |
|---|---|
| 95 | 26 42 44 66 |
| 96 | 26 42 46 62 |
| 97 | 26 42 46 64 |
| 98 | 26 42 46 66 |
| 99 | 26 42 62 64 |
| 100 | 26 42 62 66 |
| 101 | 26 42 64 66 |
| 102 | 26 44 46 62 |
| 103 | 26 44 46 64 |
| 104 | 26 44 46 66 |
| 105 | 26 44 62 64 |
| 106 | 26 44 62 66 |
| 107 | 26 44 64 66 |
| 108 | 26 46 62 64 |
| 109 | 26 46 62 66 |
| 110 | 26 46 64 66 |
| 111 | 26 62 64 66 |
| 112 | 42 44 46 62 |
| 113 | 42 44 46 64 |
| 114 | 42 44 46 66 |
| 115 | 42 44 62 64 |
| 116 | 42 44 62 66 |
| 117 | 42 44 64 66 |
| 118 | 42 46 62 64 |
| 119 | 42 46 62 66 |
| 120 | 42 46 64 66 |
| 121 | 42 62 64 66 |
| 122 | 44 46 62 64 |
| 123 | 44 46 62 66 |
| 124 | 44 46 64 66 |
| 125 | 44 62 64 66 |
| 126 | 46 62 64 66 |

Results

FIG. 44 illustrates the fluorescence signals produced by binding of cholera toxin to the microarray of candidate artificial receptors alone and in competition with each of the three concentration of GM1. The magnitude of the fluorescence signal decreases steadily with increasing concentration of GM1. The amount of decrease is not quantitatively identical for all of the receptor, but each receptor experienced decreased binding of cholera toxin. These decreases indicate that GM1 competed with the artificial receptor for binding to the cholera toxin.

The decreases show a pattern of relative competition for the binding site on cholera toxin. This can be demonstrated through graphs of fluorescence signal obtained at a particular concentration of GM1 against fluorescence signal in the absence of GM1 (not shown). Certain of the receptors appear at similar relative positions on these plots as concentration of GM1 increases.

Figure 45:
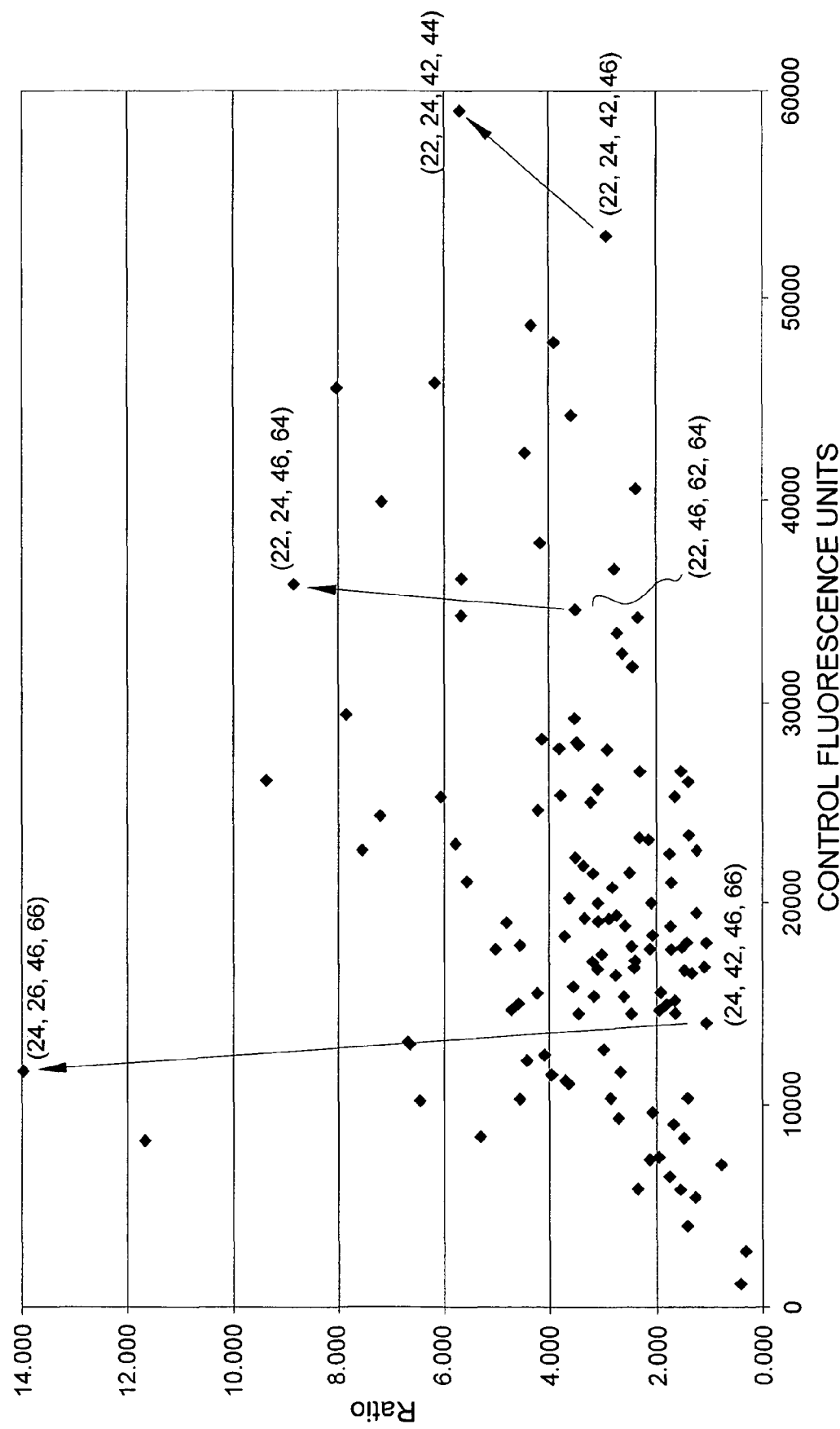
FIG. 45 illustrates the ratio of the amount bound in the absence of GM1 OS to the amount bound upon competition with GM1 for the low concentration of GM1 employed in Example 5.

The disruption in cholera toxin binding caused by GM1 can be visualized as the ratio of the amount bound in the absence of GM1 OS to the amount bound upon competition with GM1. This ratio is illustrated in FIG. 45. The larger the ratio, the more cholera toxin remained bound to the artificial receptor upon competition with GM1. The ratio can be as large as about 14. The ratios are independent of the quantity bound in the control.

Interestingly, in several instances minor changes in structure to the artificial receptor caused significant changes in the ratio. For example, the artificial receptor including building blocks 24, 26, 46, and 66 differs from that including 24, 42, 46, and 66 by only substitution of a single building block. (xy indicates building block TyrAxBy.) The substitution of building block 42 for 26 increased binding in the presence of GM1 by about 14-fold.

By way of further example, the artificial receptor including building blocks 22, 24, 46, and 64 differs from that including 22, 46, 62, and 64 by only substitution of a single building block. The substitution of building block 24 for 62 increased binding in the presence of GM1 by about 3-fold.

Even substitution of a single recognition element affected binding. The artificial receptor including building blocks 22, 24, 42, and 44 differs from that including 22, 24, 42, and 46 by only substitution of a single recognition element. The substitution of building block 44 for 46 (a change of recognition element B6 to B4) increased binding in the presence of GM1 by about 3-fold.

Conclusions

This experiment demonstrated that binding of a test ligand to an artificial receptor of the present invention can be diminished (e.g., competed) by a candidate disruptor molecule. In this case the test ligand was the protein cholera toxin and the candidate disruptor was a compound known to bind to cholera toxin, GM1. Minor changes in structure of the building blocks making up the artificial receptor caused significant changes in the competition.

Example 6

GM1 Employed as a Building Block Alters Binding of Cholera Toxin to the Present Artificial Receptors Microarrays of candidate artificial receptors were made, GM1 was bound to the arrays, and they were evaluated for binding of cholera toxin. The results obtained demonstrate that adding GM1 as a building block in an array of artificial receptors can increase binding to certain of the receptors.

Materials and Methods

Building blocks were synthesized and activated as described in Example 1. The building blocks employed in this example were those described in Example 4. Microarrays for the evaluation of the 171 n=2 candidate receptor environments were prepared as described above for Example 4. The test ligand employed in these experiments was cholera toxin labeled with the Alexa™ fluorophore (Molecular Probes Inc., Eugene, Oreg.). Cholera toxin was employed at 0.01 µg/1 ml (0.17 pM) or 0.1 µg/ml (1.7 pM) in both the control and the competition experiments. GM1 was employed as a test ligand for the artificial receptors and became a building block for receptors used to bind cholera toxin. The arrays were contacted with GM1 at either 100 µg/ml, 10 µg/ml, or 1 µg/ml as described above for cholera toxin and then rinsed with deionized water. The arrays were then contacted with cholera toxin under the conditions described above. Microarray analysis was conducted as described for Example 4. Table 2 identifies the building blocks in each receptor environment.

Results

Figure 46:
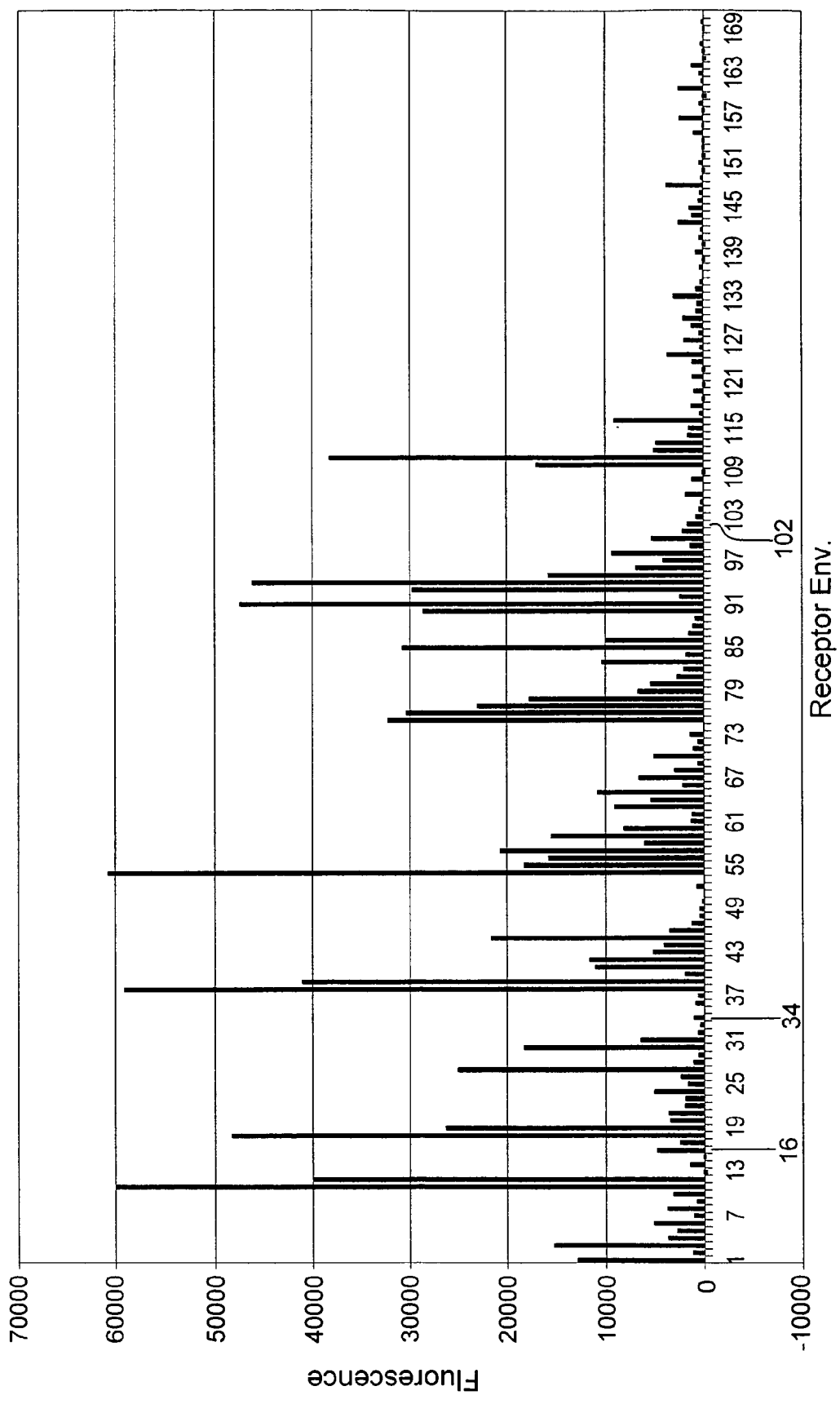
FIG. 46 illustrates the fluorescence signals produced by binding of cholera toxin to the microarray of candidate artificial receptors without pretreatment with GM1 in the experiment reported in Example 6.
Figure 47:
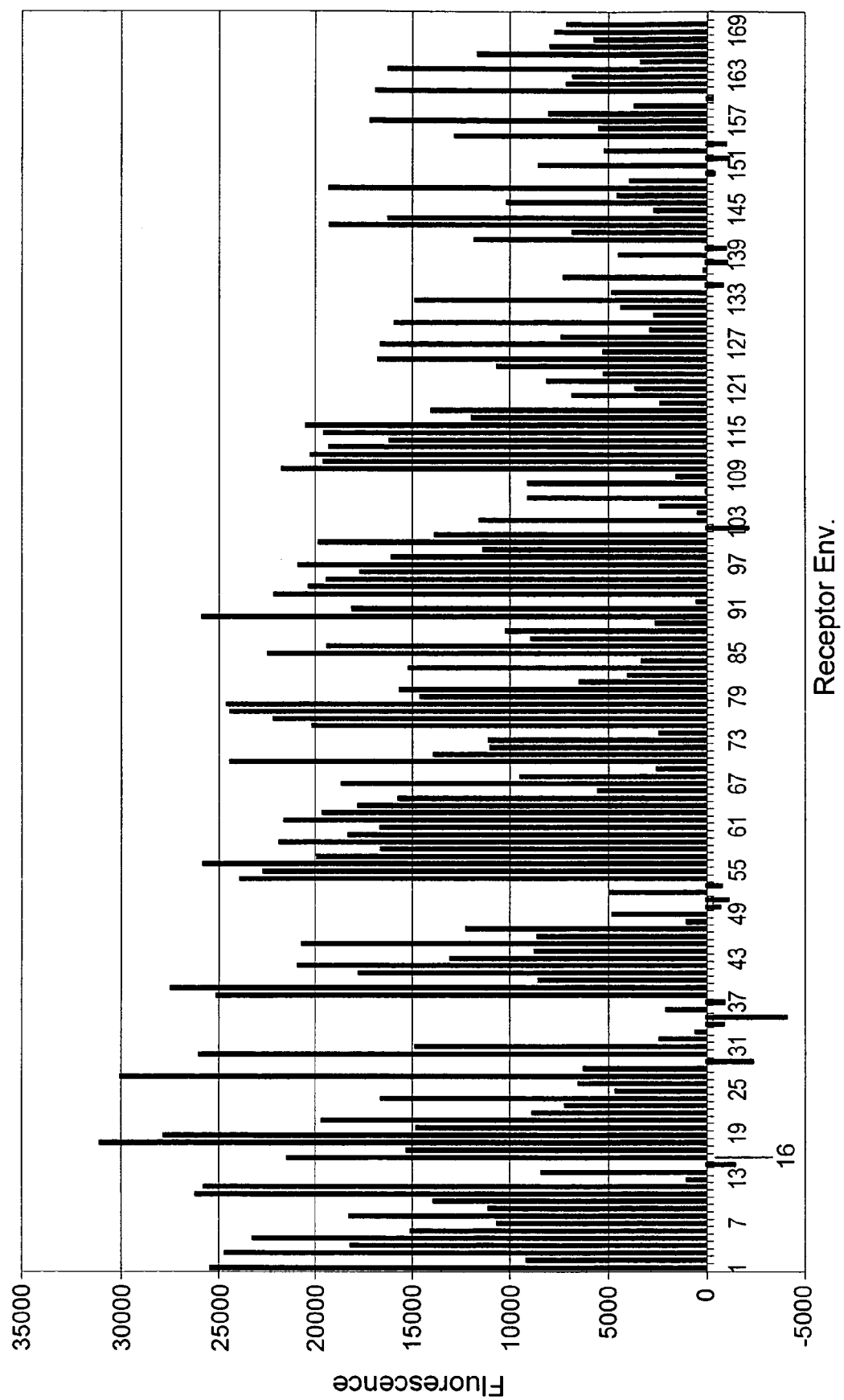
FIGS. 47-49 illustrate the fluorescence signals produced by binding of cholera toxin to the microarray of candidate artificial receptors with pretreatment with GM1 (100 µg/ml, 10 µg/ml, and 1 µg/ml GM1, respectively) in the experiment reported in Example 6.
Figure 48:
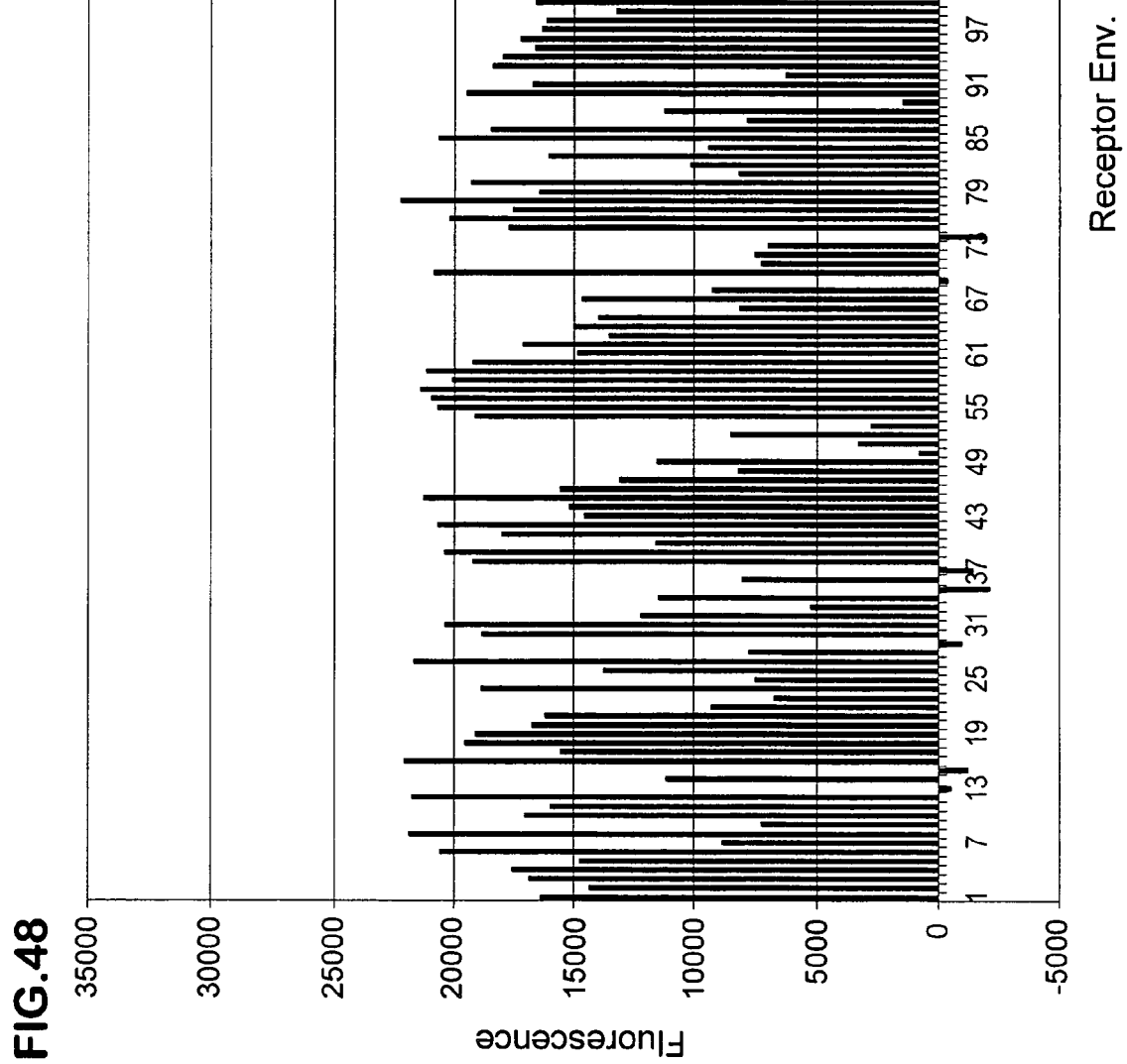
Figure 49:
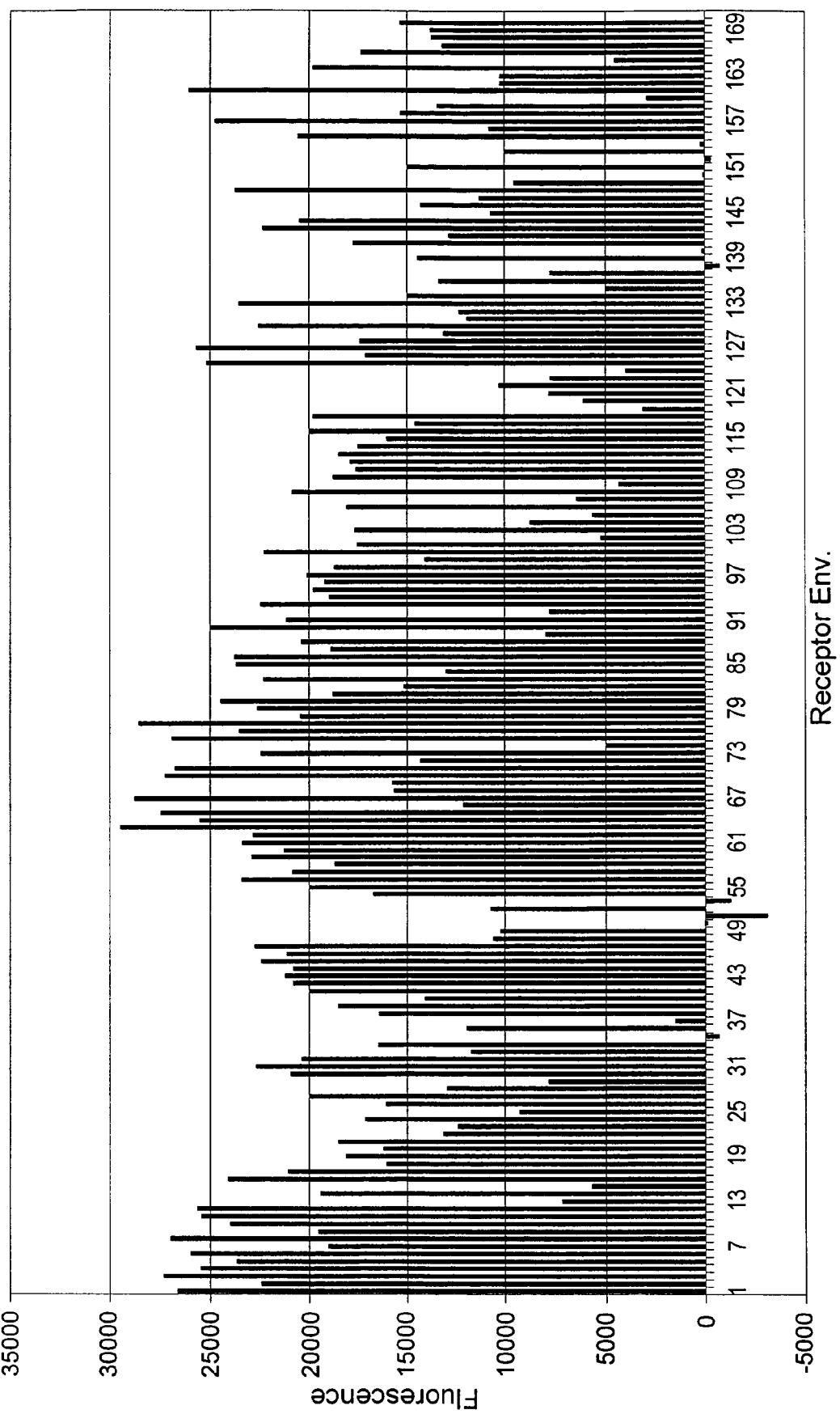

FIG. 46 illustrates the fluorescence signals produced by binding of cholera toxin to the microarray of candidate artificial receptors without pretreatment with GM1. Binding of GM1 to the microarray of candidate artificial receptors followed by binding of cholera toxin produced fluorescence signals illustrated in FIGS. 47, 48, and 49 (100 µg/ml, 10 µg/ml, and 1 µg/ml GM1, respectively).

Figure 50:
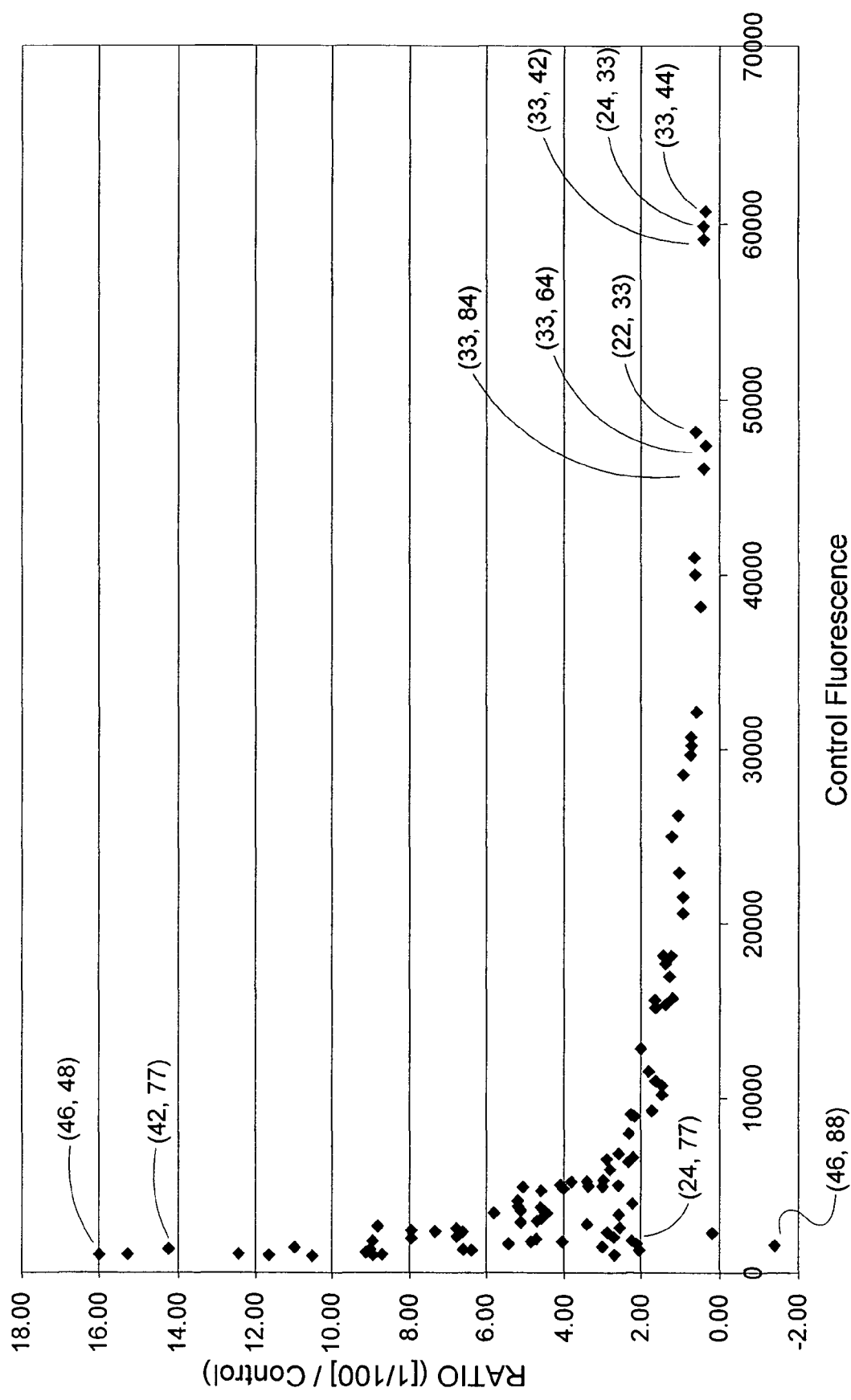
FIG. 50 illustrates the ratio of the amount bound in the presence of 1 µg/ml GM1 to the amount bound in the absence of GM1 in the experiment reported in Example 6.

The enhancement of cholera toxin binding caused by pretreatment with GM1 can be visualized as the ratio of the amount bound in the presence of GM1 to the amount bound in the absence of GM1. This ratio is illustrated in FIG. 50 for 1 µg/ml GM1. The larger the ratio, the more cholera toxin bound to the artificial receptor after pretreatment with GM1. The ratio can be as large as about 16.

In several instances minor changes in structure to the artificial receptor caused significant changes in the ratio. For example, the artificial receptor including building blocks 46 and 48 differs from that including 46 and 88 by only substitution of a single recognition element on a single building block. (xy indicates building block TyrAxBy.) The substitution of building block 48 for 88 (a change of recognition element A8 to A4) increased the ratio representing increased binding the presence of GM1 building block from about 0.5 to about 16. Similarly, the artificial receptor including building blocks 42 and 77 differs from that including 24 and 77 by only substitution of a single building block. The substitution of building block 42 for 24 increased the ratio representing increased binding the presence of GM1 building block from about 2 to about 14.

Interestingly, several building blocks that exhibited high levels of binding of cholera toxin (signals of 45,000 to 65,000 fluorescence units) and that include the building block 33 were not strongly affected by the presence of GM1 as a building block.

Conclusions

This experiment demonstrated that binding of GM1 to an artificial receptor of the present invention can significantly increase binding by cholera toxin. Minor changes in structure of the building blocks making up the artificial receptor caused significant changes in the degree to which GM1 enhanced binding of cholera toxin.

Discussion of Examples 4-6

We have previously demonstrated that an array of working artificial receptors bind to a protein target in a manner which is complementary to the specific environment presented by each region of the proteins surface topology. Thus the pattern of binding of a protein target to an array of working artificial receptors describes the proteins surface topology; including surface structures which participate in e.g., protein~small molecule, protein~peptide, protein-protein, protein~carbohydrate, protein~DNA, etc. interactions. It is thus possible to use the binding of a selected protein to a working artificial receptor array to characterize these protein~small molecule, protein~peptide, protein-protein, protein~carbohydrate, protein~DNA, etc. interactions. Moreover, it is possible to utilize the protein to array interactions to define "leads" for the disruption of these interactions.

Cholera Toxin B sub-unit binds to GM1 on the cell surface (structure of GM1). Studies to identify competitors to this binding event have shown that competitors to the cholera toxin: GM1 binding interaction (binding site) can utilize both a sugar and an alkyl/aromatic functionality (Pickens, et al., *Chemistry and Biology*, vol. 9, pp 215-224 (2002)). We have previously demonstrated that fluorescently labeled Cholera Toxin B sub-unit binds to arrays of working artificial receptors to give a defined binding pattern which (vida infra) reflects cholera toxin B's surface topology. For this study, we sought to demonstrate that the binding of the cholera toxin to at least some members of the array could be disrupted using cholera toxins natural ligand, GM1.

The results presented in the figures clearly demonstrate that these goals have been achieved. Specifically, competition between the GM1 OS pentasaccharide or GM1 and a working artificial receptor array for cholera binding clearly gave a binding pattern which was distinct from the cholera binding pattern control. Moreover, these results demonstrated the complementarity between several of the working artificial receptors which contained a naphthyl moiety when compared to working artificial receptors which only contained phenyl functionality. These results are in keeping with the active site competition studies in Pickens, et al. and indicate that the naphthyl and phenyl derivatives represent good mimics/probes for the cholera to GM1 interaction. The specificity of these interactions was particularly demonstrated by the observation that the change of a single building block out of 4 in a combination of 4 building blocks system changed a non-competitive to a significantly competitive environment. These results also indicated that selected working artificial receptors can be used to develop a high-throughput screen for the further evaluation of the cholera: GM1 interaction.

Additionally, we sought to demonstrate that an affinity support/membrane mimic could be prepared by pre-incubating an array of artificial receptors with GM1 which would then bind/capture cholera toxin in a binding pattern which could be used to select a working artificial receptor(s) for, for example, the high-throughput screen of lead compounds which will disrupt the "cholera: membrane~GM1 mimic". The GM1 pre-incubation studies clearly demonstrated that several of the working artificial receptors which were poor cholera binders significantly increased their cholera binding, presumably through an affinity interaction between the cholera toxin and both the immobilized GM1 pentasaccharide moiety and the working artificial receptor building block environment.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

What is claimed is:

1. A composition comprising:
    a scaffold moiety; and
    a plurality of building block moieties, at least one of the building block moieties comprising a tether;
        the building block moieties being covalently coupled to a functional group on the scaffold moiety;
        wherein one or more of the building block moieties further comprises a linker and independently is of formula:

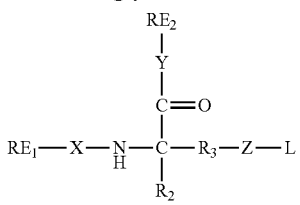

in which:
X is absent or C=O;
Y is absent, NH, or O; Z is O;
$R_2$ is H or $CH_3$;
$R_3$ is $CH_2$ or $CH_2$-phenyl;
$RE_1$ is B1, B2, B3, B4, B5, B6, B7, B8, B9, A1, A2, A3, A4, A5, A6, A7, A8, or A9;
$RE_2$ is A1, A2, A3, A4, A5, A6, A7, A8, A9, B1, B2, B3, B4, B5, B6, B7, B8, or B9;
L is $(CH_2)_n COOH$, with n=1-16;
A1 is
  $CH_2CH_3$;
A2 is
  $CH_2CH(CH_3)_2$;
A3 is

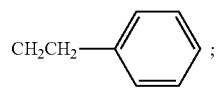

A4 is

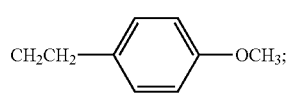

A5 is

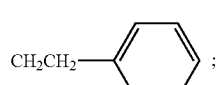

A6 is
  $CH_2CH_2-O-CH_3$;
A7 is
  $CH_2CH_2-OH$;
A8 is
  $CH_2CH_2-NH-C(O)CH_3$;
A9 is

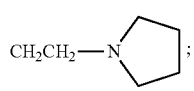

B1 is
  $CH_3$;
B2 is

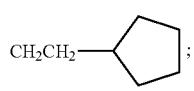

B3 is

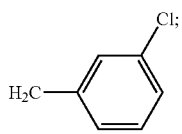

B4 is

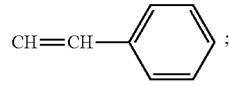

B5 is

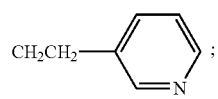

B6 is
  $CH_2-S-CH_3$;
B7 is
  $CH_2CH(OH)CH_3$;
B8 is
  $CH_2CH_2C(O)-NH_2$; and
B9 is
  $CH_2CH_2CH_2-N-(CH_3)_2$.

2. The composition of claim 1, comprising 2, 3, 4, 5, 6, or 7 different building block moieties.

3. The composition of claim 1, wherein the scaffold comprises a molecule less than or approximately equal to 1 nanometer in diameter.

4. The composition of claim 1, wherein the scaffold comprises a molecule greater than or approximately equal to 1 nanometer in diameter.

5. The composition of claim 3 wherein the scaffold is an organic molecule.

6. The composition of any of claim 3 wherein the scaffold is an organometallic molecule.

7. The composition of claim 3 wherein the scaffold is an inorganic molecule.

8. The composition of claim 1, wherein the tether is a polymer of up to 48 carbon atoms.

9. The composition of claim 1, wherein the tether is a polyethyleneimine, a polyacrylate, a salt thereof, or a combination thereof.

10. The composition of claim 1, wherein the tether is PEG 1450, PEG 3350, PEG 4500, PEG 8000, or PEG 20,000.

11. The composition of claim 1, wherein the tether is a branched or straight chain, substituted or unsubstituted, $C_{6-36}$ alkyl; a branched or straight chain, substituted or unsubstituted, $C_{6-36}$ alkenyl with 1 to 4 double bonds; a branched or straight chain, substituted or unsubstituted, $C_{6-36}$ alkynyl with 1 to 4 triple bonds; or a polyaromatic hydrocarbon moiety.

* * * * *